United States Patent [19]

Hioki et al.

[11] Patent Number: 5,429,920
[45] Date of Patent: * Jul. 4, 1995

[54] SILVER HALIDE EMULSION

[75] Inventors: Takanori Hioki; Tadashi Ikeda, both of Kanagawa, Japan

[73] Assignee: Fuji Photo Film Co., Ltd., Kanagawa, Japan

[*] Notice: The portion of the term of this patent subsequent to Jun. 29, 2010 has been disclaimed.

[21] Appl. No.: 108,253

[22] Filed: Aug. 19, 1993

Related U.S. Application Data

[63] Continuation of Ser. No. 658,714, Feb. 21, 1991, abandoned.

[30] Foreign Application Priority Data

Feb. 22, 1990 [JP] Japan .................................. 2-41998

[51] Int. Cl.⁶ .................................................. G03C 1/20
[52] U.S. Cl. ........................................ 430/584; 430/577; 430/591; 430/592; 430/600; 430/607; 430/944
[58] Field of Search ............... 430/582, 583, 584, 585, 430/586, 587, 576–579, 591–595, 600, 572, 607, 944; 548/455

[56] References Cited

U.S. PATENT DOCUMENTS

| | | | |
|---|---|---|---|
| 2,481,464 | 9/1949 | Anish | 430/587 |
| 3,541,089 | 11/1970 | Heseltine et al. | 548/455 |
| 3,622,317 | 11/1971 | Bird | 430/586 |
| 4,536,473 | 8/1985 | Mihara | 430/575 |
| 5,223,389 | 6/1993 | Matsunaga et al. | 430/583 |

FOREIGN PATENT DOCUMENTS

| | | |
|---|---|---|
| 0123983 | 11/1984 | European Pat. Off. |
| 0256858 | 2/1988 | European Pat. Off. |
| 70503 | 12/1988 | France |
| 1008573 | 12/1954 | Germany |
| 592267 | 9/1947 | United Kingdom |
| 115344 | 5/1969 | United Kingdom |

OTHER PUBLICATIONS

European Search Report 91 10 2008; Mar. 22, 1991; S. Magrizos; The Hague.

Primary Examiner—Thorl Chea
Attorney, Agent, or Firm—Sughrue, Mion, Zinn, Macpeak & Seas

[57] ABSTRACT

A silver halide emulsion containing at least one member of methine dyes represented by the following general formula (I):

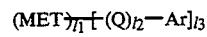

$$[(MET)_{l_1}{-}(Q)_{l_2}{-}Ar]_{l_3} \qquad (I)$$

wherein MET represents an atomic group having a methine dye structure; Q represents a bivalent bonding group comprising at least one atom of carbon atom, nitrogen atom, sulfur atom and oxygen atom or an atomic group having at least one atom of carbon atom, nitrogen atom, sulfur atom and oxygen atom; Ar represents a group which has an aromatic character and derives from a polycyclic compound composed of 8 or more atoms excluding nitrogen atom; $l_1$ represents 1 or 2; $l_2$ represents 0 or 1; and $l_3$ represents 1, 2, 3 or 4.

17 Claims, No Drawings

SILVER HALIDE EMULSION

This is a Continuation of application Ser. No. 07/658,714 filed Feb. 21, 1991, now abandoned.

FIELD OF THE INVENTION

This invention relates to a silver halide emulsion, and more particularly to a silver halide emulsion which has improved properties with regard to the problem of a change in sensitivity under natural preservation.

BACKGROUND OF THE INVENTION

It is conventionally well known that sensitizing dyes are added to silver halide emulsions in the preparation of silver halide light-sensitive materials to enlarge the sensitive wavelength regions of the silver halide emulsions, thus optically sensitizing the silver halide emulsions.

Many compounds which can be used as spectral sensitizing dyes for this purpose are conventionally known. Examples of these compounds include cyanine dyes, merocyanine dyes and xanthene dyes described in T. H. James, *The Theory of the Photographic Process*, third edition, pages 198-228 (Macmillan, N.Y., 1966).

When these sensitizing dyes are applied to the silver halide emulsions, the dyes not only can enlarge the sensitive wavelength regions of the silver halide emulsions, but also must meet the following requirements.

(1) Spectral sensitization region is proper.
(2) Sensitizing efficiency is high and sufficiently high sensitivity can be obtained.
(3) Fogging is not caused.
(4) The variation of sensitivity caused by a change in temperature during exposure is little.
(5) The dyes do not have an adverse interaction with other additives such as stabilizers, anti-fogging agents, coating aids, color formers, etc.
(6) A change in sensitivity is not caused when silver halide emulsions containing the sensitizing dyes are stored. A change in sensitivity is not caused particularly when the emulsions containing the sensitizing dyes are stored under high temperature and humidity conditions.
(7) Color turbidity (color mixing) is not caused after development by diffusing sensitizing dyes added in other light-sensitive layers.

The above-described conditions are important factors in the preparation of the silver halide emulsions of silver halide color photographic materials.

Many attempts have been made to prevent a lowering in sensitivity from being caused during the preservation of raw samples. However, a lowering in sensitivity cannot be prevented to the desired level.

Particularly, when polymethine dyes having an oxidation potential of 0.60 ($V_{vs}SCE$) or lower are used as sensitizing dyes, a lowering in sensitivity during the preparation of raw samples is large and a sufficient performance cannot be obtained.

SUMMARY OF THE INVENTION

An object of the present invention is to provide a silver halide emulsion which scarcely causes a lowering in sensitivity during the preservation thereof.

Another object of the present invention is to provide a silver halide photographic material which has high sensitivity and scarcely causes an increase in fogging and a lowering in sensitivity during preservation under high temperature and/or high humidity conditions (Namely, the silver halide photographic material being excellent in raw preservability).

Other objects of the present invention will become apparent from the following description.

The above-described objects of the present invention have been achieved by providing a silver halide emulsion which contains at least one member of methine dyes represented by the following general formula (I).

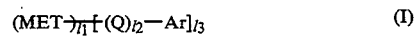  (I)

wherein MET represents an atomic group having a methine dye structure; Q represents a bivalent bonding group comprising at least one atom of carbon atom, nitrogen atom, sulfur atom and oxygen atom or an atomic group having at least one atom of carbon atom, nitrogen atom, sulfur atom and oxygen atom; Ar represents a group which has an aromatic character (aromaticity) and derives from a polycyclic compound composed of 8 or more atoms excluding nitrogen atom; $l_1$ represents 1 or 2; $l_2$ represents 0 or 1 and preferably 1; and $l_3$ represents 1, 2, 3 or 4.

The compounds where Ar' is substituted for Ar are preferred.

Ar' represents a group which has an aromatic character and derives from a polycyclic corbon compound whose ring is composed of 9 or more carbon atoms.

More preferred is the case where the methine dyes represented by general formula (I) have an oxidation potential of 0.60 ($V_{vs}SCE$) or lower and further more preferred is the case where the methine dyes have an oxidation potential of 0.45 ($V_{vs}SCE$) or lower. Still more preferred is the case where MET has a hexamethinemerocyanine structure or a heptamethinecyanine structure.

DETAILED DESCRIPTION OF THE INVENTION

Now, the present invention will be illustrated in more detail below.

In general formula (I), the group represented by MET represents generally a cyanine structure formed by bonding a nitrogen-containing heterocyclic ring called a basic nucleus and another nitrogen-containing heterocyclic ring to each other through conjugated double bonds so as to allow them to be conjugated with each other; a merocyanine structure formed by bonding carbonyl group in an acidic nucleus and nitrogen atom in a basic nucleus in a structure having a heterocyclic ring called acidic nucleus and a basic nucleus to each other through conjugated double bonds so as to allow them to be conjugated to each other; a rhodacyanine structure having a composite structure of them; an oxonol structure; a hemicyanine structure; a styryl structure; or a benzylidene structure.

Examples of these polymethine dyes include those described in T. H. James, *Theory of Photographic Process*, Chapter 8, (1977, Macmillan), D. M. Sturmer, *The Chemistry of Heterocyclic Compound*, ed. A. Weissberger and E. C. Taylor (1977, John Wiley and Sons, New York), etc.

Q represents a bivalent bonding group comprising at least one atom of carbon atom, nitrogen atom, sulfur atom and oxygen atom or an atomic group having at least one atom of carbon atom, nitrogen atom, sulfur atom and oxygen atom.

Preferably, Q represent a bivalent bonding group having not more than 20 carbon atoms, which is composed of an alkylene group (e.g., methylene group, ethylene group, propylene group, butylene group, pentylene group), an arylene group (e.g., phenylene group, naphthylene group), an alkenylene group (e.g., ethenylene group, propenylene group), a sulfonyl group, a sulfinyl group, a thioether group, an ether group, carbonyl group, a group of

(wherein $R^1$ is hydrogen atom, a substituted or unsubstituted alkyl group or a substituted or unsubstituted aryl group) or a heterocyclic bivalent group (e.g., 6-chloro-1,3,5-triazine-2,4-diyl group, pyrimidine-2,4-diyl group, quinoxaline-2,3-diyl group) or a combination of two or more of these groups.

$l_1$ represents 1 or 2; $l_2$ represents 0 or 1; and $l_3$ represents 1, 2, 3 or 4.

Preferably, $l_1$ is 1; $l_2$ is 1; and $l_3$ represents 1 or 2.

Ar and Ar' are illustrated in more detail below.

The definition of the aromatic character is described in *Iwanami Rikagaku Jiten*, p-1258, 1259, the third edition, an enlarged edition, written by Monichi Tamamushi (published by Iwanami Shoten 1981) (written in Japanese).

Examples of the polycyclic compound from which Ar or Ar' is derived include the following compounds.

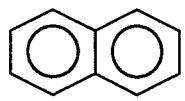
(a)

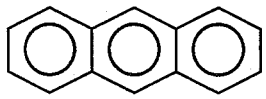
(b)

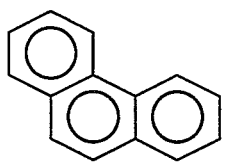
(c)

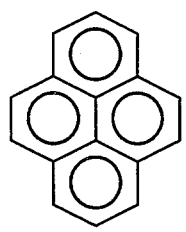
(d)

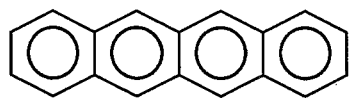
(e)

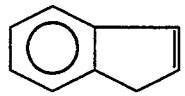
(f)

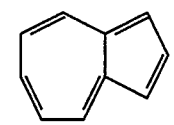
(g)

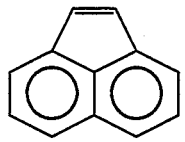
(h)

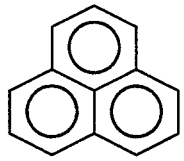
(i)

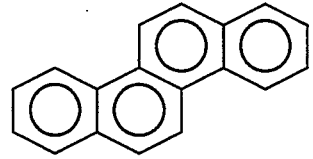
(j)

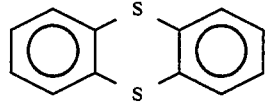
(k)

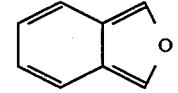
(l)

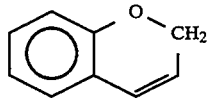
(m)

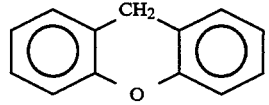
(n)

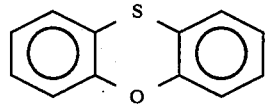
(o)

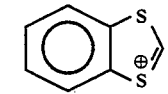
(p)

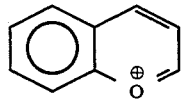
(q)

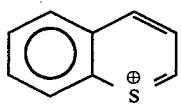
(r)

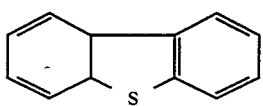
(s)

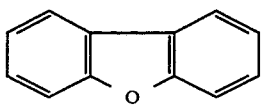
(t)

These polycyclic compounds may be substituted. Examples of substituent groups include hydrogen atom, a substituted or unsubstituted alkyl group (e.g., methyl, ethyl, propyl, butyl, hydroxyethyl, trifluoromethyl, benzyl, sulfopropyl, diethylaminoethyl, cyanopropyl, adamantyl, p-chlorophenethyl, ethoxyethyl, ethylthioethyl, phenoxyethyl, carbamoylethyl, carboxyethyl, ethoxycarbonylmethyl, acetylaminoethyl), an unsubstituted or substituted alkenyl group. (e.g., allyl, styryl), an unsubstituted or substituted aryl group (e.g., phenyl, naphthyl, p-carboxyphenyl, 3,5-dicarboxyphenyl, m-sulfophenyl, p-acetamidophenyl, 3-caprylamidophenyl, m-sulfophenyl, m-hydroxyphenyl, p-nitrophenyl, 3,5-dichlorophenyl, p-anisyl, o-anisyl, p-cyanophenyl, p-N-methylureidophenyl, m-fluorophenyl, p-tolyl, m-tolyl), a residue of a heterocyclic group which may be substituted (e.g., pyridyl, 5-methyl-2-pyridyl, thienyl), a halogen atom (e.g., chlorine, bromine, fluorine), a mercapto group, cyano group, carboxyl group, sulfo group, hydroxyl group, a carbamoyl group, a sulfamoyl group, an amino group, nitro group, an alkoxy group which may be substituted (e.g., methoxy, ethoxy, 2-methoxyethoxy, 2-phenylethoxy), an aryloxy group which may be substituted (e.g., phenoxy, p-methylphenoxy, p-chlorophenoxy), an acyl group (e.g., acetyl, benzoyl), an acylamino group (e.g., acetylamino, caproylamino), a sulfonyl group (e.g., methanesulfonyl, benzenesulfonyl), a sulfonylamino group (e.g., methanesulfonylamino, benzenesulfonylamino), a substituted amino group (e.g., diethylamino, hydroxyamino), an alkyl- or arylthio group (e.g., methylthio, carboxyethylthio, sulfobutylthio, phenylthio), an alkoxycarbonyl group (e.g., methoxycarbonyl) and an aryloxycarbonyl group (e.g., phenoxycarbonyl). These substituent groups may be further substituted with Ar through a bivalent bonding group Q or a single bond.

Examples of substituent groups by which the above-described substituent groups may be further substituted include an alkyl group, an alkenyl group, an aryl group, hydroxyl group, carboxyl group, sulfo group, nitro group, cyano group, halogen, an alkoxy group, an aryloxy group, an alkoxycarbonyl group, an acyl group, an acylamino group, a sulfonamino group, a carbamoyl group and a sulfamoyl group.

At least one of these substituent groups may be a bivalent bonding group Q or a single bond, and at least one of these substituent groups is preferably a bivalent bonding group Q.

The measurement of oxidation potential was made by using phase discrimination second higher harmonics alternating current polargraphy. The measurement is illustrated in detail below. Acetonitrile (spectral grade) dried in 4A-1/16 molecular sieves was used as a solvent, and n-tetrapropylammonium perchlorate (special reagent for polarograph) was used as a supporting eletrolyte). A sample solution was prepared by dissolving a red-sensitive sensitizing dye in an amount of $10^{-3}$ to $10^{-5}$ mol/l in acetonitrile containing 0.1M supporting electrolyte. Before measurement, the sample solution was deoxidated for at least 15 minutes by using ultrahigh-purity argon gas (99.999%) passed through an aqueous high alkaline solution of pyrogallol and further calcium chloride. A working electrode was a rotating platinum electrode, a reference electrode was a saturated calomel electrode (SCE), and further platinum was used for a counter electrode. The reference electrode was connected with the sample solution through rugin tube filled with acetonitrile containing 0.1M supporting electrolyte, and Vycor glass was used for liquid-junction part. The measurement was made at 25° C. under such a condition that the tip of rugin tube was 5 to 8 mm away from the tip of the rotating platinum electrode. The measurement of oxidation potential by means of phase discrimination second higher harmonics alternating current voltammetry is described in *Journal of Imaging Science*, Vol. 30, pages 27 to 35 (1986).

The hexamethinemerocyanine structure which can be preferably used as MET in the present invention is represented by the following general formula (II). The heptamethinecyanine structure which can be preferably used as MET in the present invention is represented by the following general formula (III).

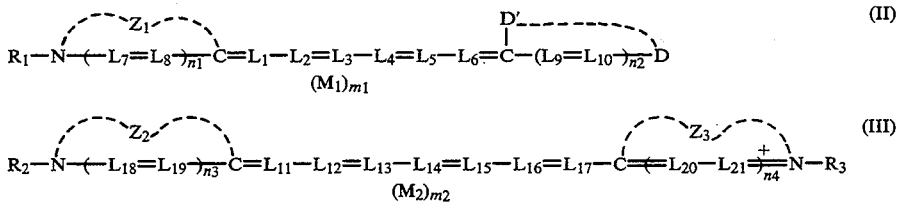

wherein $Z_1$, $Z_2$ and $Z_3$ represent each an atomic group required for forming a 5-memered or 6-membered nitrogen-containing heterocyclic ring; D and D' represent each an atomic group required for forming a non-cyclic or cyclic acidic nucleus; $R_1$, $R_2$ and $R_3$ represent each an alkyl group; $L_1$, $L_2$, $L_3$, $L_4$, $L_5$, $L_6$, $L_7$, $L_8$, $L_9$, $L_{10}$, $L_{11}$, $L_{12}$, $L_{13}$, $L_{14}$, $L_{15}$, $L_{16}$, $L_{17}$, $L_{18}$, $L_{19}$, $L_{20}$ and $L_{21}$ represent each methine group or a substituted methine group, or each may be combined together with other methine group to form a ring, or each may be combined together with auxochrome to form a ring; $n_1$, $n_2$, $n_3$ and $n_4$ represent each 0 or 1; $M_1$ and $M_2$ represent each a counter ion for charge neutralization; and $m_1$ and $m_2$ represent each a number of 0 or greater which is required for neutralizing electric charge in the molecule.

In general formulae (II) and (III), at least one Ar is substituted through a bivalent bonding group Q or a single bond, and at least one Ar is preferably substituted through a bivalent bonding group Q.

The compounds represented by general formulae (II) and (III) are illustrated in more detail below.

$R_1$, $R_2$ and $R_3$ are preferably each an unsubstituted alkyl group having not more than 18 carbon groups (e.g., methyl, ethyl, propyl, butyl, pentyl, octyl, decyl, dodecyl, octadecyl) or a substituted alkyl group having not more than 18 carbon atoms [examples of substituent groups include carboxyl group, sulfo group, cyano group, a halogen atom (e.g., fluorine, chlorine, bromine), hydroxyl group, an alkoxycarbonyl group having not more than 8 carbon atoms (e.g., methoxycarbonyl, ethoxycarbonyl, phenoxycarbonyl, benzyloxycarbonyl), an alkoxy group having not more than 8 carbon atoms (e.g., methoxy, ethoxy, benzyloxy, phenethyloxy), a monocyclic aryloxy group having not more than 10 carbon atoms (e.g., phenoxy, p-tolyloxy), an acyloxy group having not more than 3 carbon atoms (e.g., acetyloxy, propionyloxy), an acyl group having not more than 8 carbon atoms (e.g., acetyl, propionyl, benzoyl, mesyl), a carbamoyl group (e.g., carbamoyl, N,N-dimethylcarbamoyl, morpholinocarbonyl, piperidinocarbonyl), a sulfamoyl group (e.g., sulfamoyl, N,N-dimethylsulfamoyl, morpholinosulfonyl, piperidinosulfonyl) and an aryl group having not more than 10 carbon atoms (e.g., phenyl, 4-chlorophenyl, 4-methylphenyl, α-naphthyl).

More preferably, $R_1$, $R_2$ and $R_3$ are each an unsubstituted alkyl group (e.g., methyl group, ethyl group, n-propyl group, n-butyl group, n-pentyl group, n-hexyl group), a carboxyalkyl group (e.g., 2-carboxyethyl group, carboxymethyl group) or a sulfoalkyl group (e.g., 2-sulfoethyl group, 3-sulfopropyl group, 4-sulfobutyl group, 3-sulfobutyl group).

$(M_1)_{m1}$ and $(M_2)_{m2}$ are included in the formulae to show the presence or absence of a cation or an anion when it is required that the ionic charge of the dye is neutralized. Whether a dye has a cation, an anion or a net ionic charge varies depending on auxochrome and substituent groups. Typical cations are inorganic or organic ammonium ions and alkali metal ions. The anion may be any of an inorganic anion and an organic anion. Examples of the anion include halogen anions (e.g., fluorine ion, chlorine ion, bromine ion, iodine ion), substituted arylsulfonate ions (e.g., p-toluenesulfonate ion, p-chlorobenzenesulfonate ion), aryldisulfonate ions (e.g., 1,3-benzenedisulfonate ion, 1,5-naphthalenedisulfonate ion, 2,6-naphthalenedisulfonate ion), alkylsulfate ions (e.g., methylsulfate ion), sulfate ion, thiocyanate ion, perchlorate ion, tetrafluoroborate ion, picrate ion, acetate ion and trifluoromethanesulfate ion.

Among them, ammonium ion, iodide ion and p-toluenesulfonate ion are preferred.

Examples of nuclei formed by $Z_1$, $Z_2$ or $Z_3$ include thiazole nuclei [e.g., thiazole nucleus (e.g., thiazole, 4-methylthiazole, 4-phenylthiazole, 4,5-dimethylthiazole, 4,5-diphenylthiazole), benzthiazole nucleus (e.g., benzthiazole, 4-chlorobenzthiazole, 5-chlorobenzthiazole, 6-chlorobenzthiazole, 5-nitrobenzthiazole, 4-methylbenzthiazole, 5-methylbenzthiazole, 6-methylbenzthiazole, 5-bromobenzthiazole, 6-bromobenzthiazole, 5-iodobenzthiazole, 5-phenylbenzthiazole, 5-methoxybenzthiazole, 6-methoxybenzthiazole, 5-ethoxybenzthiazole, 5-ethoxycarbonylbenzthiazole, 5-carboxybenzthiazole, 5-phenethylbenzthiazole, 5-fluorobenzthiazole, 5-chloro-6-methylbenzthiazole, 5,6-dimethylbenzthiazole, 5,6-dimethoxybenzthiazole, 5-hydroxy-6-methylbenzthiazole, tetrahydrobenzthiazole, 4-phenylbenzthiazole), naphthothiazole nucleus (e.g., naphtho[2,1-d]thiazole, naphtho[1,2-d]thiazole, naphtho[2,3-d]thiazole, 5-methoxynaphtho[1,2-d]thiazole, 7-ethoxynaphtho[2,1-d]-thiazole, 8-methoxynaphtho[2,1-d]thiazole, 5-methoxynaphtho[2,3-d]thiazole)], thiazoline nucleus (e.g., thiazoline, 4-methylthiazoline, 4-nitrothiazoline), oxazole nuclei [e.g., oxazole nucleus (e.g., oxazole, 4-methyloxazole, 4-nitrooxazole, 5-methyloxazole, 4-phenyloxazole, 4,5-diphenyloxazole, 4-ethyloxazole), benzoxazole nucleus (e.g., benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-nitrobenzoxazole, 5-trifluoromethylbenzoxazole, 5-hydroxybenzoxazole, 5-carboxybenzoxazole, 6-methylbenzoxazole, 6-chlorobenzoxazole, 6-nitrobenzoxazole, 6-methoxybenzoxazole, 6-hydroxybenzoxazole, 5,6-dimethylbenzoxazole, 4,6-dimethylbenzoxazole, 5-ethoxybenzoxazole), naphthoxazole nucleus (e.g., naphtho[2,1-d]oxazole, naphtho[1,2-d]oxazole, naphtho[2,3-d]oxazole, 5-nitronaphtho[2,1-d]oxazole), oxazoline nucleus (e.g., 4,4-dimethyloxazoline), selenazole nuclei [e.g., selenazole nucleus {e.g., 4-methylselenazole, 4-nitroselenazole, 4-phenylselenazole), benzoselenazole nucleus (e.g., benzoselenazole, 5-chlorobenzoselenazole, 5-nitrobenzoselenazole, 5-methoxybenzoselenazole, 5-hydroxybenzoselenazole, 6-nitrobenzoselenazole, 5-chloro-6-nitrobenzoselenazole, 5,6-dimethylbenzoselenazole), naphthoselenazole nucleus (e.g., naphtho[2,1-d]selenazole, naphtho[1,2-d]selenazole)], selenazoline nucleus (e.g., selenazoline, 4-methylselenazoline), tellurazole nuclei [e.g., tellurazole nucleus (e.g., tellurazole, 4-methyltellurazole, 4-phenyltellurazole), benzotellurazole nucleus (e.g., benzotellurazole, 5-chlorobenzotellurazole, 5-methylbenzotellurazole, 5,6-dimethylbenzotellurazole, 6-methoxybenzotellurazole), naphthotellurazole nucleus (e.g., naphtho[2,1-d]tellurazole, naphtho[1,2-d]tellurazole)], telluzoline nucleus (e.g., tellurazoline, 4-methyltellurazoline), 3,3-dialkylindolenine nucleus (e.g., 3,3-dimethylindoleneine, 3,3-diethylindolenine, 3,3-dimethyl-5-cyanoindolenine, 3,3-dimethyl-6-nitroindolenine, 3,3-dimethyl-5-nitroindolenine, 3,3-dimethyl-5-methoxyindolenine, 3,3,5-trimethylindolenine, 3,3-dimethyl-5-chloroindolenine), imidazole nuclei [e.g., indazole nucleus (e.g., 1-alkylimidazole, 1-alkyl-4-phenylimidazole, 1-arylimidazole), benzimidazole nucleus (e.g., 1-alkylbenzimidazole, 1-alkyl-5-chlorobenzimidazole, 1-alkyl-5,6-dichlorobenzimidazole, 1-alkyl-5-methoxybenzimidazole, 1-alkyl-5-cyanobenzimidazole, 1-alkyl-5-fluorobenzimidazole, 1-alkyl-5-trifluoromethylbenzimidazole, 1-alkyl-6-chloro-5-cyanobenzimidazole, 1-alkyl-6-chloro-5-trifluoromethylbenzimidazole, 1-allyl-5,6-dichlorobenzimidazole, 1-allyl-5chlorobenzimidazole, 1-arylbenzimidazole, 1-aryl-5chlorobenzimidazole, 1-aryl-5,6-dichlorobenzimidazole, 1-aryl-5-methoxybenzimidazole, 1-aryl-5-cyanobenzimidazole), naphthoimidazole nucleus (e.g., 1-alkylnaphtho[1,2-d]imidazole, 1-arylnaphtho[1,2-d]imidazole, said alkyl portion is an alkyl group having 1 to 8 carbon atoms, preferably an unsubstituted alkyl group such as methyl, ethyl, propyl, isopropyl, butyl or the like or a hydroxyalkyl group (e.g., 2-hydroxyethyl, 3-hydroxypropyl) with methyl group and ethyl group being particularly preferred, said aryl portion is an aryl group such as phenyl, a halogen (e.g., chlorine)substituted phenyl, an alkyl (e.g., methyl)-substituted phenyl or an alkoxy (e.g., methoxy)-substituted phenyl], pyridine nucleus (e.g., 2-pyridine, 4-pyridine, 5-methyl-2-pyridine, 3-methyl-4-pyridine), quinoline nuclei [e.g., quinoline nucleus (e.g., 2-quinoline, 3-methyl-2-quinoline, 5-ethyl-2-quinoline, 6-methyl-2-quinoline, 6-nitro-2-quinoline, 8-fluoro-2-quinoline, 6-methoxy-2-quinoline, 6-hydroxy-2-quinoline, 8-chloro-2-quinoline, 4-quinoline, 6-ethoxy-4-quinoline, 6-nitro-4-quinoline, 8-chloro-4-quinoline, 8-fluoro-4-quinoline, 8-methyl-4-quinoline, 8-methoxy-4-quinoline, 6-methyl-4-quinoline, 6-methoxy-4-quinoline, 6-chloro-4-quinoline), isoquinoline nucleus (e.g., 6-nitro-1-isoquinoline, 3,4-dihydro-1-isoquinoline, 6-nitro-3-isoquinoline)], imidazo[4,5-b]quinoxaline nucleus (e.g., 1,3-diethylimidazo[4,5-b]quinoxaline, 6-chloro-1,3-diallylimidazo[4,5-b]quinoxaline), oxadiazole nucleus, thiadiazole nucleus, tetrazole nucleus and pyrimidine nucleus.

Preferred examples of the nuclei formed by $Z_1$, $Z_2$ or $Z_3$ are benzthiazole nucleus, naphthothiazole nucleus, benzoxazole nucleus, naphthoxazole nucleus, benzimidazole nucleus, 2-quinoline nucleus and 4-quinoline nucleus.

D and D' represent each an atomic group required for forming an acidic nucleus and may be in any form of the acidic nuclei of general merocyanine dyes. In a preferred form, D is thiocarbonyl group or carbonyl group and D' is a residue of an atomic group required for forming an acidic nucleus.

D and D' may be combined together to form a 5-membered or 6-membered heterocyclic ring comprising carbon, nitrogen and chalcogen (typically oxygen, sulfur, selenium and tellurium) atoms.

Preferred examples of nucleus formed by D and D' include nuclei of 2-pyrazoline-5-one, pyrazolidine-3,5-dione, imidazoline-5-one, hydantoin, 2- or 4-thiohydantoin, 2-imino-oxazolidine-4-one, 2-oxazoline-5-one, 2-thio-oxazolidine-2,4-dione, isoxazoline-5-one, 2-thiazoline-4-one, thiazolidine-4-one, thiazolidine-2,4-dione, rhodanine, thiazolidine-2,4-dithione, isorhodanine, indane-1,3-dione, thiophene-3-one, thiophene-3-one-1,1-dioxide, indoline-2-one, indoline-3-one, indazoline-3-one, 2-oxoindazolinium, 3-oxoindazolium, 5,7-dioxo-6,7-dihydrothiazolo[3,2-a]pyrimidine, cyclohexane-1,3-dione, 3,4-dihydroisoquinoline-4-one, 1,3-dioxane-4,6-dione, barbituric acid, 2-thiobarbituric acid, chroman-2,4-dione, indazoline-2-one and pyrido[1,2-a]pyrimidine-1,3-dione.

More preferred are 3-alkylrhodanine, 3-alkyl-2-thiooxazolidine-2,4-dione and 3-alkyl-2-thiohydantoin.

Preferred examples of substituent groups which may be attached to nitrogen atom in the nucleus include hydrogen atom, an alkyl group having 1 to 18 carbon atoms, preferably 1 to 7 carbon atoms, particularly preferably 1 to 4 carbon atoms (e.g., methyl, ethyl, propyl, isopropyl, butyl, isobutyl, hexyl, octyl, dodecyl, octadecyl), a substituted alkyl group [e.g., an aralkyl group (e.g., benzyl, 2-phenylethyl), a hydroxyalkyl group (e.g., 2-hydroxyethyl, 3-hydroxypropyl), a carboxyalkyl group (e.g., 2-carboxyethyl, 3-carboxypropyl, 4-carboxybutyl, carboxymethyl), an alkoxyalkyl group (e.g., 2-methoxyethyl, 2-(2-methoxyethoxy)ethyl), a sulfoalkyl group (e.g., 2-sulfoethyl, 3-sulfopropyl, 3-sulfobutyl, 4-sulfobutyl, 2-(3-sulfopropoxy)ethyl, 2-hydroxy-3-sulfopropyl, 3-sulfopropoxyethoxyethyl), a sulfatoalkyl group (e.g., 3-sulfatopropyl, 4-sulfatobutyl), a heterocyclic ring-substituted alkyl group (e.g., 2-(pyrrolidine-2-one-1-yl)ethyl, tetrahydrofurfuryl, 2-morpholinoethyl), 2-acetoxyethyl, carbomethoxymethyl, 2-methanesulfonylaminoethyl], allyl group, an aryl group (e.g., phenyl, 2-naphthyl), a substituted aryl group (e.g., 4-carboxyphenyl, 4-sulfophenyl, 3-chlorophenyl, 3-methylphenyl) and a heterocyclic group (e.g., 2-pyridyl, 2-thiazolyl).

More preferred are an unsubstituted alkyl group (e.g., methyl, ethyl, n-propyl, n-butyl, n-pentyl, n-hexyl), a carboxyalkyl group (e.g., carboxymethyl, 2-carboxyethyl) and a sulfoalkyl group (e.g., 2-sulfoethyl).

$L_1$, $L_2$, $L_3$, $L_4$, $L_5$, $L_6$, $L_7$, $L_8$, $L_9$, $L_{10}$, $L_{11}$, $L_{12}$, $L_{13}$, $L_{14}$, $L_{15}$, $L_{16}$, $L_{17}$, $L_{18}$, $L_{19}$, $L_{20}$ and $L_{21}$ represent each methine group or a substituted methine group [e.g., examples of substituent groups include a substituted or unsubstituted alkyl group (e.g., methyl group, ethyl group, 2-carboxyethyl group), a substituted or unsubstituted aryl group (e.g., phenyl group, o-carboxyphenyl group), a heterocyclic group (e.g., barbituric acid), a halogen atom (e.g., chlorine atom, bromine atom), an alkoxy group (e.g., methoxy group, ethoxy group), an amino group (e.g., N,N-diphenylamino group, N-methyl-N-phenylamino group, N-methylpiperadino group) and an alkylthio group (e.g., methylthio group, ethylthio group)]. Each may be combined together with other methine group or auxochrome to form a ring.

It is preferred that any one group of $L_2$ and $L_4$ or $L_3$ and $L_5$ is combined together to form a ring. It is also preferred that one group of $L_{12}$ and $L_{14}$, $L_{13}$ and $L_{15}$ or $L_{14}$ and $L_{16}$ is combined together to form a ring.

Particularly preferred ring structures formed by $L_2$ and $L_4$, $L_{12}$ and $L_{14}$ or $L_{14}$ and $L_{16}$ are the following ring structures.

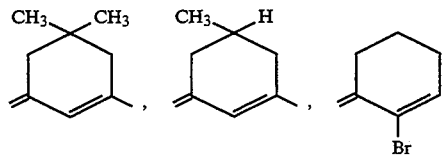

Particularly preferred ring structures formed by $L_3$ and $L_5$ or $L_{13}$ and $L_{15}$ are the following ring structures.

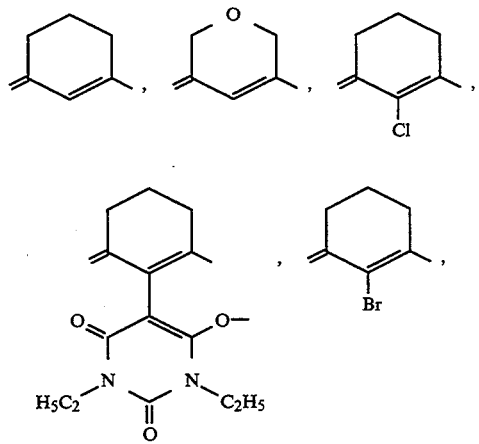

-continued

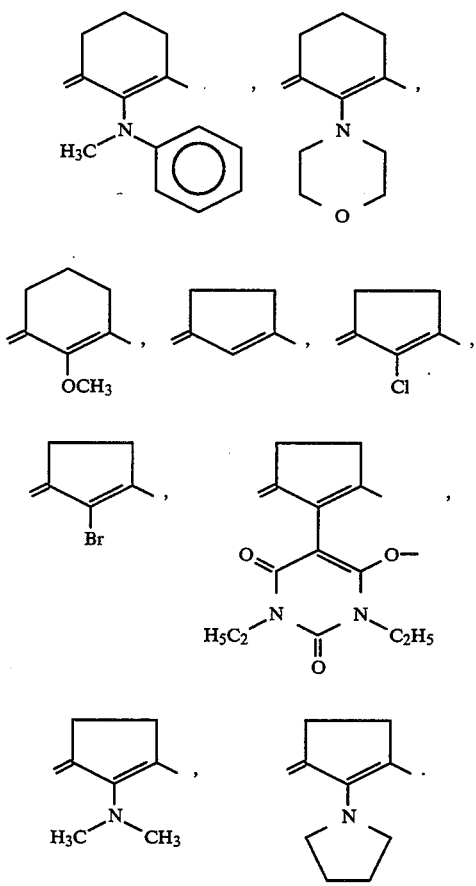

Namely, when $L_3$ and $L_5$ or $L_{13}$ and $L_{15}$ are combined together to form a ring structure, $L_4$ and $L_{14}$ are preferably each unsubstituted methine group or a substituted methine group [methine group substituted by an unsubstituted alkyl group (e.g., methyl), an alkoxy group (e.g., methoxy), an amino group (e.g., N,N-diphenylamino), a halogen atom (e.g., chlorine) or an acidic nucleus represented by D and D'].

Other L is preferably unsubstituted methine group.

In general formulas (II) and (III), at least one $-(Q)_n$Ar is substituted and may be attached to any of the 5-membered or 6-membered nitrogen-containing heterocyclic ring represented by $Z_1$, $Z_2$ and $Z_3$, the acidic nucleus represented by D and D', the alkyl group represented by $R_1$, $R_3$ and $R_4$, and methine group represented by $L_1$ to $L_{12}$ in general formulae (II) and (III).

It is preferred that said group is attached to $R_1$, $R_2$, $R_3$, nitrogen atom of the acidic nucleus represented by D and D', or a 5-membered or 6-membered nitrogen-containing heterocyclic ring represented by $Z_1$, $Z_2$ and $Z_3$. It is more preferred that said group is attached to $R_1$, $R_2$, $R_3$ or nitrogen atom of the acidic nucleus represented by D and D'.

In addition to the aforesaid spectral sensitizing dyes, there can be used cyanine dyes, merocyanine dyes, complex merocyanine dyes, etc. in the present invention. Further, complex cyanine dyes, holopolar cyanine dyes, hemicyanine dyes, styryl dyes and hemioxonol dyes can be used. Examples of the cyanine dyes include simple cyanine dye, carbocyanine dye, dicarbocyanine dye and tricarbocyanine dye.

Methine dyes represented by the following general formula (I)″ are illustrated below.

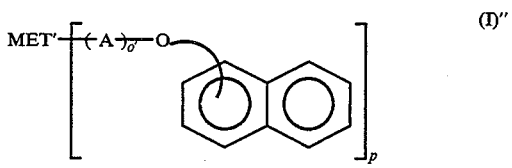

(I)″ wherein A represents methylene group; O' represents 1, 2, 3, 4 or 5; p represents 1 or 2; oxygen atom is attached to the 1- or 2-position of naphthalene ring which may optionally have one or more substituent groups; MET' represents a heptamethinecyanine structure; and methylene group is attached to nitrogen atom of the basic nucleus of MET'.

The cyanine dyes are illustrated in more detail below.

Preferably, A is methylene group or a substituted methylene group [examples of substituent groups include a substituted or unsubstituted alkyl group (e.g., methyl group, 2-carboxyethyl group), a substituted or unsubstituted aryl group (e.g., phenyl group, o-carboxyphenyl group), carboxyl group, a halogen atom (e.g., chlorine atom) and an alkoxy group (e.g., methoxy group) with unsubstituted methylene group being more preferred.

Naphthalene ring may be substituted. Concrete examples of substituent groups for naphthalene ring include a halogen atom (e.g., chlorine atom, fluorine atom, bromine atom), an unsubstituted alkyl group having preferably not more than 6 carbon atoms (e.g., methyl group, ethyl group), a substituted alkyl group having preferably not more than 11 carbon atoms (e.g., benzyl group, α-naphthylmethyl group, 2-phenylethyl group, trifluoromethyl group), an acyl group having preferably not more than 10 carbon atoms (e.g., acetyl group, benzoyl group, mesyl group), an acyloxy group having preferably not more than 10 carbon atoms (e.g., acetoxy group), an alkoxycarbonyl group having preferably not more than 10 carbon atoms (e.g., methoxycarbonyl group, ethoxycarbonyl group, benzyloxycarbonyl group), a substituted or unsubstituted carbamoyl group (e.g., carbamoyl group, N,N-dimethylcarbamoyl group, morpholinocarbonyl group, piperidinocarbonyl group), a substituted or unsubstituted sulfamoyl group (e.g., sulfamoyl group, N,N-dimethylsulfamoyl group, morpholinosulfonyl group, piperidinosulfonyl group), carboxy group, cyano group, hydroxyl group, an amino group, an acylamino group having preferably not more than 8 carbon atoms (e.g., acetylamino group), an alkoxy group having preferably not more than 10 carbon atoms (e.g., methoxy group, ethoxy group, benzyloxy group) and an aryl group (e.g., phenyl group, tolyl group).

Typical examples of polymethine dyes represented by general formulas (I) and (I)″ include, but are not limited to, the following compounds.

(A) Polymethine dyes having an oxidation potential ($E_{ox}(V_{vs}SCE)$) of higher than 0.60 ($V_{vs}SCE$).

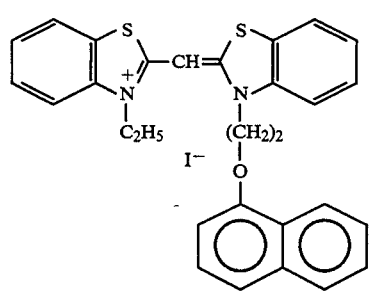
(1)
$E_{ox} = 1.33$
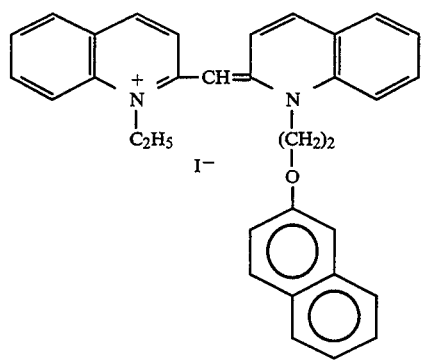
(2)
$E_{ox} = 1.067$
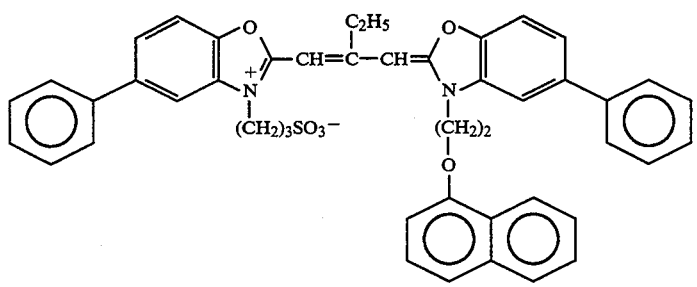
(3)
$E_{ox} = 0.99$
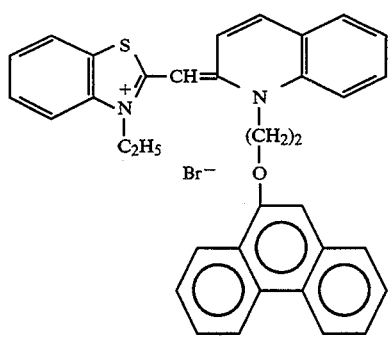
(4)
$E_{ox} = 1.173$
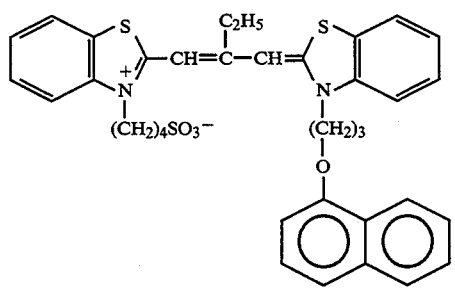
(5)
$E_{ox} = 0.862$

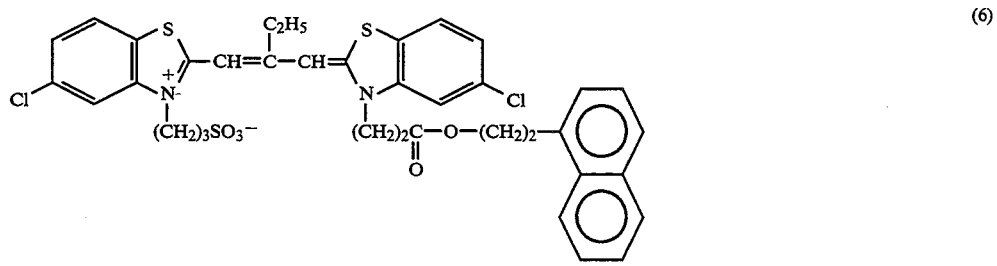
$E_{ox} = 0.936$ (6)
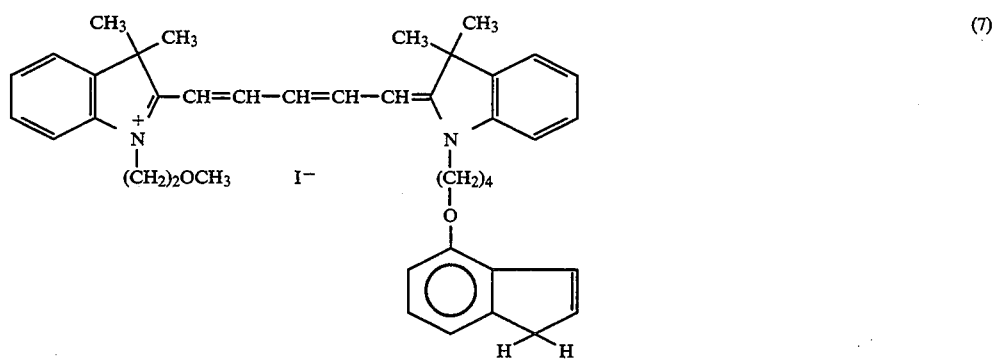
$E_{ox} = 0.735$ (7)
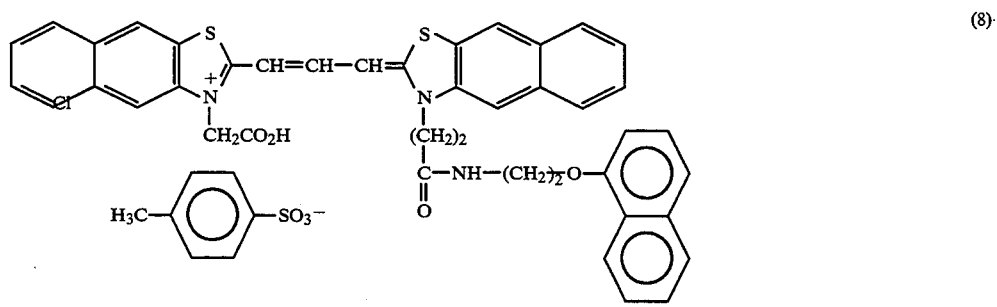
$E_{ox} = 0.985$ (8)
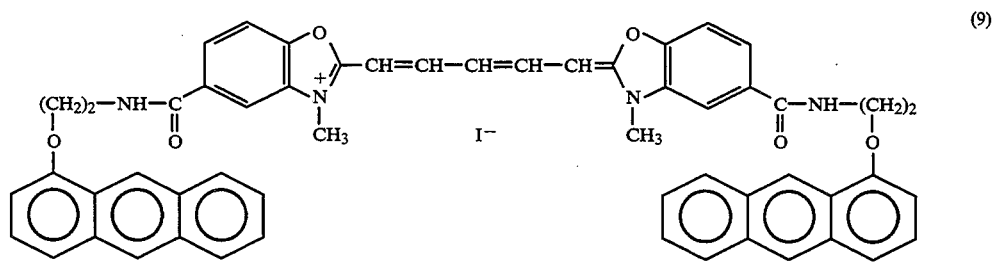
$E_{ox} = 0.657$ (9)

(10)
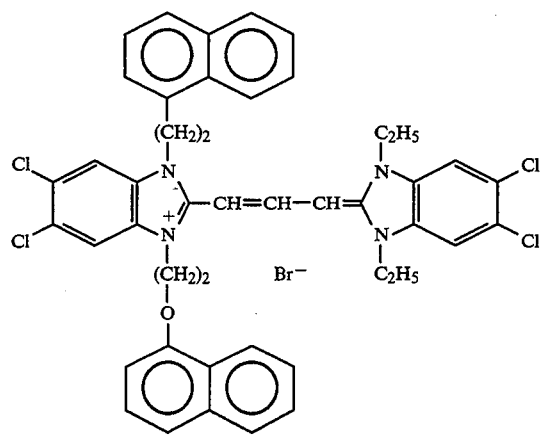
$E_{ox} = 0.622$
(11)
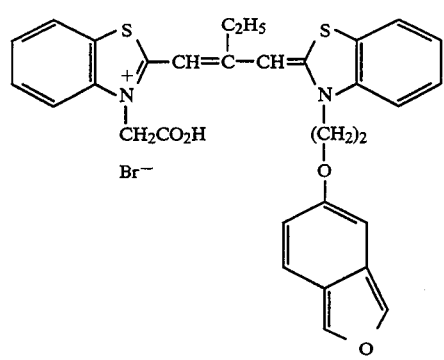
$E_{ox} = 0.863$
(12)
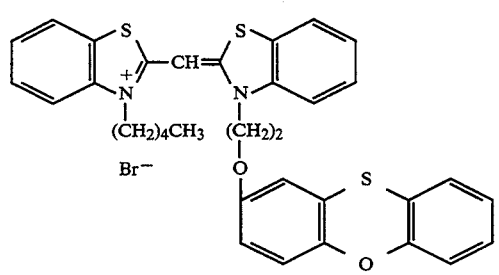
$E_{ox} = 1.32$
(B) Polymethine dyes having an oxidation potential ($E_{ox}(V_{vs}SCE)$) of 0.60 or lower.
(13)
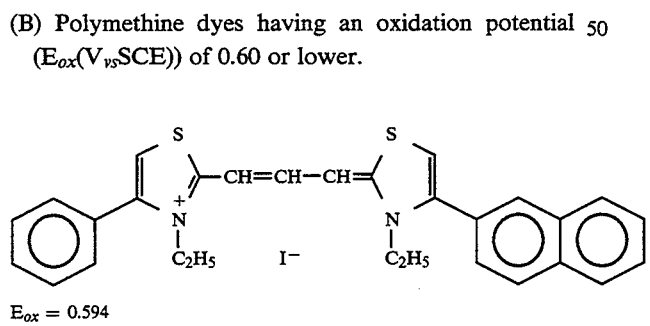
$E_{ox} = 0.594$ -continued
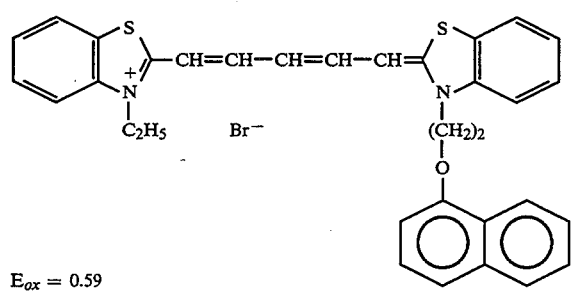 (14)
$E_{ox}$ = 0.59
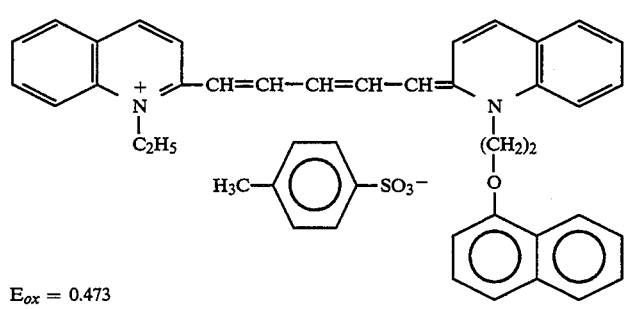 (15)
$E_{ox}$ = 0.473
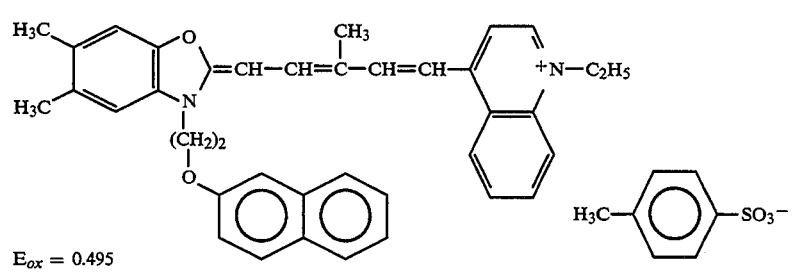 (16)
$E_{ox}$ = 0.495
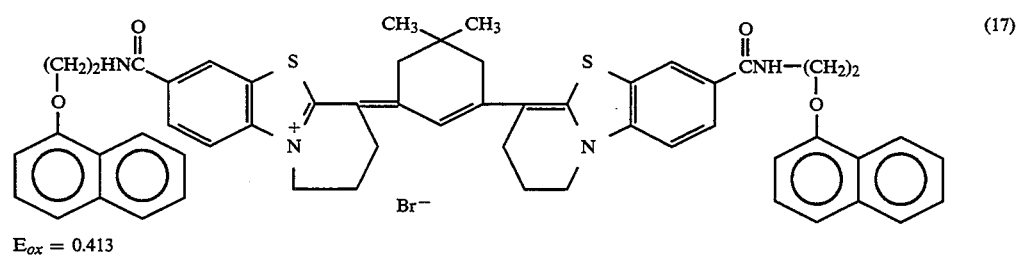 (17)
$E_{ox}$ = 0.413
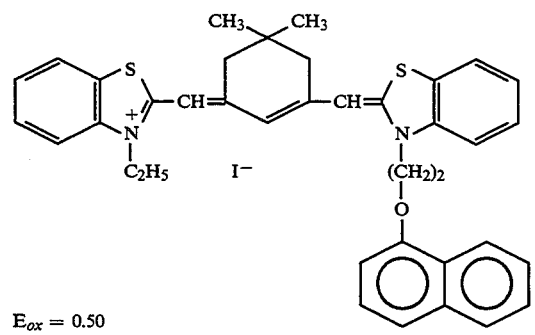 (18)
$E_{ox}$ = 0.50

(19)
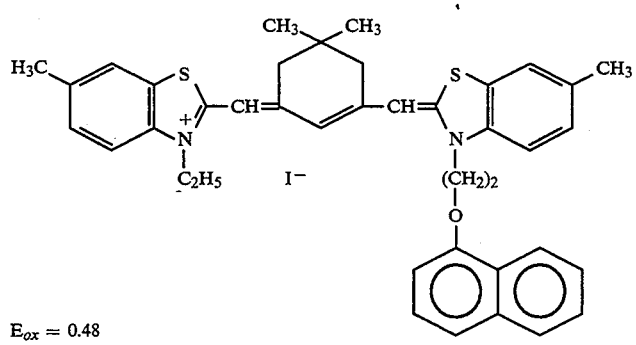
$E_{ox} = 0.48$
(20)
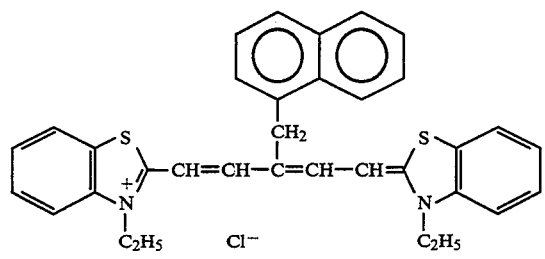
$E_{ox} = 0.573$
(21)
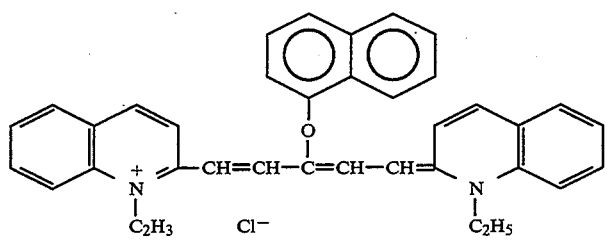
$E_{ox} = 0.408$
(22)
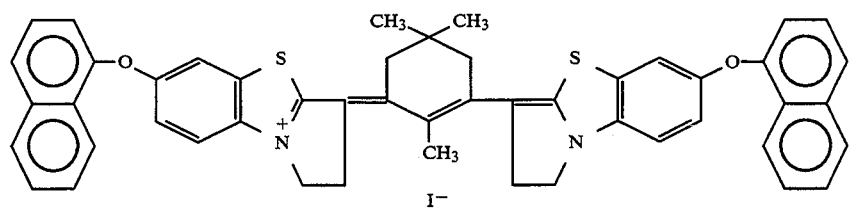
$E_{ox} = 0.380$
(23)
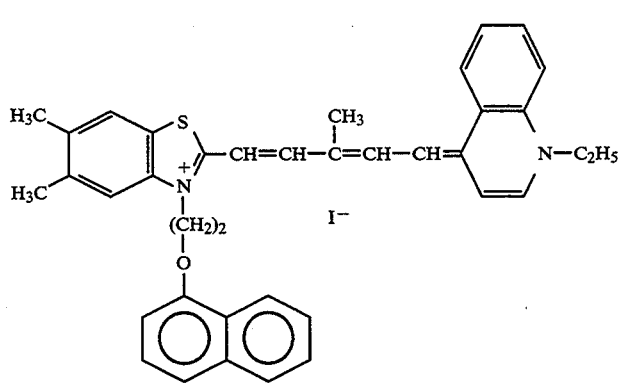
$E_{ox} = 0.40$

(24)
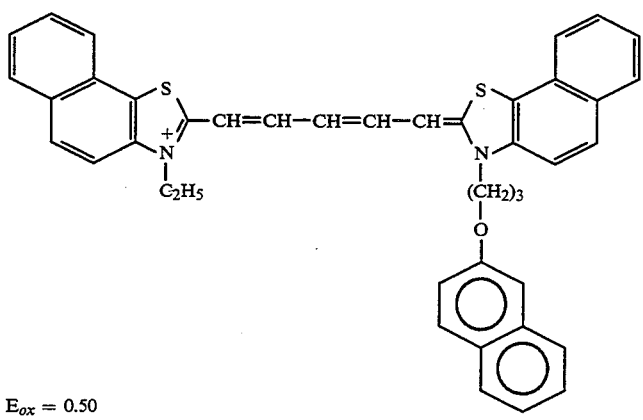
$E_{ox} = 0.50$
(25)
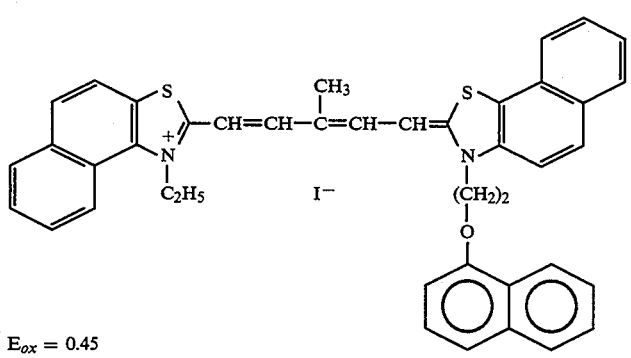
$E_{ox} = 0.45$
(26)
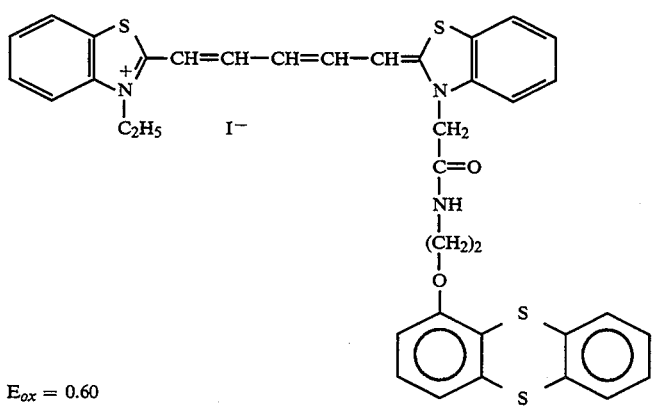
$E_{ox} = 0.60$
(27)
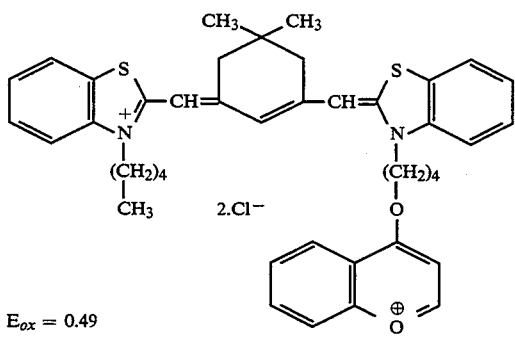
$E_{ox} = 0.49$
Dyes having heptamethinecyanine structure

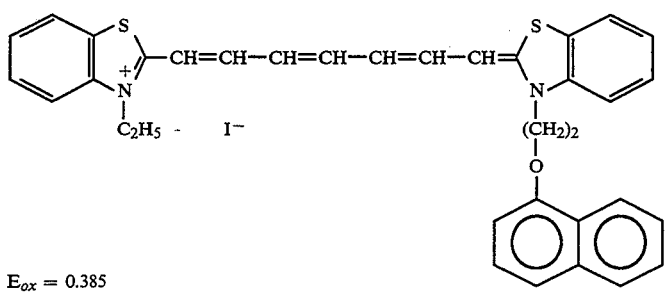
(28)
$E_{ox} = 0.385$
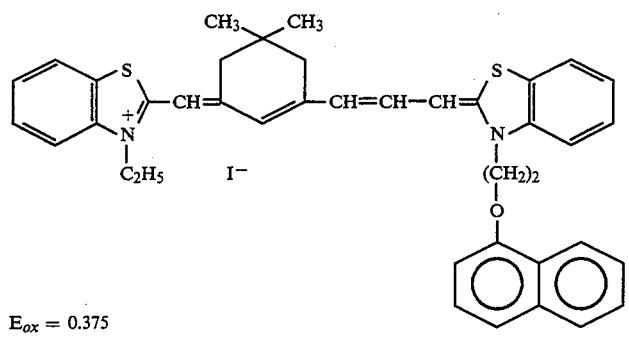
(29)
$E_{ox} = 0.375$
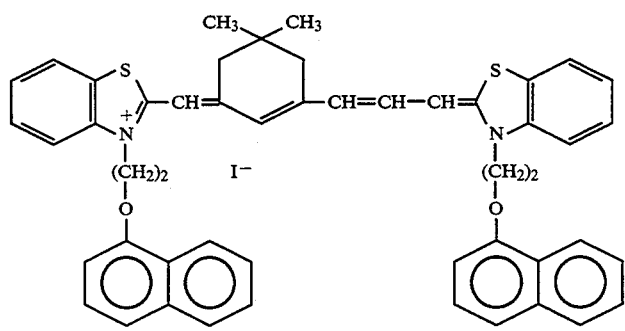
(30)
$E_{ox} = 0.374$
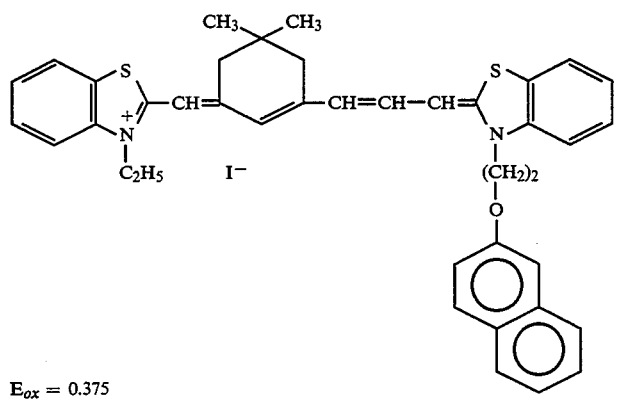
(31)
$E_{ox} = 0.375$ -continued
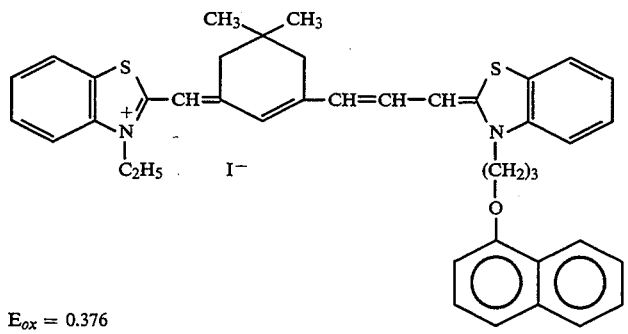
(32)
$E_{ox} = 0.376$
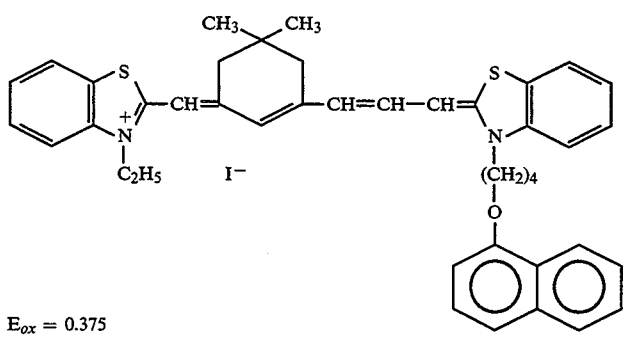
(33)
$E_{ox} = 0.375$
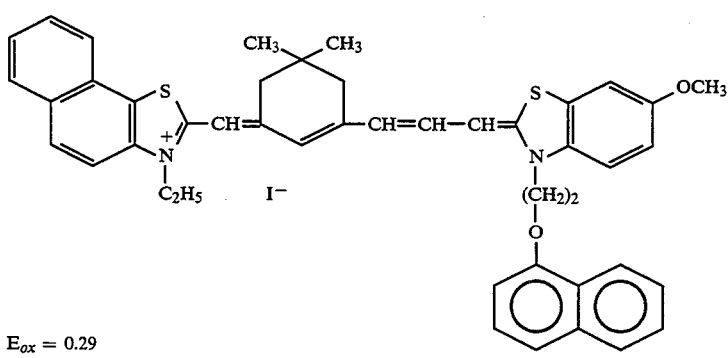
(34)
$E_{ox} = 0.29$
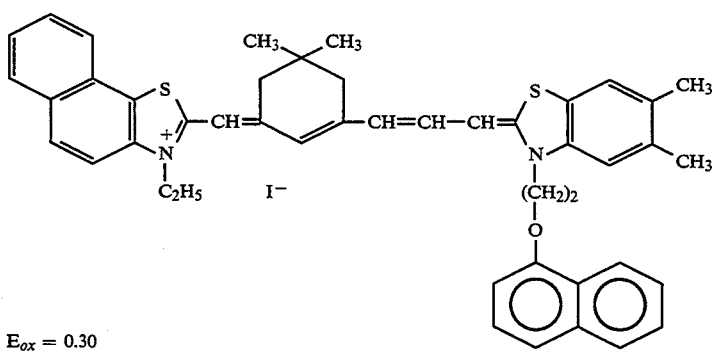
(35)
$E_{ox} = 0.30$

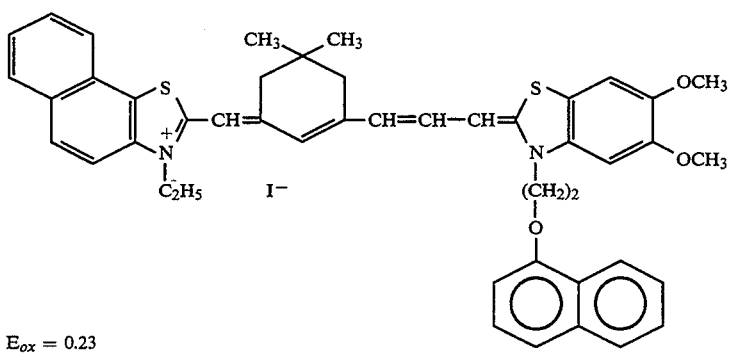
(36)
$E_{ox} = 0.23$
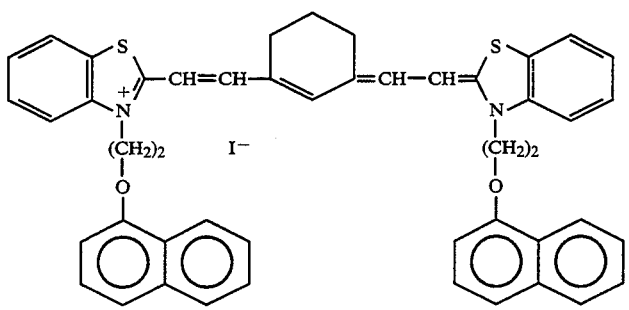
(37)
$E_{ox} = 0.295$
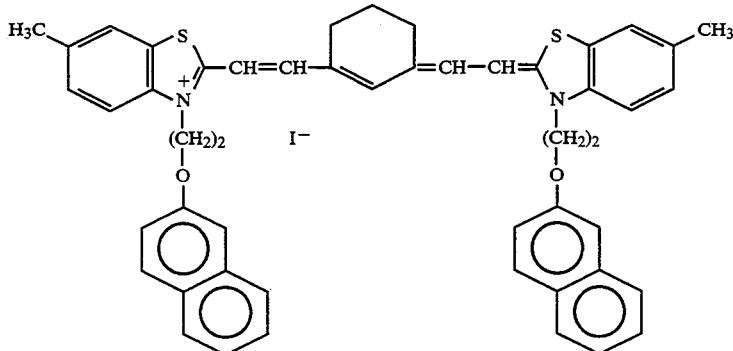
(38)
$E_{ox} = 0.275$
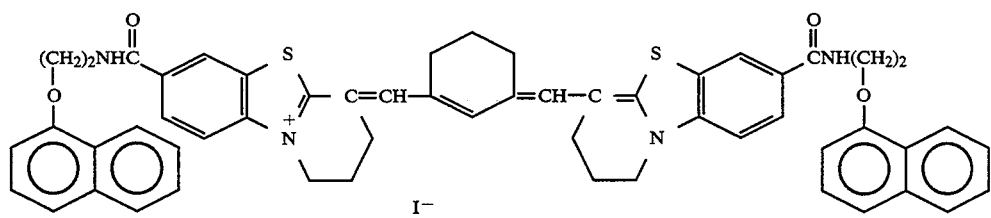
(39)
$E_{ox} = 0.18$
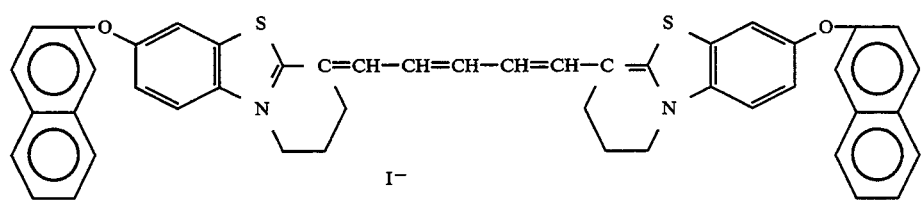
(40)
$E_{ox} = 0.255$ -continued
(41)
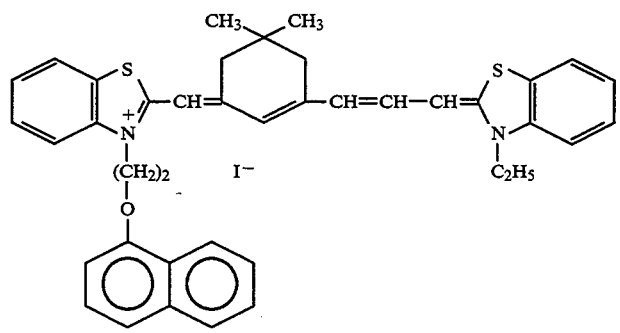
$E_{ox} = 0.374$
(42)
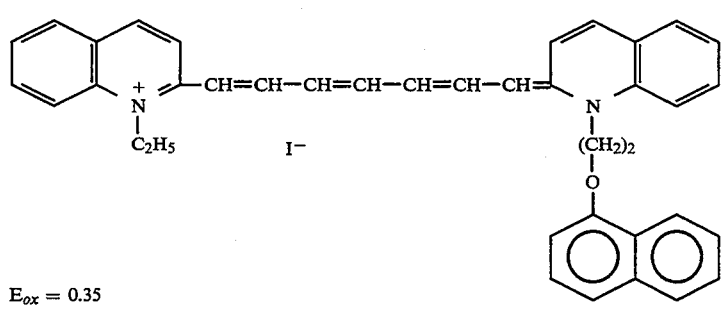
$E_{ox} = 0.35$
(43)
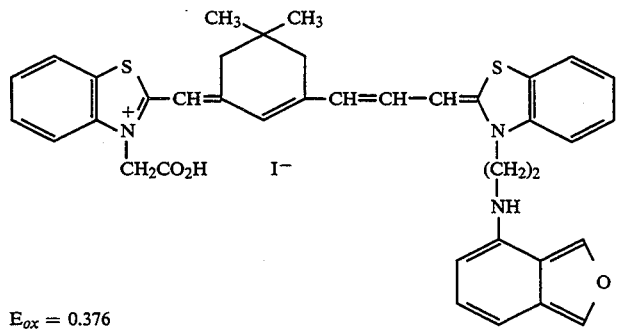
$E_{ox} = 0.376$
(44)
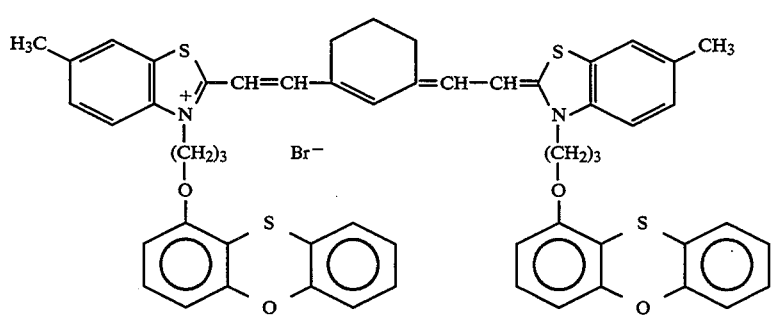
$E_{ox} = 0.274$
Dyes having hexamethine merocyanine structure

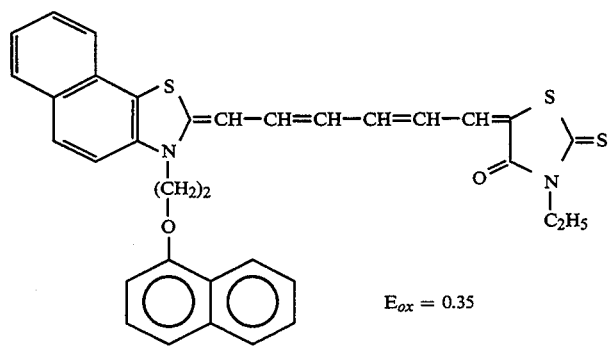
(45)
$E_{ox} = 0.35$
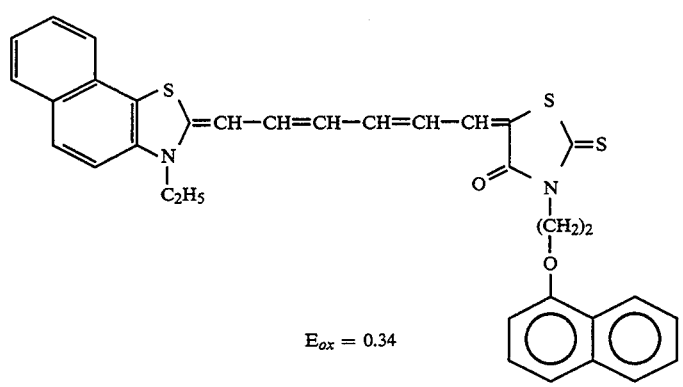
(46)
$E_{ox} = 0.34$
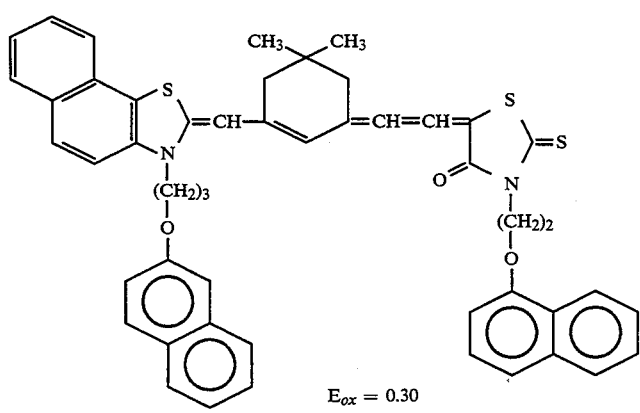
(47)
$E_{ox} = 0.30$
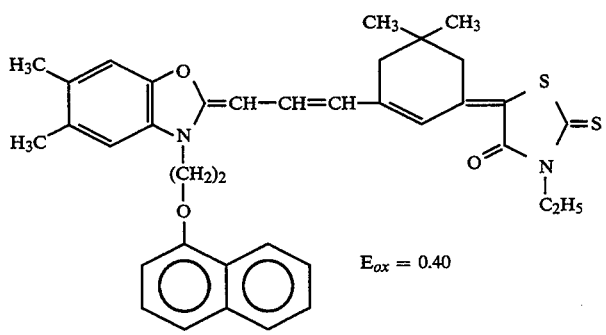
(48)
$E_{ox} = 0.40$

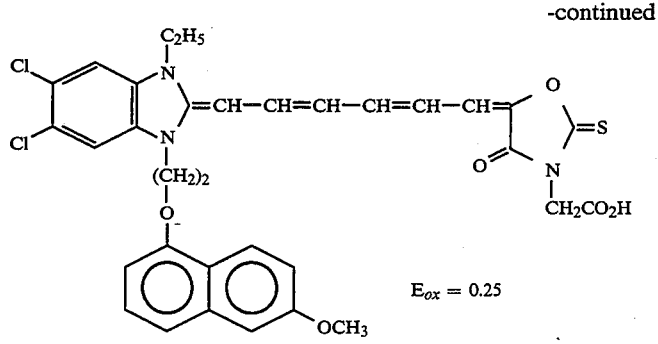

(49)

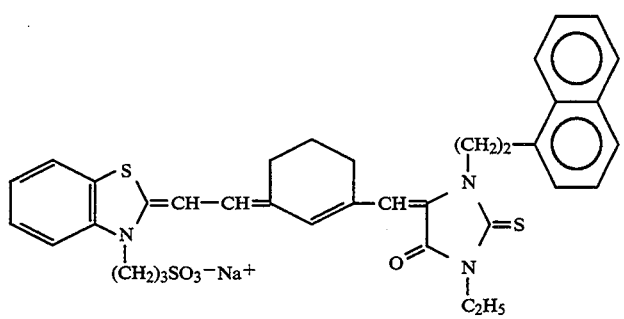

(50)

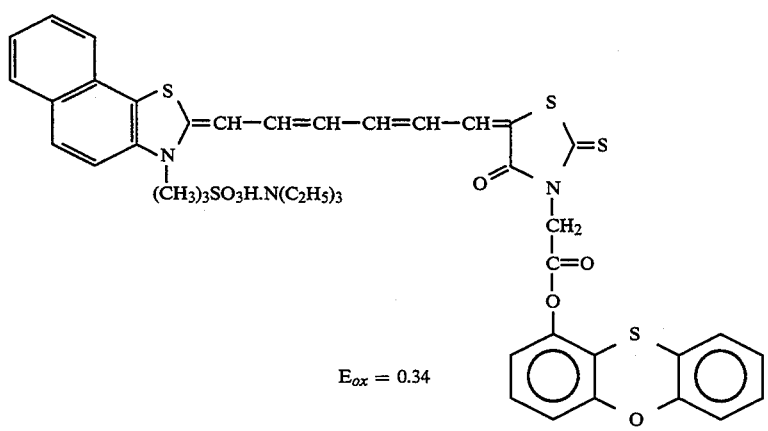

(51)

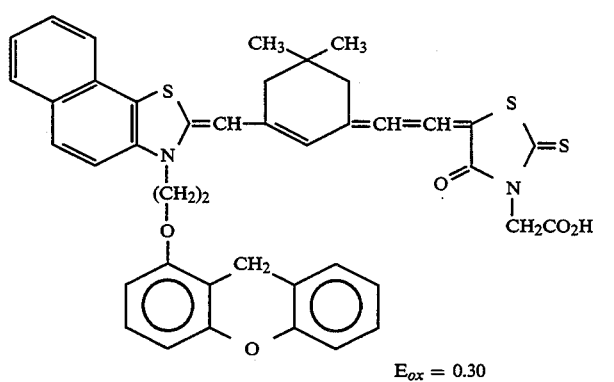

(52)

Polymethine dyes represented by general formula (I) which are used in the present invention can be synthesized according to the methods described in the following literature.

(a) F. M. Hamer, *Heterocyclic Compounds—Cyanine Dyes and Related Compounds*—(John Wiley & Sons, New York, London, 1964).

(b) D. M. Sturmer, *Heterocyclic Compounds—Special Topics in Heterocyclic Chemistry*—, Chapter 8, Paragraph 4, pages 482–515 (John Wiley & Sons, New York, London, 1977).

(c) *Zh. Org. Khim.*, Vol. 17, No. 1, pages 167–169 (1981), Vol. 15, No. 2, pages 400–407 (1979), Vol. 14, No. 10, pages 2214–2221 (1978), Vol. 13, No.

11, pages 2440–2443 (1977), Vol. 19, No. 10, pages 2134–2142 (1983); *Ukr. Khim. Zh.,* Vol. 40, No. 6, pages 625–629 (1974); *Khim. Geterotski, Soedin.,* No. 2, pages 175–178, Russian Patents 420643 and 341823, JP-A-59-217761 (the term "JP-A" as used herein means an "unexamined published Japanese patent application"), U.S. Pat. Nos. 4,334,000, 3,671,648, 3,623,881 and 3,573,921, European Patents 288261A1, 102781A2 and 102781A2 and JP-B-49-46930 (the term "JP-B" as used herein means an "examined Japanese patent publication").

The ether linkage forming reaction or amido linkage forming reaction of the $-(Q)_{n2}Ar$ moiety can be carried out by utilizing conventional methods for linkage forming reactions such as ester linkage forming reaction known in organic chemistry. Namely, there can be used any of a method wherein MET is bonded to the polycyclic moiety represented by Ar, a method wherein a starting material for synthesizing polymethine dye and an intermediate are bonded to the polycyclic moiety represented by Ar and a dye forming reaction is then carried out and a method wherein a starting material for synthesizing the polycyclic moiety represented by Ar and an intermediate are bonded to the polymethine dye moiety and the polycyclic moiety represented by Ar is then synthesized. These linkages can be synthesized by properly choosing appropriate methods from among them. Synthesis reactions for forming these linkages can be carried by reference to the literature for organic synthesis reactions, such as *New Experimental Chemistry Lecture 14—Synthesis and Reaction of Organic Compound,* Vol. I–V, edited by Nippon Kagaku Kai (published by Maruzen, Tokyo, 1977) (written in Japanese), *Essay on Organic Reaction,* written by Yoshiro Ogata (published by Maruzen, Tokyo, 1962) (written in Japanese), L. F. Fieser and M. Fieser, *Advanced Organic Chemistry* (published by Maruzen, Tokyo, 1962), etc.

The sensitizing dyes of the present invention in an amount of $5 \times 10^{-7}$ to $5 \times 10^{-3}$ mol, preferably $1 \times 10^{-6}$ to $1 \times 10^{-3}$ mol, particularly preferably $2 \times 10^{-6}$ to $5 \times 10^{-4}$ mol per mol of silver halide are incorporated in silver halide photographic emulsions.

The sensitizing dyes for use in the present invention can be directly dispersed in the emulsions. For example, the sensitizing dyes are dissolved in an appropriate solvent such as methyl alcohol, ethyl alcohol, methyl cellosolve, acetone, water, pyridine or a mixed solvent thereof and the resulting solutions are added to the emulsions. The dyes can be dissolved by using ultrasonic wave. Further, the infrared sensitizing dyes can be added by a method wherein the dyes are dissolved in volatile organic solvents, the resulting solutions are dispersed in hydrophilic colloid and the resulting dispersions are added to the emulsions as described in U.S. Pat. No. 3,469,987; a method wherein water-insoluble dyes are dispersed in water-soluble solvents without dissolving said dyes, and the resulting dispersions are added to the emulsions as described in JP-B-46-24185; a method wherein the dyes are dissolved in surfactants and the resulting solutions are added to the emulsions as described in U.S. Pat. No. 3,822,135; a method wherein the dyes are dissolved by using compounds causing red shift and the resulting solutions are added to the emulsions as described in JP-A-51-74624; a method wherein the dyes are dissolved in an acid substantially free from water and the resulting solutions are added to the emulsions as described in JP-A-50-80826; etc. In addition thereto, the dyes can be added to the emulsions by using methods described in U.S. Pat. Nos. 2,912,343, 3,342,605, 2,996,287, 3,429,835, etc. Further, the infrared sensitizing dyes may be uniformly dispersed in silver halide emulsions before coating on a support. It is preferred that the dyes are added before chemical sensitization or at the stage of the latter half of the formation of silver halide grains.

Among the red to infrared sensitizing dyes of the polymethine dyes of the present invention, supersensitization with compounds represented by the following general formula (IV), (V), (VI), (VII), (VIIIa), (VIIIb) or (VIIIc) in particular is useful for M band type sensitization.

When the supersensitizing agents represented by the following general formula (IV) are used in combination with the supersensitizing agents represented by the following general formula (V), (VI), (VII), (VIIIa), (VIIIb) or (VIIIc), the supersensitization effect thereof can be greatly enhanced.

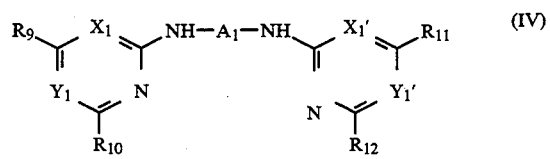

In the above formula, $A_1$ represents a bivalent aromatic residue; $R_9$, $R_{10}$, $R_{11}$ and $R_{12}$ represent each hydrogen atom, hydroxyl group, an alkyl group, an alkoxy group, an aryloxy group, a halogen atom, a heterocyclic nucleus, a heterocyclic thio group, an arylthio group, an amino group, an alkylamino group, an arylamino group, an aralkylamino group, an aryl group or a mercapto group, each of which may optionally have one or more substituent groups, with the proviso that at least one of $A_1$, $R_9$, $R_{10}$, $R_{11}$ and $R_{12}$ is a group having sulfo group; $X_1$, $Y_1$, $X_1'$ and $Y_1'$ represent each $-CH=$ or $-N=$ and at least one of $X_1$ and $Y_1$ and at least one of $X_1'$ and $Y_1'$ are $-N=$.

In general formula (IV), more specifically $-A_1-$ represents a bivalent aromatic residue which may be substituted by $-SO_3M$ group [wherein M is hydrogen atom or a cation which impart water-solubility (e.g., sodium, potassium)].

Useful $-A_1-$ group is chosen from among the following $-A_2-$ and $-A_3-$ groups, and when $R_9$, $R_{10}$, $R_{11}$ or $R_{12}$ does not have $-SO_3M$ group, $-A_1-$ group is chosen from among the $-A_2-$ group.

$-A_2-$;

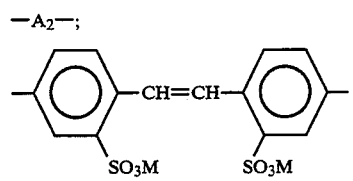

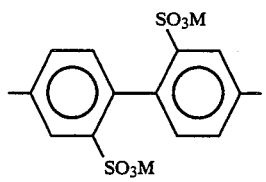
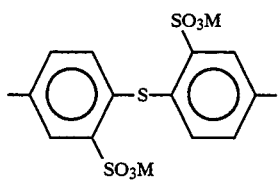
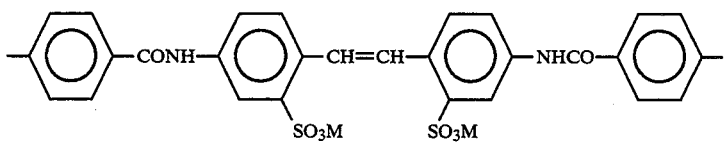
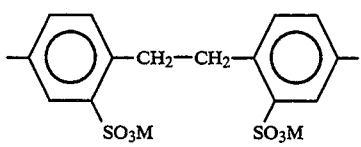
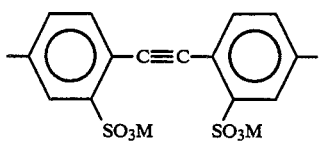
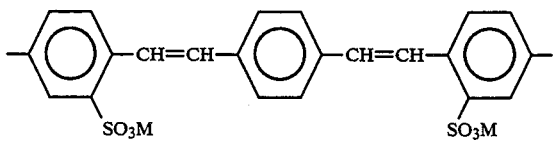
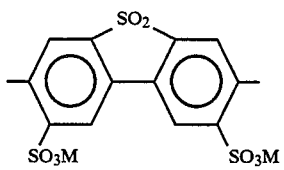
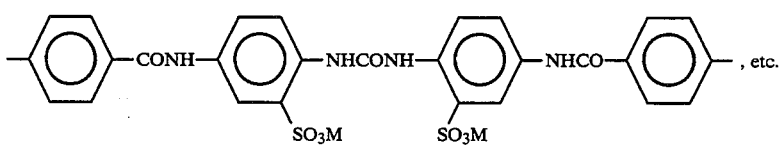, etc.
In the above formulae, M is hydrogen atom or a cation which imparts water-solubility.
—A$_3$—;
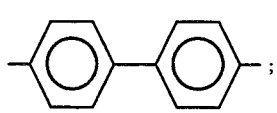; 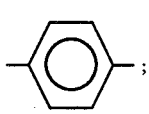;
-continued
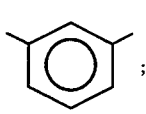; 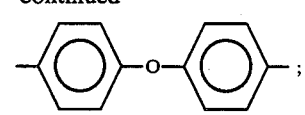;

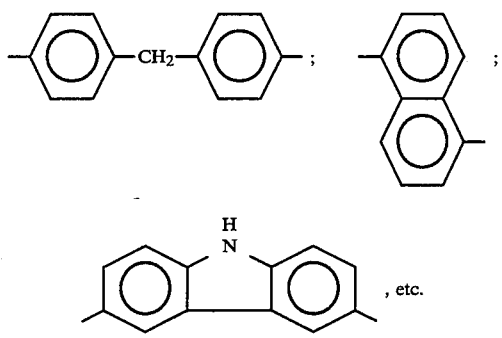
, etc.

$R_9$, $R_{10}$, $R_{11}$ and $R_{12}$ represents each hydrogen atom, hydroxyl group, an alkyl group (having preferably 1 to 8 carbon atoms, such as methyl, ethyl, n-propyl, n-butyl), an alkoxy group (having preferably 1 to 8 carbon atoms, such as methoxy, ethoxy, propoxy, butoxy), an aryloxy group (e.g., phenoxy, naphthoxy, o-tolyloxy, p-sulfophenoxy), a halogen atom (e.g., chlorine, bromine), a heterocyclic nucleus (e.g., morpholinyl, piperidyl), an alkylthio group (e.g., methylthio, ethylthio), a heterocyclic thio group (e.g., benzthiazolylthio, benzimidazolylthio, phenyltetrazolylthio), an arylthio group (e.g., phenylthio, tolylthio), an amino group, an alkylamino group or a substituted alkylamino group (e.g., methylamino, ethylamino, propylamino, dimethylamino, diethylamino, dodecylamino, cyclohexylamino, β-hydroxyethylamino, di-(β-hydroxyethyl)amino, β-sulfoethylamino), an arylamino group or a substituted arylamino group (e.g., anilino, o-sulfoanilino, m-sulfoanilino, p-sulfoanilino, o-toluidino, m-toluidino, p-toluidino, o-carboxyanilino, m-carboxyanilino, p-carboxyanilino, o-chloroanilino, m-chloroanilino, p-chloroanilino, p-aminoanilino, o-anisidino, m-anisidino, p-anisidino, o-acetaminoanilino, hydroxyanilino, disulfophenylamino, naphthylamino, sulfonaphthylamino), a heterocyclic amino group (e.g., 2-benzthiazolylamino, 2-pyridylamino), a substituted or unsubstituted aralkylamino group (e.g., benzylamino, o-anisylamino, m-anisylamino, p-anisylamino), an aryl group (e.g., phenyl) or a mercapto group.

$R_9$, $R_{10}$, $R_{11}$ and $R_{12}$ may be the same or different groups. When the —$A_1$— group is a member selected from the —$A_2$— group, at least one of $R_9$, $R_{10}$, $R_{11}$ and $R_{12}$ must be a group having sulfo group (in the free form or in the form of a salt). $X_1$, $Y_1$, $X_1'$ and $Y_1'$ are each —CH= or —N=, and it is preferred that $X_1$ and $X_1'$ are —CH= and $Y_1$ and $Y_1'$ are —N=.

Examples of the compounds of general formula (IV) which can be used in the present invention include, but are not limited to, the following compounds.

(IV-1) Disodium salt of 4,4'-bis[2,6-di(2-naphthoxy)-pyrimidine-4-ylamino]stilbene-2,2'-disulfonic acid (IV-2) Disodium salt of 4,4'-bis[2,6-di(2-naphthylamino)pyrimidine-4-ylamino]stilbene-2,2'-disulfonic acid (IV-3) Disodium salt of 4,4'-bis[2,6-dianilinopyrimidine-4-ylamino]stilbene-2,2'-disulfonic acid (IV-4) Disodium salt of 4,4'-bis[2-(2-naphthylamino)-6-anilinopyrimidine-4-ylamino]stilbene-2,2'-disulfonic acid (IV-5) 4,4'-Bis[2,6-diphenoxypyrimidine-4-ylamino]-stilbene-2,2'-disulfonic acid ditriethylammonium salt (IV-6) Disodium salt of 4,4'-bis[2,6-di(benzimidazolyl-2-thio)pyrimidine-4-ylamino]stilbene-2,2'-disulfonic acid (IV-7) Disodium salt of 4,4'-bis[4,6-di(benzthiazolyl-2-thio)pyrimidine-2-ylamino]stilbene-2,2'-disulfonic acid (IV-8) Disodium salt of 4,4'-bis[4,6-di(benzthiazolyl-2-amino)pyrimidine-2-ylamino]stilbene-2,2'-disulfonic acid (IV-9) Disodium salt of 4,4'-bis[4,5-di(naphthyl-2-oxy)-pyrimidine-2-ylamino]stilbene-2,2'-disulfonic acid (IV-10) Disodium salt of 4,4'-bis(4,6-diphenoxypyrimidine-2-ylamino)stilbene-2,2'-disulfonic acid (IV-11) Disodium salt of 4,4'-bis(4,6-diphenylthiopyrimidine-2-ylamino)stilbene-2,2'-disulfonic acid (IV-12) Disodium salt of 4,4'-bis(4,6-dimercaptopyrimidine-2-ylamino)biphenyl-2,2'-disulfonic acid (IV-13) Disodium salt of 4,4'-bis[4,6-dianilinotriazine-2-ylamino]stilbene-2,2'-disulfonic acid (IV-14) Disodium salt of 4,4'-bis(4-anilino-6-hydroxy-triazine-2-ylamino)stilbene-2,2'-disulfonic acid (IV-15) Disodium salt of 4,4'-bis[4,6-di(naphthyl-2-oxy)pyrimidine-2-ylamino]bibenzyl-2,2'-disulfonic acid (IV-16) Disodium salt of 4,4'-bis(4,6-dianilinopyrimidine-2-ylamino)stilbene-2,2'-disulfonic acid (IV-17) Disodium salt of 4,4'-bis[4-chloro-6-(2-naphthyloxy)pyrimidine-2-ylamino]biphenyl-2,2'-disulfonic acid (IV-18) Disodium salt of 4,4'-bis[4,6-di(1-phenyltetrazolyl-5-thio)pyrimidine-2-ylamino]stilbene-2,2'-disulfonic acid (IV-19) Disodium salt of 4,4'-bis[4,6-di(benzimidazolyl-2-thio)pyrimidine-2-ylamino]stilbene-2,2'-disulfonic acid (IV-20) Disodium salt of 4,4'-bis(4-naphthylamino-6-anilinotriazine-2-ylamino)stilbene-2,2'-disulfonic acid Among them, the compounds of formulae (IV-1) to (IV-6) are preferred. The compounds of (IV-1), (IV-2), (IV-4), (IV-5), (IV-9), (IV-15) and (IV-20) are particularly preferred.

The compounds represented by general formula (IV) are used in an amount of 0.01 to 5 g per mol of silver halide and advantageously in a ratio by weight of said compound to the sensitizing dye of from 1/1 to 100/1, preferably from 2/1 to 50/1. It is preferred that said compounds of general formula (IV) are used in combination with the compounds of the following general formula (V).

The compounds represented by the following general formula (V) are illustrated below.

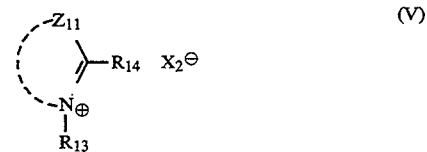

In the above formula, $Z_{11}$ represents a nonmetallic atomic group required for forming a 5-membered or 6-membered nitrogen-containing heterocyclic ring. The ring may be condensed with benzene ring or naphthalene ring. Examples of the ring include thiazoliums (e.g., thiazolium, 4-methylthiazolium, benzthiazolium, 5-methylbenzthiazolium, 5-chlorobenzthiazolium, 5-methoxybenzthiazolium, 6-methylbenzthiazolium, 6- methoxybenzthiazolium, naphtho[1,2-d]thiazolium, naphtho[2,1-d]thiazolium), oxazoliums (e.g., oxazolium, 4-methyloxazolium, benzoxazolium, 5-chlorobenzoxazolium, 5-phenylbenzoxazolium, 5-methylbenzoxazolium, naphtho[1,2-d]oxazolium), imidazoliums (e.g., 1-methylbenzimidazolium, 1-propyl-5-chlorobenzimidazolium, 1-ethyl-5,6-dichlorobenzimidazolium, 1-allyl-5-trifluoromethyl-6-chlorobenzimidazolium) and selenazoliums (e.g., benzoselenazolium, 5-chlorobenzoselenazolium, 5-methoxybenzoselenazolium, 5-methylbenzoselenazolium, naphtho[1,2-d]selenazolium).

$R_{13}$ represents hydrogen atom, an alkyl group (having preferably not more than 8 carbon atoms, e.g., methyl, ethyl, propyl, butyl, pentyl) or an alkenyl group (e.g., allyl group). $R_{14}$ represents hydrogen atom or a lower alkyl group (e.g., methyl, ethyl). $R_{13}$ and $R_{14}$ each may be a substituted alkyl group. $X_2^{\ominus}$ represents an acid anion (e.g., Cl$^-$, Br$^-$, I$^-$, ClO$_4^-$). Among the groups represented by $Z_{11}$, thiazoliums are preferred. Substituted or unsubstituted benzthiazoliums or naphthothiazoliums are more preferred. These groups may be optionally substituted.

Examples of the compounds represented by general formula (V) include, but are not limited to, the following compounds.

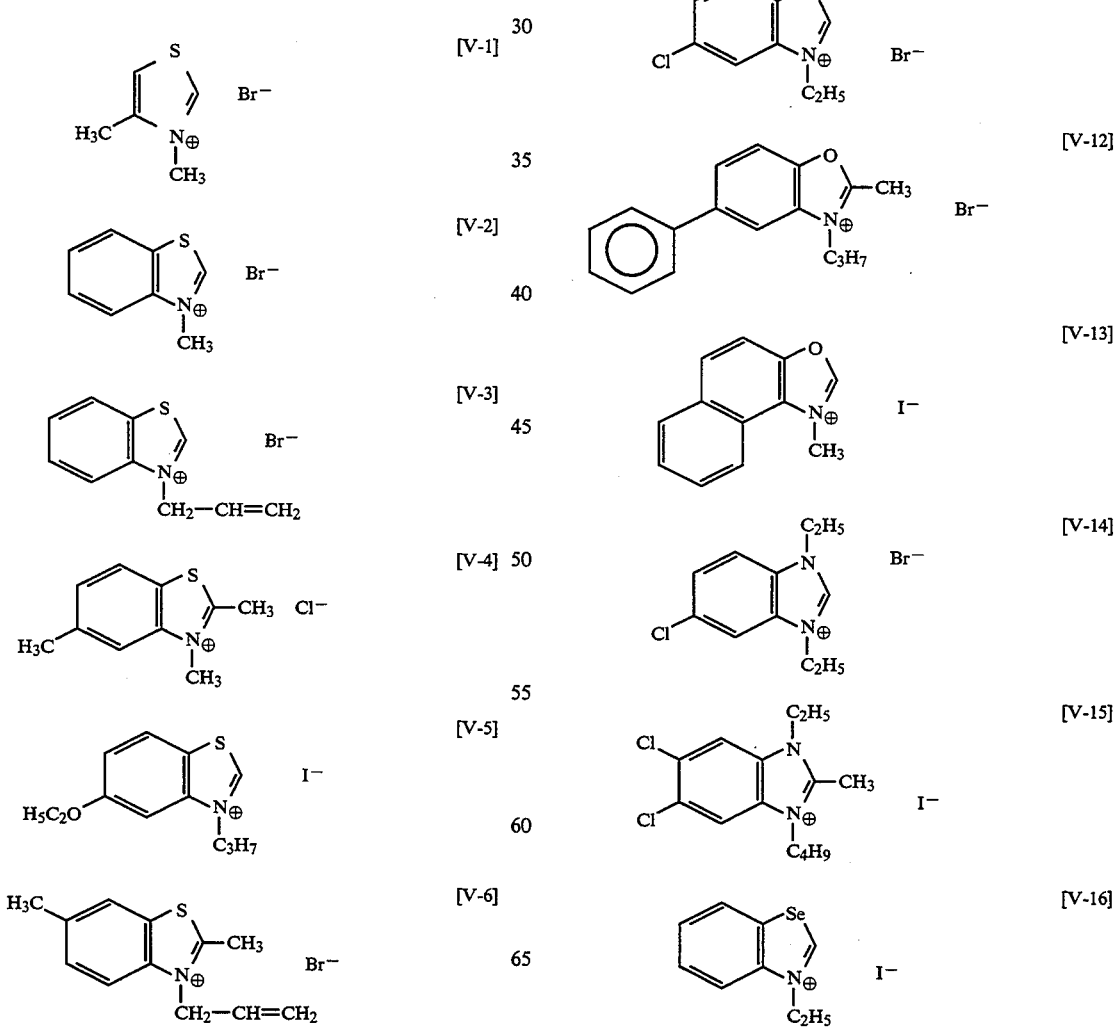

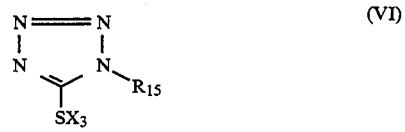

[V-17]

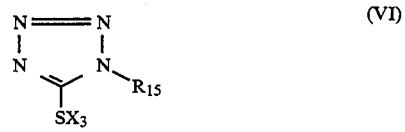

[V-18]

The compounds represented by general formula (V) according to the present invention are used in an amount of preferably about 0.01 to 5 g per mol of silver halide in the emulsion.

The polymethine dye of general formula (I) and the compound of general formula (V) are used in a ratio by weight of the dye of general formula (I) to the compound of general formula (V) of preferably from 1/1 to 1/300, particularly preferably from ½ to 1/50.

The compounds represented by general formula (V) according to the present invention can be directly dispersed in the emulsions. The compounds may be dissolved in an appropriate solvent (e.g., water, methyl alcohol, ethyl alcohol, propanol, methyl cellosolve, acetone) or a solvent mixture of two or more of them, and the resulting solution may be added to the emulsions. Alternatively, the compounds in the form of a dispersion in a solution or colloid can be added to the emulsions according to the methods for the addition of sensitizing dyes.

The compounds of general formula (V) may be added to the emulsions before or after the sensitizing dyes of general formula (I) are added. The compounds of general formula (V) and the sensitizing dyes of general formula (I) may be separately dissolved and the resulting solutions may be simultaneously added to the emulsions. Alternatively, after the solutions were mixed, the mixture may be added to the emulsions.

It is preferred that a combination of the infrared sensitizing dye of general formula (I) and the compound of general formula (V) according to the present invention is used together with the compound of general formula (IV).

When the supersensitizing agent of general formula (IV) or (V) together with a heterocyclic mercapto compound is used in the infrared-sensitized high silver chloride emulsion of the present invention, latent image is stabilized and the linear development dependence of gradation is remarkably improved in addition to high sensitization and the inhibition of fogging.

Examples of the heterocyclic mercapto compound include heterocyclic compounds which have thiazole ring, oxazole ring, oxazine ring, thiazole ring, thiazoline ring, selenazole ring, imidazole ring, indoline ring, pyrrolidine ring, tetrazole ring, thiadiazole ring, quinoline ring or oxadiazole ring and is substituted by mercapto group. Compounds into which further carboxyl group, sulfo group, a carbamoyl group, a sulfamoyl group or hydroxyl group is introduced, are particularly preferred. The specification of JP-B-43-22883 discloses that heterocyclic mercapto compounds are used as supersensitizing agents. When the heterocyclic mercapto compound is used together with the compound of general formula (V) in the present invention, remarkable fog-inhibiting effect and supersensitization effect can be obtained. Mercapto compounds represented by the following general formulae (VI) and (VII) are particularly preferred.

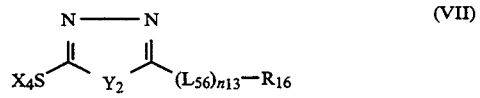

(VI)

In the above formula, $R_{15}$ represents an alkyl group, an alkenyl group or an aryl group; and $X_3$ represents hydrogen atom, an alkali metal atom, ammonium group or a precursor. Examples of the alkali metal atom include sodium atom and potassium atom. Examples of the ammonium group include tetramethylammonium group and trimethylbenzylammonium group. The term "precursor" as used herein refers to a group which forms $X_3$=H or an alkali metal under alkaline conditions. Examples thereof include acetyl group, cyanoethyl group and methanesulfonylethyl group.

The alkyl group and the alkenyl group represented by $R_{15}$ may be unsubstituted or substituted and in the form of an alicyclic group. Examples of substituent groups for the substituted alkyl group include a halogen atom, nitro group, cyano group, hydroxyl group, an alkoxy group, an aryl group, an acylamino group, an alkoxycarbonylamino group, a ureido group, an amino group, a heterocyclic group, an acyl group, a sulfamoyl group, a sulfonamido group, a thioureido group, a carbamoyl group, an alkylthio group, an arylthio group, a heterocyclic thio group, carboxyl group (or a salt) or sulfo group (or a salt). Each of the ureido group, the thioureido group, the sulfamoyl group, the carbamoyl group and the amino group may be unsubstituted, N-alkyl-substituted or N-aryl-substituted. Examples of the aryl group include phenyl group and substituted phenyl group. Examples of substituent groups for phenyl group include an alkyl group and those already described above in the definition of the substituent groups for the alkyl group.

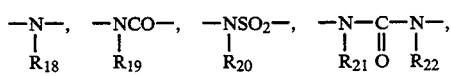

(VII)

In the above formula, $Y_2$ represents oxygen atom, sulfur atom, =NH or =N—$(L_{57})n_{14}$—$R_{17}$; $L_{56}$ and $L_{57}$ represent each a bivalent bonding group; $R_{16}$ and $R_{17}$ represent each hydrogen atom, an alkyl group, an alkenyl group or an aryl group; the alkyl group, the alkenyl group and the aryl group represented by $R_{16}$ and $R_{17}$ have the same meaning as $R_{15}$ in general formula (VI); and $X_4$ has the same meaning as $X_3$ in general formula (VI).

Examples of the bivalent bonding group represented by $L_{56}$ and $L_{57}$ include $$-\underset{R_{18}}{\underset{|}{N}}-,\ -\underset{R_{19}}{\underset{|}{NCO}}-,\ -\underset{R_{20}}{\underset{|}{NSO_2}}-,\ -\underset{R_{21}}{\underset{|}{N}}-\underset{O}{\overset{\|}{C}}-\underset{R_{22}}{\underset{|}{N}}-,$$

-continued $$-N-C-N-, \quad -S-, \quad -CH-, \quad -C-$$
$$\underset{R_{23}}{|} \underset{S}{||} \underset{R_{24}}{|} \qquad \underset{R_{25}}{|} \qquad \underset{R_{26}}{\overset{R_{27}}{|}}$$

or a combination thereof.

In the above formula, $n_{13}$ and $n_{14}$ represent each 0 or 1. $R_{18}$, $R_{19}$, $R_{20}$, $R_{21}$, $R_{22}$, $R_{23}$, $R_{24}$, $R_{25}$ and $R_{26}$ represent each hydrogen atom, an alkyl group or an aralkyl group.

The compounds are incorporated in a layer or layers of the light-sensitive and light-insensitive hydrophilic colloid layers of a silver halide photographic material.

The compounds of general formula (VI) or (VII) are used in an amount of preferably $1 \times 10^{-5}$ to $5 \times 10^{-2}$ mol, more preferably $1 \times 10^{-4}$ to $1 \times 10^{-2}$ mol per mol of silver halide when the compounds are incorporated in the silver halide photographic material. The compounds in an amount of $1 \times 10^{-6}$ to $1 \times 10^{-3}$ mol/l, preferably $5 \times 10^{-6}$ to $5 \times 10^{-4}$ mol/l may be added as anti-fogging agents to color developing solutions.

Examples of the compounds represented by general formulae (VI) and (VII) include, but are not limited to, the following compounds. The compounds described in JP-A-62-269957, pages 4 to 8 can be mentioned, and the following compounds are particularly preferred.

[VII-10]

[Structure: imidazole ring with HS, N-CH₃, and NHCONH-phenyl substituents]

[VII-11]

[Structure: oxadiazole with HS and phenyl substituents]

Further, condensates composed of 2 to 10 condensation units of a substituted or unsubstituted polyhydroxybenzene represented by the following general formula (VIIIa), (VIIIb) or (VIIIc) with formaldehyde are useful as supersensitizing agents for the polymethine dyes of the present invention. The condensates have an effect of preventing latent image from being faded with the passage of time and preventing gradation from being lowered.

(VIIIa)

[Structure: benzene with (OH)$_{n15}$ and COR$_{27}$]

(VIIIb)

[Structure: benzene with (OH)$_{n16}$ and SO$_2$R$_{28}$]

(VIIIc)

[Structure: benzene with OH and R$_{29}$]

In the above formulas R$_{27}$ and R$_{28}$ represent each OH, OM′, OR$_{30}$, NH$_2$, NHR$_{30}$, —N(R$_{30}$)$_2$, —NHNH$_2$ or —NHNHR$_{30}$; R$_{30}$ represents an alkyl group having 1 to 8 carbon atoms, an allyl group or an aralkyl group; M′ represents an alkali metal or an alkaline earth metal; R$_{29}$ represents OH or a halogen atom; n$_{15}$ and n$_{16}$ represent each 1, 2 or 3.

Examples of the substituted or unsubstituted polyhydroxybenzene as the component of the aldehyde condensate used in the present invention include, but are not limited to, the following compounds.

(VIII-1) β-Resorcylic acid
(VIII-2) γ-Resorcylic acid
(VIII-3) 4-Hydroxybenzoic acid hydrazide
(VIII-4) 3,5-Hydroxybenzoic acid hydrazide
(VIII-5) p-Chlorophenol
(VIII-6) Sodium hydroxybenzenesulfonate
(VIII-7) p-Hydroxybenzoic acid
(VIII-8) o-Hydroxybenzoic acid
(VIII-9) m-Hydroxybenzoic acid
(VIII-10) p-Dioxybenzene
(VIII-11) Gallic acid
(VIII-12) Methyl p-hydroxybenzoate
(VIII-13) o-Hydroxybenzenesulfonamide
(VIII-14) N-Ethyl-o-hydroxybenzoic acid amide

[Structure: benzene with OH and CONH(C$_2$H$_5$)]

(VIII-15) N-Diethyl-o-hydroxybenzoic acid amide

[Structure: benzene with OH and CONH(C$_2$H$_5$)]

(VIII-16) o-Hydroxybenzoic acid 2-methylhydrazide

[Structure: benzene with OH and CONHNHCH$_3$ (positions 1 and 2)]

More concretely, the polyhydroxy compounds can be chosen from among the derivatives of compounds represented by general formulae (IIa), (IIb) and (IIc) described in the specification of JP-B-49-49504.

(Silver Halide Emulsion)

Silver halide emulsions which can be used in the present invention may contain any of silver bromide, silver iodobromide, silver iodochlorobromide, silver chlorobromide and silver chloride.

The silver halide grains of the present invention may have regular crystal form such as cube, octahedron, tetradecahedron or rhombic dodecahedron, irregular crystal form such as sphere or plate form or a composite form of these crystal forms. A mixture of grains having various crystal forms may be used.

As the above-described plate-form grains, there are preferred tabular grains having a thickness of 0.5 μm, preferably not larger than 0.3 μm, a diameter of preferably not smaller than 0.6 μm and such a grain size distribution that grains having an average aspect ratio of not lower than 5 account for at least 50% of the entire projected area of the entire grains.

The interior and surface layer of the silver halide grain may be composed of different phases or a uniform phase. There may be used any of grain wherein a latent image is predominantly formed on the surface thereof (e.g., negative type emulsion) and grain wherein a latent image is predominantly formed in the interior thereof (e.g., internal latent image type emulsion).

Silver halide emulsions which can be preferably used in the present invention are illustrated in detail below.

The silver halide emulsions of the present invention, particularly silver halide grains have such a structure that localized phases are provided on the surfaces of the grains, whereby infrared wavelength region is spectral-sensitized, and high sensitivity and stability can be obtained, particularly the excellent stability of latent image can be obtained. Particularly, there can be obtained the stability of the latent image in combination with supersensitization, said stability being acceptable even when high silver chloride emulsion is used. This is a surprising characteristic.

Preferably, the silver halide grains of the present invention have such a halogen composition that at least 95 mol % of the entire silver halide constituting silver halide grains is composed of silver chloride and silver halide is composed of silver chlorobromide containing substantially no silver iodide. The term "containing substantially no silver iodide" as used herein means that the content of silver iodide is not higher than 1.0 mol %. It is particularly preferred that the silver halide grains have such a halogen composition that 95 to 99.9 mol % of the entire silver halide constituting silver halide grains is composed of silver chloride and silver halide is composed of silver chlorobromide containing substantially no silver iodide.

It is also preferred that the silver halide grains of the present invention have localized phases on the surfaces of grains and/or in the interiors thereof, said localized phase being different in the silver bromide content from the substrate grain.

Further, it is preferred that the silver halide grains of the present invention have localized phases having a silver bromide content of more than 15 mol %. The localized phases whose silver bromide content is higher than that of the area surrounding them may be arbitrarily arranged according to purpose. The phases may exist in the interiors of the silver halide grains, on the surfaces thereof or on the sub-surfaces thereof or may exist partly in the interiors thereof and partly on the surfaces or sub-surfaces thereof. The localized phases may have a layer structure surrounding the silver halide grain in the interior thereof or on the surface thereof. Alternatively, the localized phases may have a discontinuously isolated structure. In a preferred embodiment of the arrangement of the localized phases, the localized phases having a silver bromide content of more than 15 mol % are formed by locally epitaxial growth on the surfaces of silver halide grains.

It is preferred that the silver bromide content of the localized phase exceeds 15 mol %. However, when the silver bromide content is too high, there is a possibility that when pressure is applied to the light-sensitive material, desensitization is caused and sensitivity and gradation are greatly varied by change in the composition of the processing solution. As a result, the photographic material is deteriorated. When this is taken into consideration, the silver bromide content is in the range of preferably 20 to 60 mol %, most preferably 30 to 50 mol %. Silver chloride is preferred as other silver halide which constitutes the localized phase. The silver bromide content of the localized phase can be analyzed by X-ray diffractometry (e.g., described in New Experimental Chemical Lecture 6, Structure Analysis, edited by Japanese Chemical Society, published by Maruzen) or XPS method (e.g., "Surface Analysis, —IMA, Application of O. J. electron, photoelectron spectroscopy"). The localized phase comprises preferably 0.1 to 20%, more preferably 0.5 to 7% of the total amount of silver of silver halide grain.

The interface between the localized phase having a high silver bromide content and other phase may be a clear phase boundary or may have a short transition zone where the halogen composition is gradually changed.

The localized phases having such a high silver bromide content can be formed by various methods. For example, the localized phases can be formed by reacting a soluble silver salt with a soluble halide salt according to a single jet process or a double jet process, or by a conversion method including a stage where an already formed silver halide is converted to silver halide having a smaller solubility product. Alternatively, the localized phases can be formed by adding fine silver bromide grains to silver chloride grains to recrystallize fine silver bromide grains on the surfaces of the silver chloride grains.

When silver halide grains have the discontinuously isolated localized phases on the surfaces of the grains, the grain substrate and the localized phase exist on the same surface and hence they function simultaneously in each process of exposure and development. Accordingly, such grains have advantages in high sensitization, the formation of latent image, rapid processing, particularly the balance of gradation, in the effective utilization of silver halide, etc. High sensitization, the stabilization of sensitivity, the stability of the latent image, etc. which cannot be achieved by conventional infrared sensitized high silver chloride emulsions can be remarkably improved on the whole by providing the localized phase, while retaining rapid processability which silver chloride emulsions have is kept.

Rapid development can be easily facilitated by adsorbing anti-fogging agents, sensitizing dyes, etc. on the grain substrates and the localized phases so as to allow them to function separately or by chemically sensitizing them to inhibit the formation of fog.

The silver halide grains of the present invention are a hexahedron, tetradecahedron, etc. having (100) face. It is preferred that the localized phases exist on the corners of the hexahedrons or in the vicinity thereof, or on the surface site of (111) face. Such discontinuously isolated localized phases existing on the surfaces of the silver halide grains can be formed by halogen conversion wherein bromine ion is fed to an emulsion comprising substrate grains while pAg, pH, temperature and time are controlled. Preferably, halogen ion at a low concentration is fed. For example, halogen compounds having a capsule film covered with a semi-penetration film or organic halogen compounds can be used. Further, the localized phases can be formed by a method wherein silver halide is grown on localized sites by feeding silver ion and halogen ion to an emulsion comprising the substrate grains while controlling pAg, etc. or a method wherein silver halide grains such as fine grains of silver iodobromide, silver bromide, silver chlorobromide or silver iodochlorobromide which have a smaller grain size than that of the substrate grains are mixed with an emulsion comprising the substrate grain to recrystallize fine grains. If desired, a small amount of a solvent for silver halide is allowed to coexist. Further, CR-compounds described in European Patents 273430 and 273429, Japanese Patent Application Nos. 62-86163, 62-86165 and 62-152330 and Japanese Patent Application No. 62-86252 (corresponding to JP-A-1-6941) can be used. The end point of the formation of the localized phases can be judged by observing the form of silver halide during the course of ripening while comparing the form of the grains during ripening with the form of the silver halide grains of the substrate. The silver halide composition of the localized phases can be measured by XPS (X-ray photoelection spectroscopy using, for example, ESCA 750 type spectrograph (manufactured by Shimazu-du Pont). More concretely, the measurement is described in *Surface Analysis,* written by Someno and Yasumorii (published by Kodansha, 1977). Of course, the silver halide composition can be calculated from manufacturing formulation. The silver halide composition such as silver bromide content of the localized phases on the surface of silver halide can be measured by EDX (Energy Dispersive X-ray Analysis) using EDX spectrometer equipped with a transmission type electron microscope. The measurement can be made with an accuracy of about 5 mol % by using an aperture having a diameter of about 0.1 to 0.2 μm. More concretely, the measurement is described in *Electron Beam Microanalysis,* written by Hiroyoshi Soejima (published by Nikkan Kogyo Shinbunsha, 1987).

The silver halide emulsions of the present invention comprise grains having a mean grain size (an average of the diameters of spheres having a volume equal to grain) of preferably not larger than 2 μm, but not smaller than 0.1 μm, more preferably not larger than 0.4 μm, but not smaller than 0.15 μm.

A narrower grain size distribution is preferred and monodisperse emulsions are preferred. Monodisperse emulsions having a regular form are particularly preferred. It is preferred that emulsions comprise grains having such a grain size distribution that at least 85%, particularly at least 90% (in terms of the number of grains or the weight of grains) of the entire grains is composed of grains having a grain size of within the mean grain size ±20%.

The silver chlorobromide emulsions of the present invention can be prepared according to the methods described in P. Glafkides, *Chimie et Physique Photographique* (Paul Montel, 1967), G. F. Duffin, *Photographic Emuslion Chemistry* (Focal Press, 1966), V. L. Zelikman et al., *Making and Coating Photographic Emulsion* (Focal Press, 1964), etc. Namely, any of the acid process, the neutral process and the ammonia process can be used, but the acid process is particularly preferred. A soluble silver salt and a soluble halide salt can be reacted in accordance with a single jet process, a double jet process or a combination thereof. The double jet process is preferred to obtain monodisperse grains which can be preferably used in the present invention. There can be used a reverse mixing method in which grains are formed in the presence of excess silver ion. There can also be used a controlled double jet process in which the concentration of silver ion in a liquid phase, in which silver halide is formed, is kept constant. According to this process, there can be obtained a monodisperse silver halide emulsion which comprises grains having a regular crystal form and a narrow grain size distribution and is suitable for use in the present invention. It is desirable that the above-described grains suitable for use in the present invention are prepared on the basis of the double jet process.

It is preferred that physical ripening is carried out in the presence of conventional solvents for silver halide (e.g., ammonia, potassium thiocyanate or thioethers and thione compounds described in U.S. Pat. No. 3,271,157, JP-A-51-12360, JP-A-53-82408, JP-A-53-144319, JP-A-54-100717, JP-A-54-155828, etc.), because there can be obtained a monodisperse silver halide emulsion which comprises grains having a regular crystal form and a narrow grain size distribution.

After physical ripening, soluble silver salts can be removed from the emulsion by noodle washing, flocculation precipitation method, ultrafiltration, etc.

Silver halide emulsions which are used in the present invention can be chemical-sensitized by sulfur sensitization, selenium sensitization, reduction sensitization, noble metal sensitization, etc. singly or in combination. Namely, there can be used sulfur sensitization method using active gelatin or sulfur-containing compounds capable of reacting with silver ion (e.g., thiosulfates, thiourea compounds, mercapto compounds, rhodanine compounds); reduction sensitization methods using reducing materials (e.g., stannous salts, amine salts, hydrazine derivatives, formamidine-sulfinic acid, silane compounds); and noble metal sensitization method using metallic compounds (e.g., gold complex salts and complex salts of Group VIII metals in the periodic table such as Pt, Ir, Pd, Rh and Fe). These methods may be used alone or in combination. Complex salts of Group VIII metals such as Ir, Rh and Fe may be separately used in the substrate and the localized phase, or may be distributed between the substrate and the localized phase. Sulfur sensitization or selenium sensitization is particularly preferred for the monodisperse silver chlorobromide emulsion which can be preferably used in the present invention. It is also preferred that sensitization is carried out in the presence of a hydroxyazaindene compound.

Light Source

Exposure for obtaining a photographic image may be carried out by conventional methods. Any of conventional light sources such as natural light (sunlight), tungsten light, fluorescent lamp, mercury vapor lamp, xenon arc lamp, carbon arc lamp, xenon flash lamp and cathode ray tube flying spot can be used. Exposure time is generally from 1/1000 second to 1 second when a camera is used. However, exposure time of shorter than 1/1000 second may be used. For example, when xenon flash lamp or cathode ray tube is used, exposure time may be as short as $1/10^4$ to $1/10^6$ second. If desired, exposure time of longer than 1 second may be used. If desired, the spectral composition of light for use in exposure can be controlled through color filters. Laser beam can be used for exposure. Exposure may be carried out by light radiated from phosphors excited by electron beam, X-rays, gamma rays, alpha rays, etc.

When laser beam is used, semiconductor laser is preferred. Examples of the semiconductor laser include those using materials such as $In_{1-x}Ga_xP$ (~700 nm), $GaAs_{1-x}P_x$ (610~900 nm), $Ga_{1-x}Al_xAs$ (690~900 nm), InGaAsP (1100~1670 nm) and AlGaAsSb (1250~1400 nm). In addition to the above-described semiconductor laser, there may be used YAG laser (1064 nm) wherein Nb: YAG crystal is excited with $GaAs_xP_{(1-x)}$ light-emitting diode. It is preferred that laser beam is chosen from among semiconductor laser beams of 670, 680, 750, 780, 810, 830 and 880 nm.

Further, non-linear optical effect may be used. Secondly higher frequency forming element (SHG element) refers to that the wavelength of laser beam is transduced into ½ by utilizing non-linear optical effect. For example, there can be used an element using CD*A and KD*P as non-linear optical crystals (see, Laser Handbook, pages 122–139, edited by Laser Society, Dec. 15, 1982). Further, there can be used $LiNbO_3$ light waveguide path element wherein a light waveguide path is formed with $LiNbO_3$ crystal by ion-exchanging Li+ with H+ (NIKKEI ELECTRONICS, 1986,7,14 (No. 399) pages 89–90).

An output device described in Japanese Patent Application No. 63-226552 (corresponding to JP-A-2-74942) can be used in the present invention.

Processing

Light-sensitive materials prepared by the present invention can be processed by conventional photographic processing methods (color photographic processing) and processing solutions for forming dye images as described in *Research Disclosure*, No. 176, pages 28–30 (RD-17643) (December 1978).

Preferred embodiments of color development stage and processing solutions which can be applied to the light-sensitive materials of the present invention are illustrated below.

It is preferred that the color photographic materials of the present invention are subjected to color development, bleaching-fixing and rinsing (or stabilization treatment). Bleaching and fixing may be carried out by one bath as described above or may be separately carried out.

Color developing solutions which are used in the present invention contains aromatic primary amine color developing agents. Preferred developing agents are p-phenylenediamine derivatives. Typical examples of the p-phenylenediamine derivatives include, but are not limited to, the following compounds.

D-1 N,N-Diethyl-p-phenylenediamine
D-2 2-Amino-5-diethylaminotoluene
D-3 2-Amino-5-(N-ethyl-N-laurylamino)toluene
D-4 4-[N-Ethyl-N-($\beta$-hydroxyethyl)amino]aniline
D-5 2-Methyl-4-[N-ethyl-N-($\beta$-hydroxyethyl)amino]aniline
D-6 4-Amino-3-methyl-N-ethyl-N-[$\beta$-(methanesulfonamido)ethyl]aniline
D-7 N-(2-Amino-5-diethylaminophenylethyl)methanesulfonamide
D-8 N,N-Dimethyl-p-phenylenediamine
D-9 4-Amino-3-methyl-N-ethyl-N-methoxyethylaniline
D-10 4-Amino-3-methyl-N-ethyl-N-$\beta$-ethoxyethylaniline
D-11 4-Amino-3-methyl-N-ethyl-N-$\beta$-butoxyethylaniline Among the above-described p-phenylenediemine derivatives, 4-amino-3-methyl-N-ethyl-N-[$\beta$-(methanesulfonamido)ethyl]aniline (Compound D-6) is particularly preferred.

These p-phenylenediamine derivatives may be used in the form of a salt such as sulfate, hydrochloride, sulfite or p-toluenesulfonate. The aromatic primary amine developing agents are used at a concentration of preferably about 0.1 to about 20 g, more preferably about 0.5 to about 10 g per liter of developing solution.

In the practice of the present invention, it is preferred that developing solutions containing substantially no benzyl alcohol are used. The term "containing substantially no benzyl alcohol" as used herein means that the concentration of benzyl alcohol is preferably not higher than 2 ml/l, more preferably not higher than 0.5 ml/l. It is most preferred that the developing solutions are completely free from benzyl alcohol.

It is also preferred that the developing solutions of the present invention contain substantially no sulfite ion. Sulfite ion functions as a preservative for the developing agents and at the same time, sulfite ion has an effect of dissolving silver halide and is reacted with the oxidation products of the developing agents to thereby reduce a dye-forming efficiency. It is believed that such effects cause an increase in the fluctuation of photographic characteristics in continuous processing. The term "containing substantially no sulfite ion" as used herein means that the concentration of sulfite ion is preferably not higher than $3.0 \times 10^{-3}$ mol/l. It is most preferred that the developing solutions are completely free from sulfite ion. In the present invention, however, a very small amount of sulfite ion is excluded, said sulfite ion being used to prevent processed kit containing a concentrated developing agent before the preparation of a working solution from being oxidized.

It is preferred that the developing solutions of the present invention contain substantially no sulfite ion as mentioned above. It is more preferred that the developing solutions contain substantially no hydroxylamine. This is because it is believed that hydroxylamine functions as a preservative and at the same time, hydroxylamine itself has a silver development activity and photographic characteristics are greatly affected by a change in the concentration of hydroxylamine. The term "containing substantially no hydroxylamine" as used herein means that the concentration of hydroxylamine is preferably not more than $5.0 \times 10^{-3}$ mol/l. It is most preferred that the developing solutions are completely free from hydroxylamine.

It is preferred that the developing solutions of the present invention contain organic preservatives in place of hydroxylamine and sulfite ion.

The term "organic preservative" as used herein refers to the whole of organic compounds having an effect of retarding the deterioration rate of aromatic primary amine color developing agents when added to processing solutions for color photographic materials. Namely, the organic preservatives are organic compounds which have a function capable of preventing the color developing agents from being oxidized by air, etc. Among them, particularly effective organic preservatives are hydroxylamine derivatives (excluding hydroxylamine, the same applies hereinafter), hydroxamic acids, hydrazines, hydrazides, phenols, $\alpha$-hydroxyketones, $\alpha$-aminoketones, saccharide, monoamines, diamines, polyamines, quaternary ammonium salts, nitroxyl radicals, alcohols, oximes, diamide compounds and condensed ring amines. These compounds are described in JP-A-63-4235, JP-A-63-30845, JP-A-63-21647, JP-A-3-44655, JP-A-63-53551, JP-A-63-43140, JP-A-63-56654, JP-A-63-58346, JP-A-63-43138, JP-A-63-146041, JP-A-63-44657, JP-A-63-44656, U.S. Pat. Nos. 3,615,503 and 2,494,903, JP-A-52-143020, JP-B-48-30496, etc.

Other preservatives such as various metals described in JP-A-57-44148 and JP-A-57-53749; salicylic acids described in JP-A-59-180588; alkanolamines described in JP-A-54-3532; polyethyleneimines described in JP-A-56-94349; and aromatic polyhydroxy compounds described in U.S. Pat. No. 3,746,544 may be optionally contained. Particularly, the addition of alkanolamines such as triethanolamine, dialkylhydroxylamines such as diethylhydroxylamine, hydrazine derivatives or aromatic polyhydroxy compounds is preferred.

Among the organic preservatives, hydroxylamine derivatiaves and hydrazine derivatives (hydrazines and hydrazides) are particularly preferred. The details thereof are described in Japanese Patent Application Nos. 62-255270, 63-9713, 63-9714 and 63-11300 (corresponding to JP-A-1-97953, JP-A-1-186939, JP-A-1-186940 and JP-A-1-187557, respectively), etc.

It is more preferred from the viewpoint of improving the stability of the color developing solutions, that is, improving stability during continuous processing that the hydroxylamine derivatives or the hydrazine derivatives are used in combination with the amines.

The amines include cyclic amines described in JP-A-63-239477, amines described in JP-A-63-128340 and amines described in Japanese Patent Application Nos. 63-9713 and 63-11300 (corresponding to JP-A-1-186939 and JP-A-1-187557, respectively).

It is preferred that the color developing solutions of the present invention contain chlorine ion in an amount of $3.5 \times 10^{-2}$ to $1.5 \times 10^{-1}$ mol/l, particularly preferably $4 \times 10^{-2}$ to $1 \times 10^{-1}$ mol/l. When the concentration of chlorine ion is higher than $1.5 \times 10^{-1}$ mol/l, there is a disadvantage that development is retarded. Accordingly, such an amount is not preferred for purposes of rapid processing and providing high maximum density. On the other hand, when the concentration is lower than $3.5 \times 10^{-2}$ mol/l, fogging cannot be sufficient prevented from being caused.

It is also preferred that the color developing solutions of the present invention contain bromine ion in an amount of $3.0 \times 10^{-5}$ to $1.0 \times 10^{-3}$ mol/l, more preferably $5.0 \times 10^{-5}$ to $5 \times 10^{-4}$ mol/l. When the concentration of bromine ion is higher than $1 \times 10^{-3}$ mol/l, development is retarded and maximum density and sensitivity are lowered, while when the concentration is lower than $3.0 \times 10^{-5}$ mol/l, fogging cannot be sufficient prevented from being caused.

Chlorine ion and bromine ion may be added directly to the developing solution or may be dissolved out from the light-sensitive material into the developing solution during development.

When chlorine ion is directly added to the color developing solution, examples of chlorine ion supply materials include sodium chloride, potassium chloride, ammonium chloride, lithium chloride, nickel chloride, magnesium chloride, manganese chloride, calcium chloride and cadmium chloride. Among them, sodium chloride and potassium chloride are preferred.

Alternatively, chlorine ion may be supplied from brightening agent contained in the developing solution.

Examples of bromine ion supply materials include sodium bromide, potassium bromide, ammonium bromide, lithium bromide, calcium bromide, magnesium bromide, manganese bromide, nickel bromide, cadmium bromide, cerium bromide and thallium bromide. Among them, potassium bromide and sodium bromide are preferred.

When chlorine ion or bromine ion is to be dissolved out from the light-sensitive material during development, chlorine ion or bromine ion is supplied from emulsions or other sources.

The color developing solutions of the present invention have a pH of preferably 9 to 12, more preferably 9 to 11.0. The color developing solutions may contain conventional additive compounds for developing solutions.

It is preferred that buffering agents are used to keep the pH. Examples of the buffering agents include carbonates, phosphates, borates, tetraborates, hydroxybenzoates, glycyl salts, N,N-dimethylglycine salts, leucine salts, norleucine salts, guanine salts, 3,4-dihydroxyphenylalanine salts, alanine salts, aminobutyrates, 2-amino-2-methyl-1,3-propanediol salts, valine salts, proline salts, trishydroxyaminomethane salts and lysine salts. Particularly, carbonates, phosphates, tetraborates and hydroxybenzoates have advantages in that they are excellent in buffer capacity in the high pH zone of pH=9.0 or higher and do not have an adverse influence (e.g., fogging) on photographic characteristics when added to the color developing solutions. Further, they are inexpensive. Accordingly, it is particularly preferred that these buffering agents are used.

Concrete examples of these buffering agents include sodium carbonate, potassium carbonate, sodium bicarbonate, potassium bicarbonate, sodium phosphate, potassium phosphate, disodium hydrogenphosphate, dipotassium hydrogenphoaphate, sodium borate, potassium borate, sodium tetraborate (borax), potassium tetraborate, sodium o-hydroxybenzoate (sodium salicylate), potassium o-hydroxybenzoate, sodium 5-sulfo-2-hydroxybenzoate (sodium 5-sulfosalicylate) and potassium 5-sulfo-2-hydroxybenzoate (potassium 5-sulfosalicylate). However, the buffering agents which can be used in the present invention are not limited to the above-described compounds.

The amounts of the buffering agents to be added to the color developing solutions are preferably not less than 0.1 mol/l, particularly preferably 0.1 to 0.4 mol/l.

The color developing solutions may contain various chelating agents as suspending agents for calcium or magnesium ion or to improve the stability of the color developing solutions.

Examples of the chelating agents include nitrilotriacetic acid, diethylenetriaminepentaacetic acid, ethylene diaminetetraacetic acid, N,N,N-trimethylenephosphonic acid, ethylenediamine-N,N,N',N'-tetramethylensulfonic acid, trans-cyclohexanediaminetetraacetic acid, 1,2-diaminopropanetetraacetic acid, glycol ether diaminetetraacetic acid, ethylenediamine-o-hydroxyphenylacetic acid, 2-phosphonobutane-1,2,4-tricarboxylic acid, 1-hydroxyethylidene-1,1-diphosphonic acid and N,N'-bis(2-hydroxybenzyl)ethylenediamine-N,N'-diacetic acid.

These chelating agents may be used either alone or in combination of two or more of them.

The amounts of these chelating agents to be added may be a sufficient amount to sequester metal ions in the color developing solutions and are generally 0.1 to 10 g per one liter.

The color developing solutions may optionally contain development accelerators.

Examples of the development accelerators include thioether compounds described in JP-B-37-16088, JP-B-37-5987, JP-B-38-7826, JP-B-44-12380, JP-B-45-9019, U.S. Pat. No. 3,813,247, etc.; p-phenylenediamine compounds described in JP-A-52-49829 and JP-A-50-15554; quaternary ammonium salts described in JP-A-50-137726, JP-B-44-30074, JP-A-56-156826, JP-A-52-43429, etc., amine compounds described in U.S. Pat. Nos. 2,494,903, 3,128,182, 4,230,796 and 3,253,919, JP-B-41-11431, U.S. Pat. Nos. 2,482,546, 2,596,926 and 3,582,346, etc.; polyalkylene oxides described in JP-B-37-16088, JP-B-42-25201, U.S. Pat. No. 3,128,183, JP-B-41-11431, JP-B-42-23883, U.S. Pat. No. 3,532,501, etc.; 1-phenyl-3-pyrazolidones and imidazoles.

If desired, anti-fogging agents may be added in the present invention. The anti-fogging agents include alkali metal halides such as sodium chloride, potassium bromide and potassium iodide and organic anti-fogging agents. Typical examples of the organic anti-fogging agents include nitrogen-containing heterocyclic compounds such as benztriazole, 6-nitrobenzimidazole, 5-nitroisoindazole, 5-methylbenztriazole, 5-nitrobenztriazole, 5-chlorobenztriazole, 2-thiazolyl-benzimidazole, 2-thiazolylmethyl-benzimidazole, indazole, hydroxyazaindolizine and adenine.

It is preferred that the color developing solutions of the present invention contain brightening agents. As the brightening agents, 4,4'-diamino-2,2'-disulfostilbene compounds are preferred. The brightening agents are used in an amount of 0 to 5 g/l, preferably 0.1 to 4 g/l.

If desired, various surfactants such as alkylsulfonic acids, arylsulfonic acids, aliphatic carboxylic acids and aromatic carboxylic acids may be added.

The processing temperature of the color developing solutions of the present invention is from 20° to 50° C., preferably from 30° to 40° C. Processing time is from 20 seconds to 5 minutes, preferably from 30 seconds to 2 minutes. A less replenishment rate is preferred, but the replenishment rate is generally 20 to 600 ml, preferably 50 to 300 ml, more preferably 60 to 200 ml, most preferably 60 to 150 ml per m$^2$ of light-sensitive material.

The desilverization stage of the present invention is illustrated below.

As the desilverization stage, any of bleaching stage-fixing stage, fixing stage-bleaching and fixing stage, bleaching stage-bleaching and fixing stage, and bleaching-fixing stage may be used.

The bleaching solution, bleaching-fixing solution and the fixing solution of the present invention are illustrated below.

Any of bleaching agents can be used as bleaching agents used in the bleaching solution and the bleaching-fixing solution. Preferred examples of the bleaching agents include organic complex salts of iron(III) (e.g., complex salts of aminopolycarboxylic acids such as ethylenediaminetetraacetic acid and diethylenetriaminepentaacetic acid, aminopolyphosphonic acids, phosphonocarboxylic acids and organic phosphonic acids) and organic acids such as citric acid, tartaric acid and malic acid; persulfates; and hydrogen peroxide.

Among them, the organic complex salts of iron(III) are preferred from the viewpoint of rapid processing and the prevention of environmental pollution. Examples of aminopolycarboxylic acids, aminopolyphosphonic acids, organic phosphonic acids and salts thereof which are useful in the formation the organic complex salts of iron(III) include ethylenediaminetetraacetic acid, diethylenetriaminepentaacetic acid, 1,3-diaminopropanetetraacetic acid, propylenediaminetetraacetic acid, nitrilotriacetic acid, cyclohexanediaminetetraacetic acid, methyliminodiacetic acid, iminodiacetic acid, glycol ether diaminetetraacetic acid and salts thereof such as sodium, potassium, lithium and ammonium slats. Among these compounds, iron(III) complex salts of ethylenediaminetetraacetic acid, diethylenetriaminepentaacetic acid, cyclohexanediaminetetraacetic acid, 1,3-diaminopropanetetraacetic acid and methyliminodiacetic acid are preferred, because they have high bleaching power. These ferric ion complex salts may be used in the form of a complex salt or may be formed in solutions by using a ferric salt such as ferric sulfate, ferric chloride, ferric nitrate, ammonium ferric sulfate or ferric phosphate with a chelating agent such as an aminopolycarboxylic acid, an aminopolyphosphonic acid or a phosphonocarboxylic acid. The chelating agent may be used in an amount of more than that required for forming the ferric ion complex salt. Among the iron complexes, there are preferred the iron complexes of the aminopolycarboxylic acids. The iron complexes are used in an amount of 0.01 to 1.0 mol/l, preferably 0.05 to 0.50 mol/l.

The bleaching solutions, the bleaching-fixing solutions and/or prebath thereof may contain various compounds as bleaching accelerators. Examples of such compounds include compounds having mercapto group or disulfide bond described in U.S. Pat. No. 3,893,858, German Patent 1,290,812, JP-A-53-95630, *Research Disclosure*, 17129 (July, 1978); thiourea compounds described in JP-B-45-8506, JP-A-52-20832, JP-A-53-32735, U.S. Pat. No. 3,706,561, etc.; and halides such as iodine and bromine ions. These compounds are excellent in bleaching power. Further, the bleaching solutions or the bleaching-fixing solutions of the present invention may contain re-halogenating agents such as bromides (e.g., potassium bromide, sodium bromide, ammonium bromide), chlorides (e.g., potassium chloride, sodium chloride, ammonium chloride) or iodides (e.g., ammonium iodide). If desired, one or more of inorganic acids, organic acids or their alkali metal or ammonium salts which have a pH buffer capacity, such as borax, sodium metaborate, acetic acid, sodium acetate, sodium carbonate, potassium carbonate, phosphorous acid, phosphoric acid, sodium phosphate, citric acid, sodium citrate and tartaric acid and corrosion inhibitors such as ammonium nitrate and guanidine may be added.

Conventional fixing agents can be used as fixing agents used in the bleaching-fixing solutions or the fixing solutions. The fixing agents include water-soluble solvents for silver halide, such as thiosulfates (e.g., sodium thiosulfate, ammonium thiosulfate), thiocyanates (e.g., sodium thiocyanate, ammonium thiocyanate), thioether compounds (e.g., ethylenebisthioglycolic acid, 3,6-dithia-1,8-octanediol) and thioureas. These compounds may be used either alone or as a mixture of two or more of them. Further, there can be used a specific bleching-fixing solution comprising a combination of a large amount of a halide such as potassium iodide and a fixing agent as described in JP-A-55-155354. Among these compounds, thiosulfates, particularly ammonium thiosulfate are preferred. The fixing agents are used in an amount of preferably 0.3 to 2 mol, more preferably 0.5 to 1.0 mol per liter. The pH of the bleaching-fixing solution or the fixing solution is in the range of preferably 3 to 10, more preferably 5 to 9.

The bleching-fixing solutions may contain other additives such as brightening agent, anti-foaming agent, surfactant, organic solvent such as polyvinyl pyrrolidone and methanol, etc.

It is preferred that the bleching-fixing solutions or the fixing solutions contain, as preservatives, sulfite ion-releasing compounds such as sulfites (e.g., sodium sulfide, potassium sulfite, ammonium sulfite, etc.), bisulfites (e.g., ammonium bisulfite, sodium bisulfite, potassium bisulfite, etc.) and metabisulfites (e.g., potassium metabisulfite, sodium metabisulfite, ammonium metabisulfite, etc.). These compounds are used in an amount of preferably about 0.02 to 0.05 mol/l, more preferably 0.04 to 0.40 mol/l in terms of sulfite ion.

Generally, sulfites are used as preservatives. In addition thereto, ascorbic acid, carbonyl bisulfite adducts, carbonyl compounds, etc. may be used.

Further, buffering agent, brightening agent, chelating agent, anti-foaming agent, mildewcide, etc. may be added, if necessary.

Usually, washing and/or stabilization treatment are/is carried out after desilverization treatment such as fixing or bleaching-fixing treatment.

The amount of washing water in the washing stage widely varies depending on the characteristics (e.g., depending on materials used such as couplers) of the light-sensitive materials, use, the temperature of washing water, the number of washing tanks (the number of stages), replenishing system (countercurrent, concurrent) and other conditions. The relationship between the amount of water and the number of washing tanks in the multi-stage countercurrent system can be determined by the method described in *Journal of the Society of Motion Picture and Television Engineers*, Vol. 64, p. 248–253 (May 1955). Usually, the number of stages in the multi-stage countercurrent system is preferably 2 to 6, particularly preferably 2 to 4.

According to the multi-stage countercurrent system, the amount of washing water can be greatly reduced. For example, the amount of washing water can be reduced to 0.5 to 1 liter per $m^2$ of light-sensitive material, and an effect obtained by the present invention is remarkable. However, there is caused a problem that the residence time of water in the tanks is prolonged and as a result, bacteria are grown and the resulting suspended matter is deposited on the light-sensitive material. A method for reducing calcium ion and magnesium ion described in JP-A-62-288838 can be effectively used to solve the above-mentioned problem. Further, there can be used isothiazolone compounds and thiabenzazole compounds described in JP-A-57-8542, chlorine-containing germicides such as sodium chlorinated isocyanurate described in JP-A-61-120145, benztriazole and copper ion described in JP-A-61-267761 and germicides described in *Chemistry of Germicidal Antifungal Agent*, (Sankyo Shuppan, 1986) written by Hiroshi Horiguchi, *Sterilization, Disinfection, Antifungal Technique* (Industrial Technique Society, 1982), edited by Sanitary Technique Society and Antibacterial and Antifungal Cyclopedie, (1986) edited by Nippon Antibacterial Antifungal Society.

Further, washing water may contain surfactants as wetting agent and chelating agents such as typically EDTA as water softener.

The light-sensitive material may be treated with a stabilizing solution after the washing stage or may be treated directly with a stabilizing solution without via the washing stage. Compounds having a function capable of stabilizing image are added to the stabilizing solution. For example, aldehyde compounds such as typically formalin, buffering agents for adjusting pH of film to a value suitable for stabilizing image and ammonium compounds are added. Further, the aforesaid germicides or mildewproofing agents may be added to inhibit the growth of bacteria or to impart mildew-proofness to the processed light-sensitive materials.

Further, surfactants, brightening agents and hardening agents can be added. When stabilization is directly carried out without via the washing stage in the processing of the light-sensitive materials of the present invention, all of known methods described in JP-A-57-8543, JP-A-58-14834, JP-A-60-220345, etc. can be used. In other preferred embodiment, chelating agents such as 1-hydroxyethylidene-1,1-diphosphonic acid and ethylenediaminetetramethylenephosphonic acid, magnesium compounds and bismuth compounds are used.

Rinse solution can be equally used as washing solution or stabilizing solution used after desilverization.

The pH in the washing stage or the stabilizing stage is preferably 4 to 10, more preferably 5 to 8. Temperature widely varies depending on the use, characteristics, etc. of the light-sensitive materials, but is generally 15° to 45° C., preferably 20° to 40° C. Time can be arbitrarily set, but shorter time is preferred from the viewpoint of shortening processing time. Time is preferably from 15 seconds to 105 seconds, more preferably from 30 seconds to 90 seconds. Less replenishment rate is preferred from the viewpoints of running cost, the reduction of discharged solution, handling, etc.

Concretely, replenishment rate per the unit area of the light-sensitive material is preferably 0.5 to 50 times, more preferably 3 to 40 times the amount brought over from the prebath. Alternatively, the replenishment rate is not more than 1 liter, preferably not more than 500 ml per $m^2$ of light-sensitive material. Replenishment may be carried out continuously or intermittently.

The solution used in the washing and/or stabilizing stages can be further used in the pre-stage. For example, in the multi-stage countercurrent system, the overflow solution of washing water is allowed to flow into the bleaching-fixing bath which is a prebath, and the bleaching-fixing bath is replenished with a concentrated solution to thereby reduce the amount of waste solution.

Other Constituents

Cyan couplers, magenta couplers and yellow couplers which can be preferably used in the present invention are compounds represented by the following general formulae (C-I), (C-II), (M-I), (M-II) and (Y).

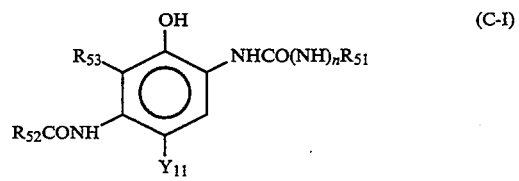
(C-I)

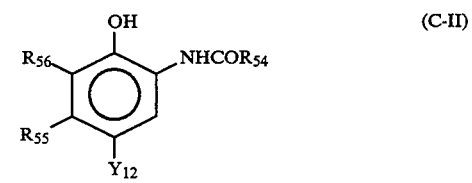
(C-II)

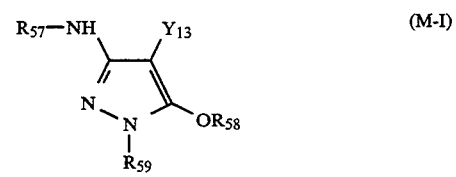
(M-I)

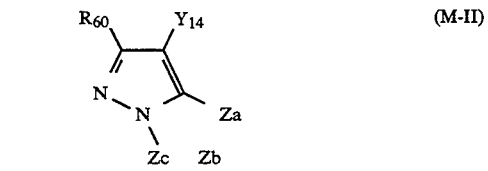
(M-II)

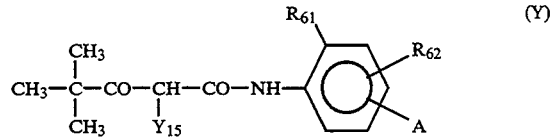
(Y)

In general formulae (C-I) and (C-II), $R_{51}$, $R_{52}$ and $R_{54}$ represent each a substituted or unsubstituted aliphatic, aromatic or heterocyclic group; $R_{53}$, $R_{55}$ and $R_{56}$ represent each hydrogen atom, a halogen atom, an aliphatic group, an aromatic group or an acylamino group; $R_{53}$ may be a non-metallic atomic group required for forming a nitrogen-containing 5-membered or 6-membered ring together with $R_{52}$; $Y_{11}$ and $Y_{12}$ represent each hydrogen atom or a group which is eliminated by the coupling reaction with the oxidants of developing agents; and n represents 0 or 1.

$R_{55}$ in general formula (C-II) is preferably an aliphatic group such as methyl group, ethyl group, propyl group, butyl group, pentadecyl group, t-butyl group, cyclohexyl group, cyclohexylmethyl group, phenylthiomethyl group, dodecyloxyphenylthiomethyl group, butaneamidomethyl group or methoxymethyl group.

Preferred examples of the cyan couplers represented by general formula (C-I) or (C-II) include the following compounds.

Preferably, $R_{51}$ in general formula (C-I) is an aryl group or a heterocyclic group. More preferably, $R_{51}$ is an aryl group substituted by one or more of a halogen atom, an alkyl group, an alkoxy group, an aryloxy group, an acylamino group, an acyl group, a carbamoyl group, a sulfonamido group, a sulfamoyl group, a sulfonyl group, a sulfamido group, an oxycarboxyl group and cyano group.

When $R_{53}$ and $R_{52}$ in general formula (C-I) are not combined together to form a ring, $R_{52}$ is preferably a substituted or unsubstituted alkyl or aryl group with a substituted aryloxy-substituted alkyl group being particularly preferred, and $R_{53}$ is preferably hydrogen atom.

In general formula (C-II), $R_{54}$ is preferably a substituted or unsubstituted alkyl or aryl group with a substituted aryloxy-substituted alkyl group being particularly preferred.

In general formula (C-II), $R_{55}$ is preferably an alkyl group having 2 to 15 carbon atoms and a methyl group having a substituent group having one or more carbon atoms. Preferred examples of the substituent group include an arylthio group, an alkylthio group, an acylamino group, an aryloxy group and an alkyloxy group.

More preferably, $R_{55}$ in general formula (C-II) is an alkyl group having 2 to 15 carbon atoms with an alkyl group having 2 to 4 carbon atoms being particularly preferred.

In general formula (C-II), $R_{56}$ is preferably carbon atom or halogen with chlorine or fluorine atom being particularly preferred.

In general formulae (C-I) and (C-II), $Y_{11}$ and $Y_{12}$ are preferably each hydrogen atom, a halogen atom, an alkoxy group, an aryloxy group, an acyloxy group or a sulfonamido group.

In general formula (M-I), $R_{57}$ and $R_{59}$ represent each an aryl group; $R_{58}$ represents hydrogen atom, an aliphatic or aromatic acyl group or an aliphatic or aromatic sulfonyl group; and $Y_{13}$ represents hydrogen atom or an eliminable group. The aryl group (preferably phenyl group) represented by $R_{57}$ and $R_{59}$ may be substituted. Examples of substituent groups are those described above in the definition of the substituent groups for $R_{51}$. When two or more substituent groups are attached, they may be the same or different groups.

$R_{58}$ is preferably hydrogen atom or an aliphatic acyl or sulfonyl group with hydrogen atom being particularly preferred. Preferably, $Y_{13}$ is a group which is eliminated through sulfur, oxygen or nitrogen atom, and sulfur elimination type described in U.S. Pat. No. 4,351,897 and WO 88/04795 is particularly preferred.

In general formula (M-II), $R_{60}$ represents hydrogen atom or a substituent group; $Y_{14}$ represents hydrogen atom or an eliminable group with a halogen atom or an arylthio group being particularly preferred; Za, Zb and Zc represent each methine group, a substituted methine group or a group of $=N-$ or $-NH-$ and one of Za—Zb bond and Zb—Zc bond is a double bond and the other is a single bond. When Zb—Zc bond is a carbon-to-carbon double bond, the bond may form a moiety of an aromatic ring. When a dimer or a higher polymer is formed through $R_{60}$ or $Y_{14}$, the case where a dimer or a higher polymer is formed is included within the scope of the present invention. Further, when Za, Zb or Zc is a substituted methine group and a dimer or a higher polymer is formed through the substituted methine group, the case where a dimer or a higher polymer is formed is included within the scope of the present invention.

Among the pyrazoloazole couplers represented by general formula (M-II), imidazo[1,2-b]pyrazoles described in U.S. Pat. No. 4,500,630 are preferred from the viewpoints of less secondary yellow absorption of developed dyes and fastness to light, and pyrazolo[1,5-b][1,2,4]triazole described in U.S. Pat. No. 4,540,654 is particularly preferred.

In addition thereto, there are preferred pyrazolotriazole couplers wherein a branched alkyl group is directly attached to the 2-, 3- or 6-position of pyrazolotriazole ring as described in JP-A-61-65245; pyrazoloazole couplers having a sulfonamido group in the molecule as described in JP-A-61-65246; pyrazoloazole couplers having an alkoxyphenylsulfonamido ballast group as described in JP-A-61-147254; and pyrazolotriazole couplers having an alkoxy group or an aryloxy group at the 6-position thereof as described in EP-A-226849 and EP-A-294785.

In general formula (Y), $R_{61}$ represents a halogen atom, an alkoxy group, trifluoromethyl group or an aryl group; $R_{62}$ represents hydrogen atom, a halogen atom or an alkoxy group; A represents $-NHCOR_{63}$, $-NHSO_2-R_{63}$, $-SO_2NHR_{63}$, $-COOR_{63}$ or

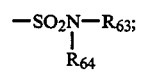

$R_{63}$ and $R_{64}$ represent each an alkyl group, an aryl group or an acyl group; and $Y_{15}$ represents an eliminable group. Examples of substituent groups for $R_{62}$, $R_{63}$ and $R_{64}$ are those described above in the definition of the substituent groups for $R_{51}$. The eliminable group $Y_{15}$ is preferably a type of a group which is eliminated through oxygen atom or nitrogen atom. Nitrogen atom elimination type is particularly preferred.

Examples of couplers represented by general formulae (C-I), (C-II), (M-I), (M-II) and (Y) include the following compounds.

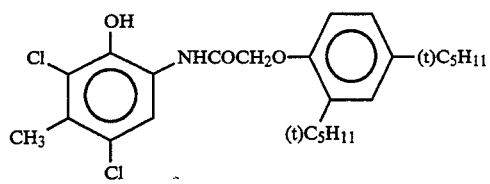 (C-1)
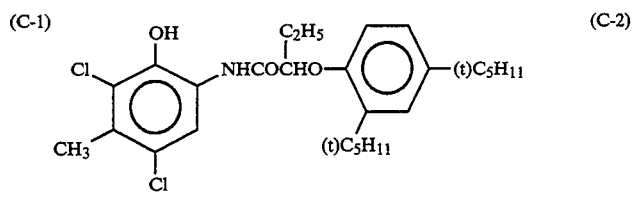 (C-2)
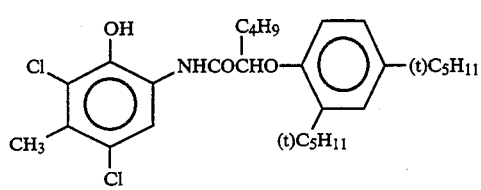 (C-3)
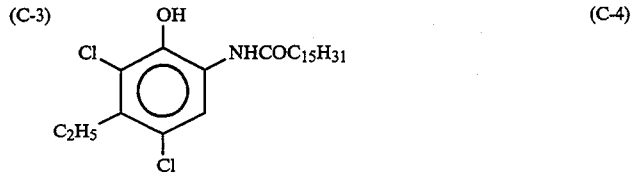 (C-4)
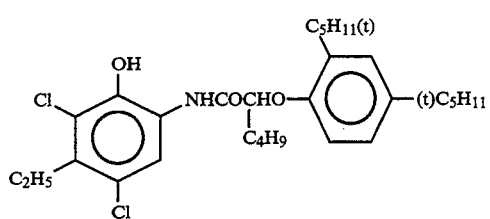 (C-5)
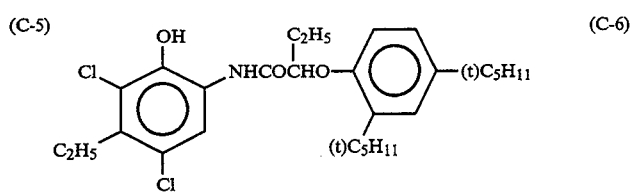 (C-6)
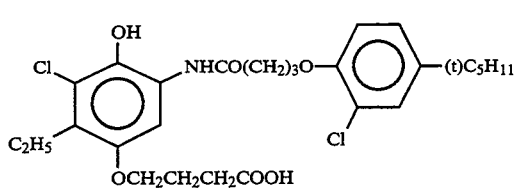 (C-7)
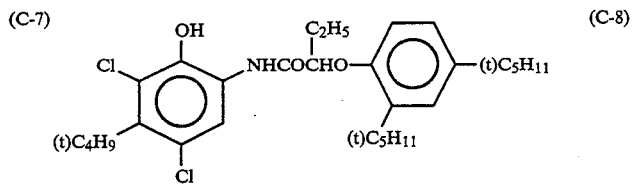 (C-8)
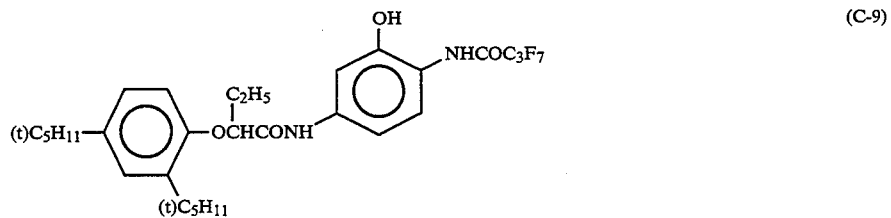 (C-9)
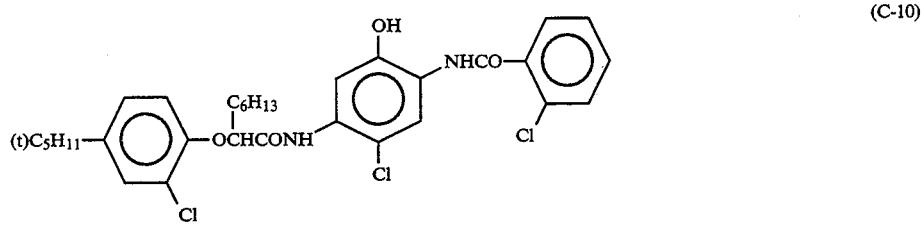 (C-10)
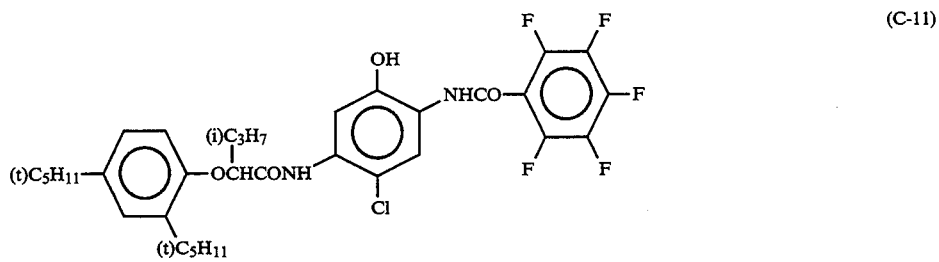 (C-11)

-continued
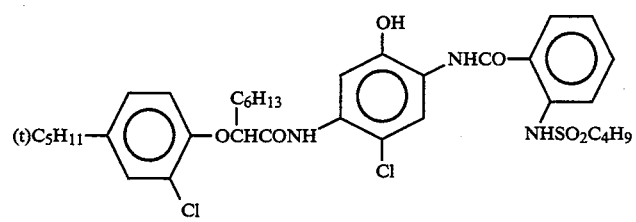
(C-12)
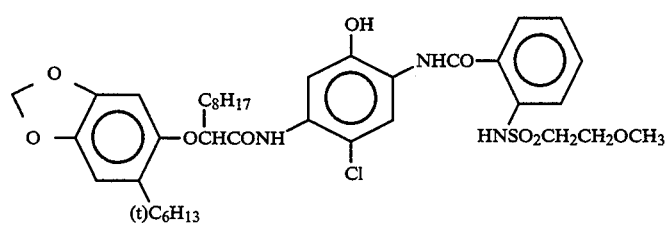
(C-13)
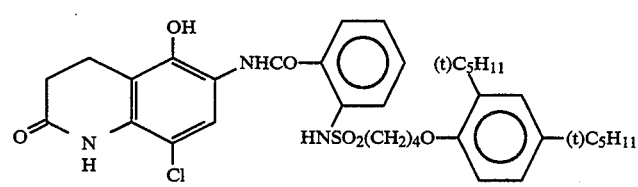
(C-14)
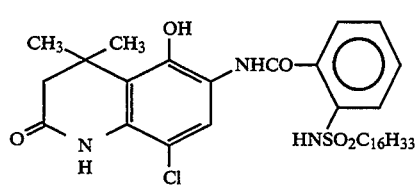
(C-15)
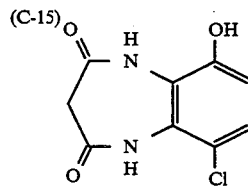
(C-16)
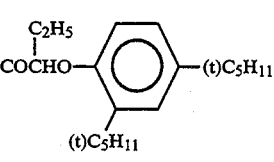
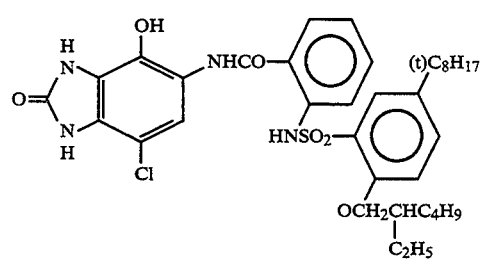
(C-17)
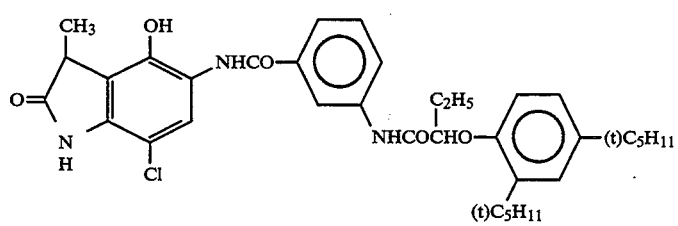
(C-18)
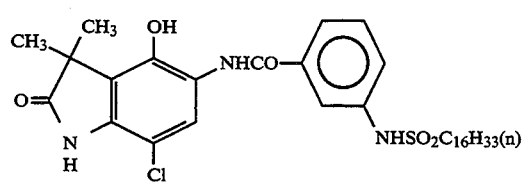
(C-19)

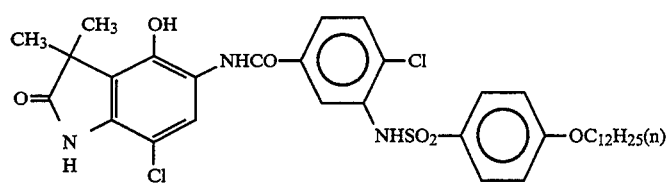
(C-20)
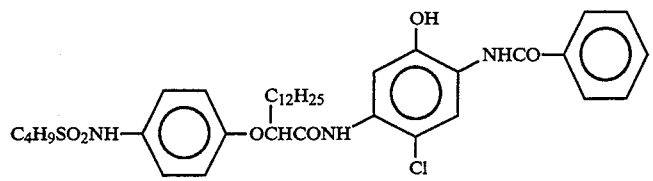
(C-21)
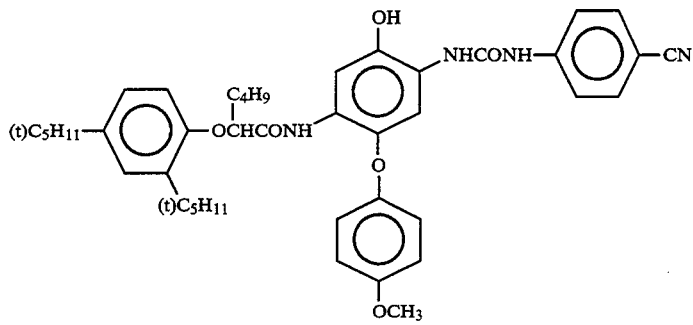
(C-22)
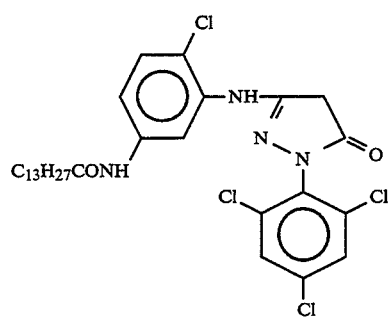
(M-1)
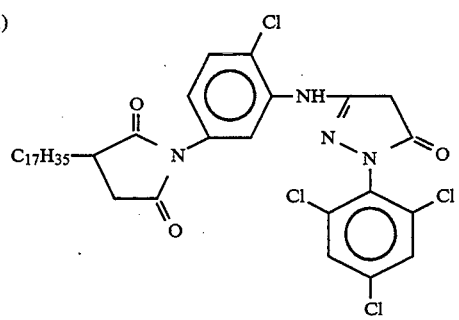
(M-2)
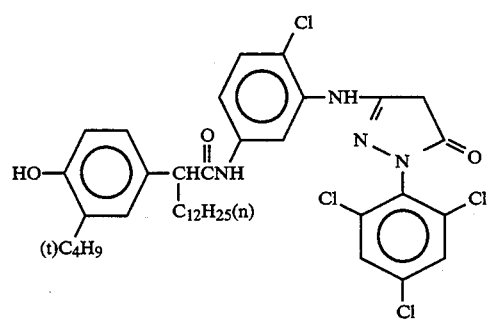
(M-3)
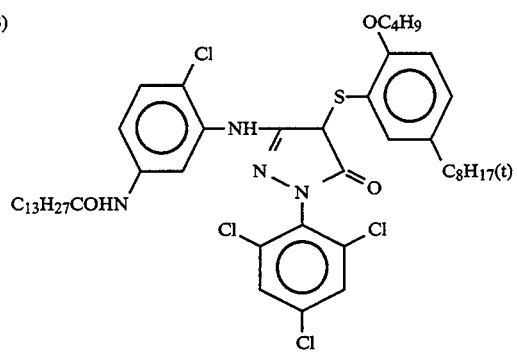
(M-4)
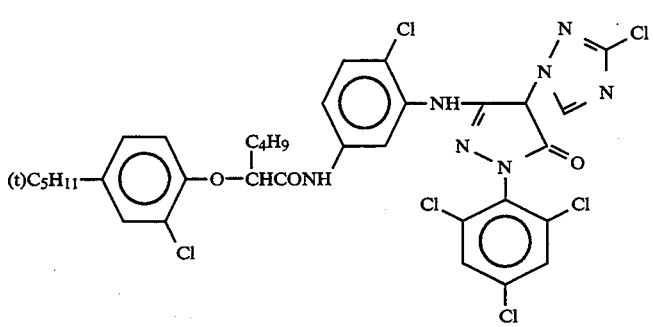
(M-5)

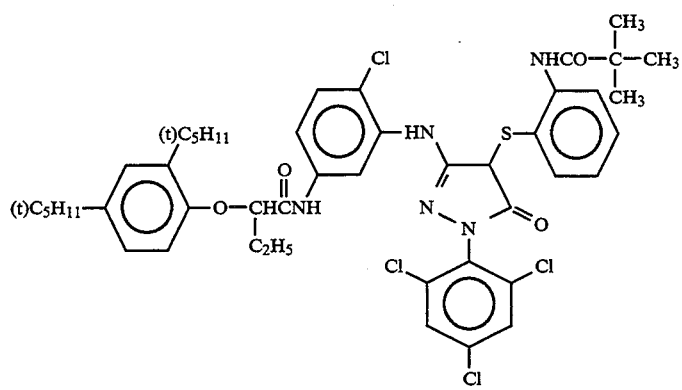
(M-6)
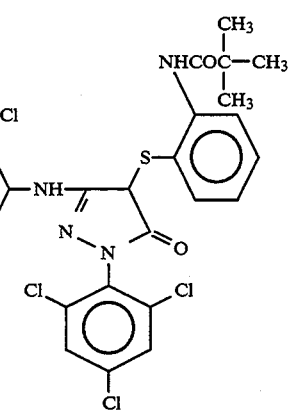
(M-7)
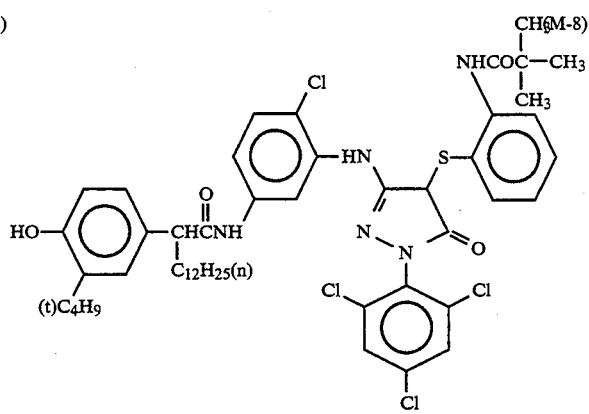
(M-8)

Structure (header):

$R_{60}$, $Y_{14}$ on pyrazole ring with $N-N$, $=N-C(R_{65})=NH$ substituent.

| Compound | $R_{60}$ | $R_{65}$ | $Y_{14}$ |
|---|---|---|---|
| M-9 | CH$_3$— | 4-OC$_8$H$_{17}$-3-(4-C$_8$H$_{17}$(t)-2-OC$_8$H$_{17}$-phenyl-NHSO$_2$-)phenyl with —CHCH$_2$NHSO$_2$— / CH$_3$ group | Cl |
| M-10 | " | 4-OCH$_2$CH$_2$OC$_6$H$_{13}$(n)-3-(4-C$_8$H$_{17}$(t)-phenyl)-CHCH$_2$NHSO$_2$—/CH$_3$ | " |
| M-11 | (CH$_3$)$_3$C— | 2-C$_5$H$_{11}$(t)-4-C$_5$H$_{11}$(t)-phenyl-O—CHCH$_2$NHCOCHO/C$_2$H$_5$/CH$_3$ | 4-CH$_3$-phenyl (−O−) |
| M-12 | 2-OCH$_3$-phenyl-O— | 2-OC$_8$H$_{17}$-5-C$_8$H$_{17}$(t)-phenyl-NHSO$_2$-(4-CH$_3$-phenyl) | 2-OC$_4$H$_9$-5-C$_8$H$_{17}$(t)-phenyl-S— |

-continued

| Compound | $R_{60}$ | $R_{65}$ | $Y_{14}$ |
|---|---|---|---|
| M-13 | $CH_3-$ | ![structure: -CHCH_2NHSO_2-phenyl(OCH_2CH_2OC_2H_5)-NHSO_2-phenyl(OC_8H_17)(C_8H_17(t))] with $-CH(CH_3)CH_2NHSO_2-$ linked to a phenyl bearing $OCH_2CH_2OC_2H_5$, and $NHSO_2$ to a second phenyl bearing $OC_8H_{17}$ and $C_8H_{17}(t)$ | Cl |
| M-14 | " | $-CH(CH_3)CH_2NHCOCHO(C_6H_{13}(n))$ attached to phenyl bearing $C_5H_{11}(t)$ and $C_5H_{11}(t)$ | " |
| M-15 | $CH_3-$ | $-C(CH_3)_2CH_2NHCOCHO(C_6H_{13}(n))$ attached to phenyl bearing $C_5H_{11}(t)$ and $C_5H_{11}(t)$ | Cl |
| M-16 | " | $-CH(CH_3)CH_2NHCO-$ phenyl bearing $OC_{12}H_{25}(n)$ | " |
| M-17 | " | $-CH(CH_3)CH_2NHCO-$ phenyl bearing $OC_{16}H_{33}(n)$ | " |

-continued

Structural formula:

$$\underset{R_{60}}{\overset{Y_{14}}{\diagdown}}\!\!\!\begin{array}{c}\text{N—NH}\\\text{\textbar\textbar}\\\text{N}\end{array}\!\!\!R_{65}$$

| Compound | $R_{60}$ | $R_{65}$ | $Y_{14}$ |
|---|---|---|---|
| M-18 | C₆H₅—OCH₂CH₂O— | 4-OCH₃-C₆H₄-O-[2-OC₈H₁₇,4-C₈H₁₇(t)-C₆H₃]-NHSO₂-CH₂CH₂NHSO₂— | 2-OC₄H₉,5-C₈H₁₇(t)-C₆H₃-S— |
| M-19 | CH₃CH₂O— | " | " |
| M-20 | [2-OC₈H₁₇,5-C₈H₁₇(t)-C₆H₃]-SO₂NH-C₆H₄-O(CH₂)₂O— | 2,4-Cl₂-C₆H₃— | Cl |
| M-21 | 2-OCH₃-C₆H₄-O— | [2-OC₈H₁₇(n),4-C₈H₁₇(t)-C₆H₃]-CH(CH₃)-CH₂NHSO₂— | " |
| M-22 | CH₃— | 4-[4-(4-HO-C₆H₄-SO₂)-C₆H₄-O]-CH(C₁₀H₂₁)-CONH-C₆H₄-(CH₂)₃— | Cl |

-continued

| Compound | R60 | R65 | Y14 |
|---|---|---|---|
| M-23 | " | (n)C6H13<br>CHCH2SO2(CH2)2<br>(n)C8H17 | " |
| M-24 | CH3—CH—CH3 | OC4H9—⟨phenyl⟩—SO2(CH2)3<br>C8H17(t) | " |
| M-25 | (CH—CH2)50(CH2—C)50<br>COOCH2OCH3  CH3  CH3 | CH3—CH—CH2NHSO2CH3 | " |
| M-26 | ⟨phenyl⟩—O— | (CH2)2NHSO2—⟨phenyl⟩<br>OC8H17  C8H17(t) | Cl |
| M-27 | CH3— | ⟨phenyl⟩—OCH2—⟨phenyl⟩—SO2—⟨phenyl⟩—NHCOCHO<br>CH3  CH3  (n)C10H21<br>CH3 | " |
| M-28 | (CH3)3C— | CH3—⟨phenyl⟩—NHCOCHO—⟨phenyl⟩—C5H11(t)<br>CH3  C5H11(t)<br>C4H9(n) | " |

-continued

| Compound | $R_{60}$ | $R_{65}$ | $Y_{14}$ |
|---|---|---|---|
| M-29 | 2,5-dimethoxy-4-methylphenyl (OCH$_3$, CH$_3$, OCH$_3$) | -(CH$_2$)$_3$O-[3,5-di-t-C$_5$H$_{11}$-phenyl] | Cl |
| M-30 | CH$_3$— | -CH(C$_2$H$_5$)-N(n-C$_{18}$H$_{37}$)COCH$_2$CH$_2$COOH | " |

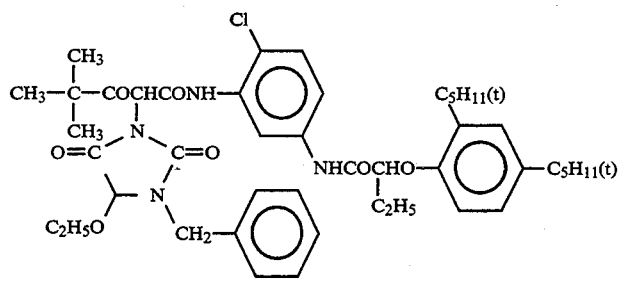
(Y-1)
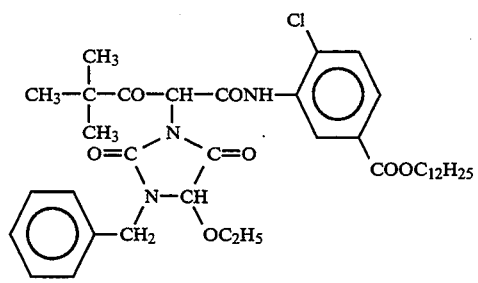
(Y-2)
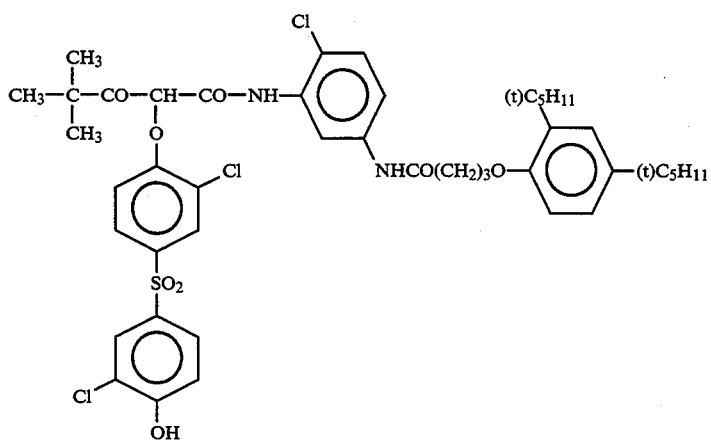
(Y-3)
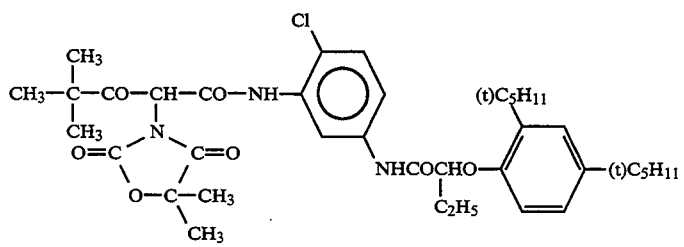
(Y-4)
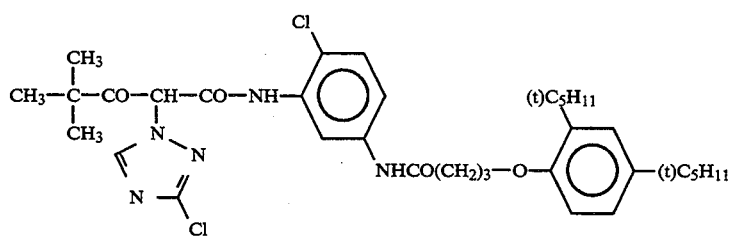
(Y-5)

-continued

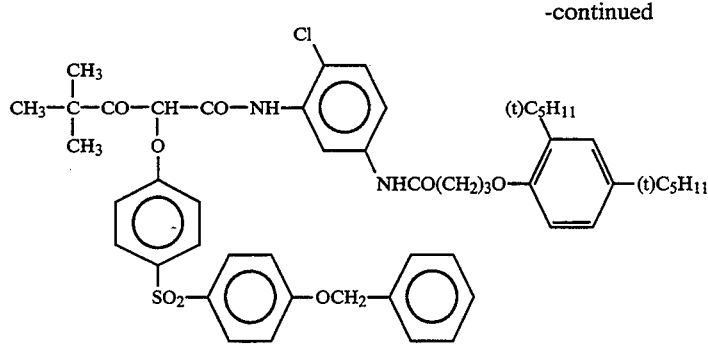

(Y-6)

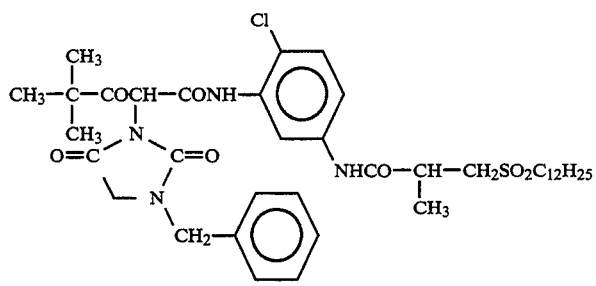

(Y-7)

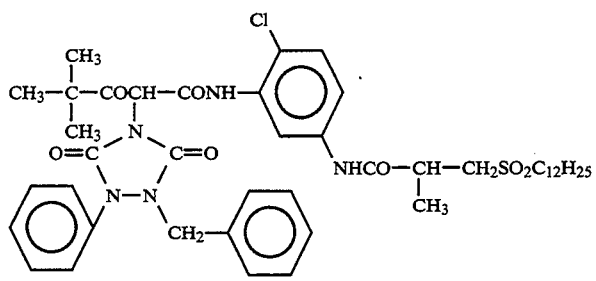

(Y-8)

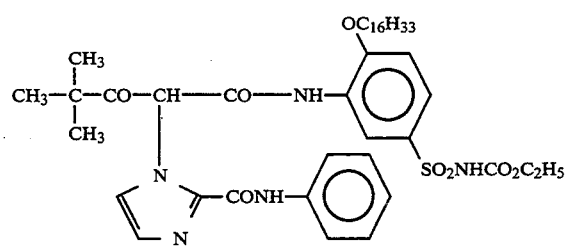

(Y-9)

The couplers represented by general formulae (C-I) to (Y) in an amount of 0.1 to 1.0 mol, preferably 0.1 to 0.5 mol per mol of silver halide are incorporated in silver halide emulsions which constitute light-sensitive layers.

In the present invention, the couplers can be added to the light-sensitive layers by known methods. Generally, the couplers can be added by conventional oil-in-water dispersion method known as oil protect method wherein the couplers are dissolved in a solvent and the resulting solution is emulsified and dispersed in an aqueous gelatin solution containing a surfactant. Alternatively, water or an aqueous gelatin solution is added to a coupler solution containing a surfactant, and an oil-in-water dispersion is formed by phase reversal. Alkali-soluble couplers can be dispersed by Fisher dispersion method. After low-boiling organic solvents are removed from the coupler dispersion by distillation, noodle washing, ultra-filtration, etc., the residue may be mixed with the emulsion.

It is preferred that water-insoluble high-molecular compounds and/or high-boiling organic solvents having a dielectric constant (25° C.) of 2 to 20 and a refractive index (25° C.) of 1.5 to 1.7 are used as dispersion medium for the couplers.

High-boiling organic solvents represented by the following general formulae (A) to (E) are preferred as said high-boiling organic solvents.

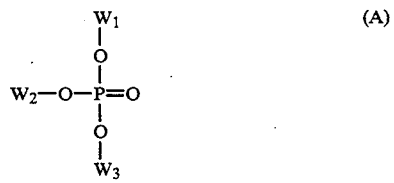

(A)

(B)

(C)

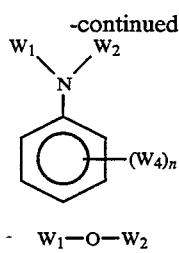

$$W_1\text{—}O\text{—}W_2 \quad (E)$$

In the above formulae, $W_1$, $W_2$ and $W_3$ are each a substituted or unsubstituted alkyl, cycloalkyl, alkenyl, aryl or heterocyclic group; $W_4$ is $W_1$, $OW_1$ or $SW_1$; and n is an integer of from 1 to 5. When n is 2 or greater, $W_4$ may be the same or different groups. In the formula (E), $W_1$ and $W_2$ may be combined together to form a condensed ring.

In addition to the above-described high-boiling organic solvents represented by general formulae (A) to (E), compounds which have a melting point of not higher than 100° C. and a boiling point of not lower than 140° C. and are water-immiscible can be used as high-boiling organic solvents, so long as they are good solvents for the couplers. The high-boiling organic solvents have a melting point of preferably not higher than 80° C. and a boiling point of preferably not lower than 160° C., more preferably not lower than 170° C.

The details of these high-boiling organic solvents are described in the specification of JP-A-62-215272 (pages 137, right-hand lower column to page 144, right-hand upper column).

The couplers are impregnated with loadable latex polymer (e.g., described in U.S. Pat. No. 4,203,716) in the presence or absence of said high-boiling organic solvent, or dissolved in a water-insoluble, but organic solvent-soluble polymer and can be emulsified in an aqueous solution of hydrophilic colloid. Preferably, homopolymers or copolymers described in WO 88/00723 (pages 12 to 30) are used. Particularly, acrylamide polymers are preferred from the viewpoint of dye image stability, etc.

The light-sensitive materials prepared by the present invention may contain hydroquinone derivatives, aminophenol derivatives, gallic acid derivatives, ascorbic acid derivatives, etc. as color fogging inhibitors.

The light-sensitive materials of the present invention may contain various anti-fading agents. Examples of the organic anti-fading agents for cyan, magenta and/or yellow images include hydroquinones, 6-hydroxychromans, 5-hydroxycoumarans, spiro-chromans, hindered phenols such as bisphenols and p-alkoxyphenols, gallic acid derivatives, methylenedioxybenzenes, aminophenols, hindered amines and ethers or ester derivatives obtained by silylating or alkylating phenolic hydroxyl group of the above-described compounds. Further, metal complexes such as (bis-salicyl-aldoximato)nickel complex and (bis-N,N-dialkyldithiocarbamato)nickel, etc. can also be used.

Examples of the organic anti-fading agents includes hydroquinones described in U.S. Pat. Nos. 2,360,290, 2,418,613, 2,700,453, 2,701,197, 2,728,659, 2,732,300, 2,735,765, 3,982,944 and 4,430,425, U.K. Patent 1,363,921, U.S. Pat. Nos. 2,710,801, 2,816,028, etc.; 6-hydroxychromans, 5-hydroxycoumarans and spiro-chromans described in U.S. Pat. Nos. 3,432,300, 3,573,050, 3,574,627, 3,698,909 and 3,764,337, JP-A-52-152225, etc.; spiro-indanes described in U.S. Pat. No. 4,360,589; p-alkoxyphenols described in U.S. Pat. No. 2,735,765, U.K. Patent 2,066,975, JP-A-59-10539, JP-B-57-19765, etc.; hindered phenols described in U.S. Pat. Nos. 3,700,455 and 4,228,235, JP-A-52-72224, JP-B-52-6623, etc.; gallic acid derivatives, methylenedioxybenzenes and aminophenols described in U.S. Pat. Nos. 3,457,079 and 4,332,886, JP-B-56-21144, etc.; hindered amines described in U.S. Pat. Nos. 3,336,135 and 4,268,593, U.K. Patents 1,326,889, 1,354,313 and 1,410,846, JP-B-51- 1420, JP-A-58-114036, JP-A-59-53846, JP-A-59-78344, etc.; and metal complexes described in U.S. Pat. Nos. 4,050,938 and 4,241,155, U.K. Patent 2,027,731 (A), etc. These compounds are used an amount of generally 5 to 100% by weight based on the amount of the corresponding coupler. These compounds are co-emulsified with the couplers and added to the emulsion layers. It is preferred that an ultraviolet light absorbing agent is introduced into a cyan color forming layer and both layers adjacent to the cyan color forming layer to prevent cyan color image from being deteriorated by heat and particularly light.

Examples of the ultraviolet light absorbing agents include aryl group-substituted benztriazole compounds described in U.S. Pat. No. 3,533,794; 4-thiazolidone compounds described in U.S. Pat. Nos. 3,314,794 and 3,352,681; benzophenone compounds described in JP-A-46-2784; cinnamic ester compounds described in U.S. Pat. Nos. 3,705,805 and 3,707,375; butadiene compounds described in U.S. Pat. No. 4,045,229; and benzoxidol compounds described in U.S. Pat. No. 3,700,455. If desired, ultraviolet absorbing couplers (e.g., α-naphthol cyan color forming couplers), ultraviolet light absorbing polymers, etc. may be used. These ultraviolet light absorbers may be incorporated in specific layers.

Among them, the aryl group-substituted benztriazole compounds are preferred.

It is preferred that the following compounds are used together with the couplers of the present invention, particularly pyrazoloazole couplers.

Namely, it is preferred that the couplers of the present invention are used in combination with a compound (F) and/or a compound (G), said compound (F) being chemically bonded to the aromatic amine developing agent left behind after color development to form a compound which is chemically inactive and substantially colorless and said compound (G) being chemically bonded to the oxidant of the aromatic amine developing agent left behind after color development to form a compound which is chemically inactive and substantially colorless. The compounds (F) and (G) are used either alone or in combination to thereby prevent stain from being formed by colored dye formed by the reaction of the couplers with the color development agents or the oxidants thereof left behind during storage after processing and to prevent other side effects from being caused.

Among the compounds (F), there are preferred compounds having a second-order reaction constant $k_2$ (80° C. in trioctyl phosphate) of 1.0 to $1 \times 10^{-5}$ l/mol·sec (in terms of the reaction of p-anisidine). The second-order reaction constant can be measured by the method described in JP-A-63-158545.

When $k_2$ is larger than the above upper limit, the compounds themselves become unstable and there is a possibility that the compounds are reacted with water or gelatin and decomposed, while when $k_2$ is smaller than the above lower limit, the reaction of the compounds with the aromatic amine developing agents left behind is retarded and there is a possibility that the side effects of the aromatic amine developing agents left behind cannot be prevented from being caused.

Among the compounds (F), there are more preferred compounds represented by the following general formula (FI) or (FII).

$$R_1-(A)_n-X \quad \text{(FI)}$$

In the above general formulae, $R_1$ and $R_2$ are each an aliphatic group, an aromatic group or a heterocyclic group; n is 0 or 1; A is a group which is reacted with the aromatic amine developing agent to form a chemical bond; X is a group which is eliminated by the reaction with the aromatic amine developing agent; B is hydrogen atom, an aliphatic group, an aromatic group, a heterocyclic group, an acyl group or a sulfonyl group; and Y is a group which accelerates the addition of the aromatic amine developing agent to the compound of general formula (FII). $R_1$ and X or Y and $R_2$ or B may be combined together to form a ring structure.

Typical examples of methods for chemically bonding the aromatic amine developing agents left behind are substitution reaction and addition reaction.

Concrete examples of the compounds represented by general formulae (FI) and (FII) are preferably those described in JP-A-63-158545, JP-A-62-283338, Japanese Patent Application No. 62-158342 (corresponding to JP-A-64-2042), and EP-A-277589 and EP-A-298321.

Among the compounds (G) which are chemically bonded to the oxidants of the aromatic amine developing agents left behind after color development to form a compound which is chemically inactive and substantially colorless, compounds represented by the following general formula (GI) are more preferred.

$$R-Z \quad \text{(GI)}$$

In the above formula, R represents an aliphatic group, an aromatic group or a heterocyclic group; and Z represents a nucleophilic group or a group which is decomposed in the light-sensitive material to release a nucleophilic group. Among the compounds of general formula (GI), there are preferred compounds where Z is a group having a Pearson's nucleophilic $^nCH_3I$ value [R. G. Pearson, et al., *J. Am. Chem. Soc.*, 90, 319 (1968)] of 5 or above or a group derived therefrom.

Preferred examples of the compounds represented by general formula (GI) are described in EP-A-255722, JP-A-62-143048, JP-A-62-229145, Japanese Patent Application Nos. 63-136724, 62-214681 and 62-158342 (corresponding to JP-A-1-230039, JP-A-1-57259 and JP-A-64-2042, respectively) and EP-A-277589, EP-A-298321, etc.

The details of the combinations of the compounds (G) with the compounds (F) are described in EP-A-277589.

The hydrophilic colloid layers of the light-sensitive materials of the present invention may contain ultraviolet light absorbing agents as described above.

The light-sensitive materials of the present invention may contain colloidal silver or dyes for purpose of preventing irradiation and halation, particularly for purpose of separating spectral sensitivity distribution of each light-sensitive layer and ensuring safety against safelight in the region of visible wavelength. Examples of the dyes include oxonol dyes, hemioxonol dyes, styryl dyes, merocyanine dyes, cyanine dyes and azo dyes. Among them, oxonol dyes, hemioxonol dyes and merocyanine dyes are preferred.

Decolorizable dyes described in JP-A-63-3250, JP-A-62-181381, JP-A-62-123454, JP-A-63-197947, etc. can be used as dyes for red to infrared region. Dyes described in JP-A-62-39682, JP-A-62-123192, JP-A-62-158779, JP-A-62-174741, etc. and dyes obtained by introducing a water-soluble group into said dyes so as to allow the dyes to flow into processing solutions during processing, can be used for back layer. In the present invention, the dyes for use in infrared region may be those which are colorless and substantially do not absorb light in the visible wavelength region.

When the dyes for infrared region according to the present invention are mixed with silver halide emulsions spectral-sensitized to red to infrared wavelength region, there are caused problems that desensitization and fogging are caused, and the dyes themselves are sometimes adsorbed by silver halide grains to thereby cause low-intensive broad spectral sensitization. Accordingly, it is preferred that the dyes are substantially incorporated in only colloid layers excluding light-sensitive layers. For this reason, it is preferred that the dyes in non-diffusing form are contained in the predetermined colored layer. For this purpose, a ballast group is firstly introduced into the dyes to make the dyes nondiffusing. However, residual color or stain is liable to be formed. Secondly, the anionic dyes of the present invention are used in combination with polymers providing cation site or the polymer latex providing cation site. Thirdly, dyes which are insoluble in water having a pH of not higher than 7 and decolorized and dissolved out during processing, are dispersed in the form of fine particles to use them. Namely, the dyes are dissolved in low-boiling organic solvents or solubilized by using surfactants and then dispersed in an aqueous solution of hydrophilic colloid such as gelatin. Preferably, the solid of said dye is kneaded with an aqueous solution of a surfactant to mechanically form fine particles in a mill, and fine particles are dispersed in an aqueous solution of hydrophilic colloid such as gelatin.

Gelatin is preferred as a binder or protective colloid for the emulsion layers of the light-sensitive materials of the present invention. In addition thereto, other hydrophilic colloid alone or in combination with gelatin can be used.

Any of lime-processed gelatin and acid-processed gelatin can be used. The preparation of gelatin is described in more detail in Arthur, Weiss, *The Macromolecular Chemistry of Gelatin* (Academic Press 1964).

The light-sensitive material of the present invention comprises a support having thereon a yellow coupler-containing light-sensitive layer (YL), a magenta coupler-containing light-sensitive layer (ML), a cyan coupler-containing light-sensitive layer (CL), a protective layer (PL), an interlayer (IL) and optionally a colored layer which is decolorized during development, particularly an antihalation layer (AH). YL, ML and CL have spectral sensitivity suited to at least three kinds of light fluxes having different dominant wavelengths, respectively. YL, ML and CL are different in dominant sensitivity wavelength by at least 30 nm, preferably 50 to 100 nm from one another. There is a difference in sensitivity by 0.8 logE (quantity of light) between dominant sensitivity wavelength of one light-sensitive layer and dominant sensitivity wavelength of other light-sensitive layer. Preferably, there is a difference in sensitivity by at least 1.0 therebetween. Preferably, at least one layer of each light-sensitive layers has sensitivity in the region of wavelength longer than 670 nm. More preferably, at least more one layer has sensitivity in the region of longer wavelength than 750 nm.

For example, light-sensitive layers can be arbitrarily constituted as shown in the following Table. In Table, R represents that light-sensitive layer is red-sensitized; and IR-1 and IR-2 represent that light-sensitive layers are spectral-sensitized to different infrared wavelength regions, respectively.

persed therein and supports composed of a hydrophobic resin containing a light reflecting material dispersed therein, said light reflecting material being used to increase reflectance in the wavelength region of visible light.

Typical examples of the supports include baryta paper, polyethylene coated paper, polypropylene synthetic paper, transparent supports coated with a reflecting layer or containing a reflection material. Examples of the transparent supports include glass sheet, polyester films such as polyethylene terephthalate, cellulose triacetate or cellulose nitrate film, polyamide films, polycarbonate films, polystyrene films and vinyl chloride resins. These supports can be properly chosen according to the purpose of use.

|  |  | (1) | (2) | (3) | (4) | (5) |
|---|---|---|---|---|---|---|
| Protective Layer |  | PL | PL | PL | PL | PL |
| Light-sensitive Layer | Unit | YL = R<br>ML = IR − 1<br>CL = IR − 2<br>(AH) | YL = IR − 2<br>ML = IR − 1<br>CL = R<br>(AH) | YL = R<br>CL = IR − 1<br>ML = IR − 2<br>(AH) | ML = R<br>YL = IR − 1<br>CL = IR − 2<br>(AH) | CL = R<br>YL = IR − 1<br>ML = IR − 2<br>(AH) |
| Support |  |  |  |  |  |  |

|  |  | (6) | (7) | (8) | (9) |
|---|---|---|---|---|---|
| Protective Layer |  | PL | PL | PL | PL |
| Light-sensitive Layer | Unit | CL = R<br>ML = IR − 1<br>YL = IR − 2<br>(AH) | CL = IR − 2<br>ML = IR − 1<br>YL = R<br>(AH) | ML = IR − 2<br>CL = IR − 1<br>YL = R<br>(AH) | ML = R<br>CL = IR − 1<br>YL = IR − 2<br>(AH) |
| Support |  |  |  |  |  |

In the present invention, light-sensitive layers having spectral sensitivity in the region of longer wavelength than 670 nm can be imagewise exposed by laser beam. Accordingly, spectral sensitivity distribution is in the wavelength region of dominant sensitivity wavelength ±25 nm, preferably dominant sensitivity wavelength ±15 nm. In the region of longer wavelength than 670 nm, particularly infrared wavelength, however, the spectral sensitivity of the present invention is apt to be relatively broad. Accordingly, the spectral sensitivity distribution of the light-sensitive layer should be corrected by using dyes, preferably by fixing dyes to a specific layer. For this purpose, the dyes in a nondiffusing state are incorporated in the colloid layer so that the dyes can be decolorized during the course of development. First method therefor is the use of a dispersion of fine particles of solid dye which is substantially insoluble in water having a pH of 7 and is not soluble in water having a pH of not lower than 7. Second method is the use of an acid dye together with a polymer or polymer latex capable of providing cation site. Dyes represented general formulae (VI) and (VII) described in JP-A-63-197947 are useful for the first and second methods. Particularly, dyes having carboxyl group are useful for the first method.

Any of transparent films conventionally used for photographic materials, such as cellulose nitrate film and polyethylene terephthalate film and reflection type support can be used as supports in the present invention. For the purpose of the present invention, the reflection type support is preferable.

The term "reflection type support" as used herein refers to supports which enhance reflection properties to make a dye image formed on the silver halide emulsion layer clear. Examples of the reflection type support include supports coated with a hydrophobic resin containing a light reflecting material such as titanium oxide, zinc oxide, calcium carbonate or calcium sulfate dis- It is preferred that as the reflecting material, a white pigment is thoroughly kneaded in the presence of a surfactant or the surfaces of pigment particles are treated with a dihydric to tetrahydric alcohol.

The occupied area ratio (%) of fine particles of white pigment per unit area can be determined by dividing the observed area into adjoining unit areas (each unit area: 6 μm×6 μm) and measuring the occupied area ratio (%) (Ri) of the fine particles projected on the unit area. A coefficient of variation of the occupied area ratio (%) can be determined from a ratio (S/$\bar{R}$) of standard deviation S of Ri to the mean value ($\bar{R}$) of Ri. The number (n) of divided unit areas is preferably not smaller than 6. Accordingly, a coefficient of variation S/$\bar{R}$ can be determined by the following formula.

$$\sqrt{\frac{\sum_{i=1}^{n}(R_i - \bar{R})^2}{n-1}} \bigg/ \frac{\sum_{i=1}^{n} R_i}{n}$$

In the present invention, a coefficient of variation of the occupied area ratio (%) of the fine particles of the pigment is preferably not higher than 0.15, particularly preferably not higher than 0.12.

As the light-reflecting material, there can be used thin films of metals such as aluminum or alloys thereof and metals having specular reflecting properties or a diffuse reflection surface of the second kind as described in JP-A-63-118154, JP-A-63-24247, JP-A-63-24251 to JP-A-63-24253, JP-A-63-24255, etc.

It is preferred that the supports of the present invention are lightweight and thin and have nerve, because they are used as hard copy after the formation of image. Further, the supports are preferably composed of inexpensive materials. As the reflective supports, polyethylene-coated paper, synthetic paper, etc. of 10 to 250 μm, preferably 30 to 180 μm in thickness is preferred.

The photographic materials of the present invention can be applied to color negative films for photographing (general-purpose, movie, etc.), reversal color films (slide, movie, etc.), color photographic paper, color positive films (movie, etc.), direct color positive films, reversal color photographic paper, color light-sensitive materials for heat development, color photographic materials for photomechanical process (lith films, scanner films, etc.), color X-ray photographic materials (direct and indirect medical use, industrial use, etc.), color diffusion transfer photographic materials (DTR), etc.

The present invention is now illustrated in greater detail by reference to the following examples which, however, are not to be construed as limiting the invention in any way.

EXAMPLE 1

Synthesis of Compound (29)

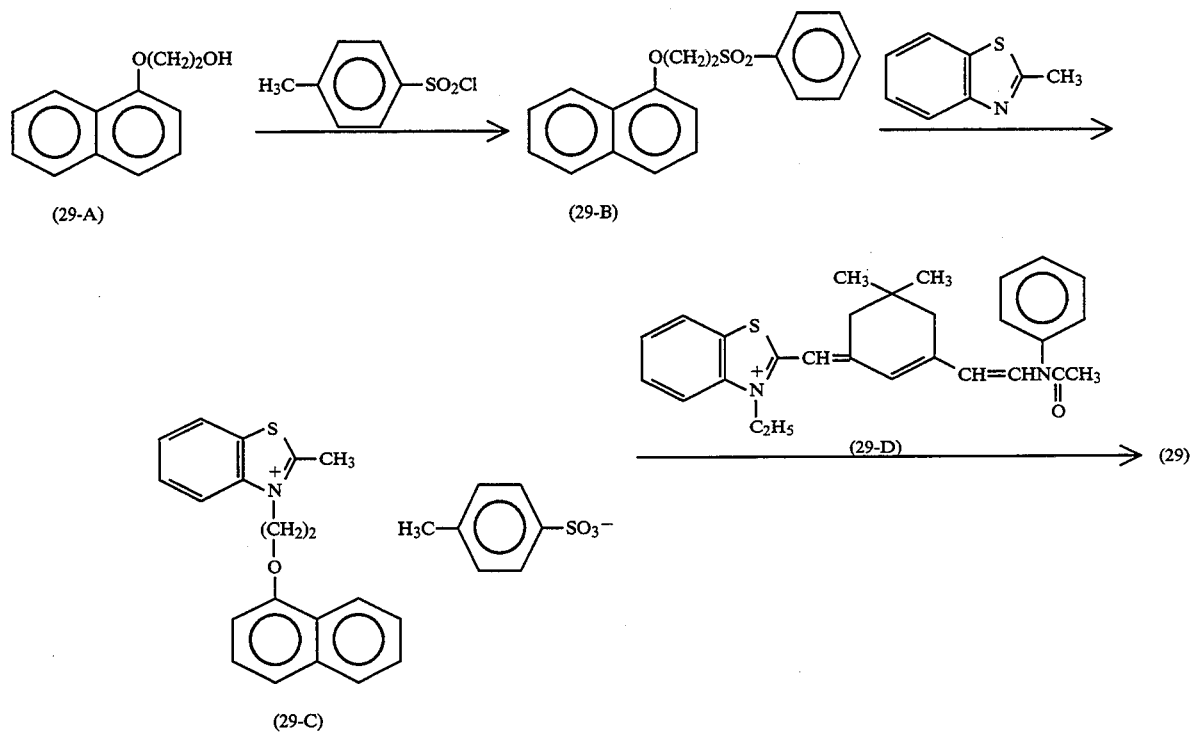

(29-A)

(29-B)

(29-C)

(a) Synthesis of Compound (29-B)

42.4 g of compound (29-A), 34.4 g of p-toluenesulfonic acid chloride and 200 ml of dioxane were stirred under ice cooling. 31.4 ml of triethylamine was added dropwise thereto while stirring them with ice cooling. The reaction mixture (solution) was stirred at room temperature for 2 hours and then introduced into ice water. The mixture was stirred. The precipitated crystal was recovered by filtration by means of suction and dried. Yield: 42.7 g (69%).

(b) Synthesis of Compounds (29-C) and (29)

1.25 g of 2-methylbenzthiazole and 3.73 g of compound (29-B) were stirred with heating at an external temperature of 150° to 160° C. for 4 hours to obtain compound (29-C). Without isolating the compound, 3 g of compound (29-D), 20 ml of pyridine and 2.3 ml of triethylamine were added thereto and the mixture was stirred with heating at an external temperature of 90° C. for 20 minutes. 100 ml of ethyl acetate was added thereto and the mixture was left to stand overnight. The precipitated crystal was collected by filtration by means of suction and recrystallized twice from methanol.

Yield: 1.1 g (17%) mp.: 253°–255° C. $\lambda_{max}^{MeOH}=766$ nm ($\epsilon=1.80\times10^5$)

EXAMPLE 2

Synthesis of Compound (32)

Compound (32) was synthesized in the same way as in the synthesis of compound (29) except that compound (32-A) was used in place of compound (29-A).

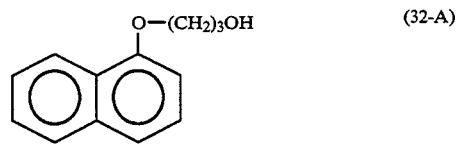

(32-A)

mp.: 163°–166° C. $\lambda_{max}^{MeOH}=767$ nm ($\epsilon=1.97\times10^5$)

EXAMPLE 3

Synthesis of Compound (33)

Compound (33) was synthesized in the same way as in the synthesis of compound (29) except that compound (33-A) was used in place of compound (29-A).

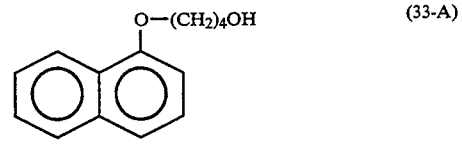

(33-A)

mp.: 125°–130° C. (dec) $\lambda_{max}^{MeOH}=765$ nm

EXAMPLE 4

Synthesis of Compound (31)

Compound (31) was synthesized in the same way as in the synthesis of compound (29) except that compound (31-A) was used in place of compound (29-A).

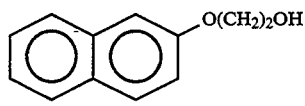

(31-A)

mp.: 213°–215° C. $\lambda_{max}^{MeOH}=766$ nm ($\epsilon = 1.65 \times 10^5$)

EXAMPLE 5

Synthesis of Compound (30)

(a)

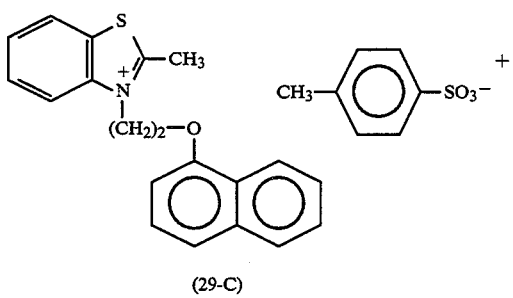

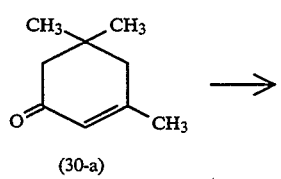

(30-a)

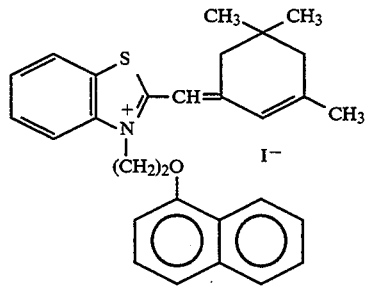

(30-b)

25 g (50.9 mM) of compound (29-C) and 21 g (153 mM) of compound (30-a) were stirred with heating at an external temperature of 140° C. for 24 hours. To the reaction mixture was added 23 g (153 mM) of NaI. Further, H$_2$O and chloroform were added thereto to conduct extraction. After the chloroform layer was dried over Na$_2$SO$_4$, the solvent was distilled off under reduced pressure. The residue was purified by means of silica gel column chromatograph (elution with methanol/chloroform=¼). Yield: 10.72 g (37%)

(b)

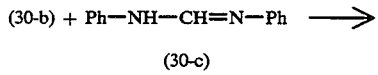

(30-c)

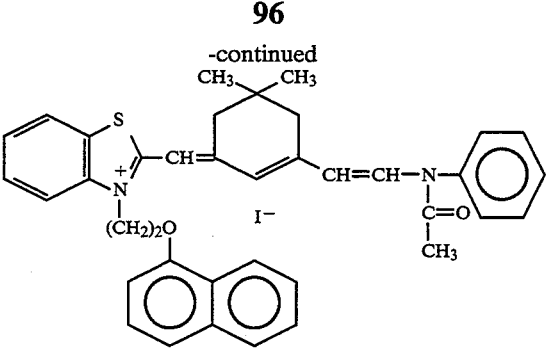

(30-d)

10.7 g (18.9 mM) of compound (30-b), 9.3 g (47 mM) of compound (30-c) and 40 ml of acetic anhydride were refluxed with heating for 3 hours. Hexane was added to the reaction mixture, and the precipitated crystal was recovered by filtration by means of suction.

Yield: 7.25 g (51%)

(c): (30-d)+(29-c)→(30)

2.5 g (4.4 mM) of compound (30-d), 1.73 g (3.5 mM) of compound (29-c), 15 ml of pyridine and 2 ml of triethylamine were stirred with heating at an external temperature of 90° C. for 20 minutes. Ethyl acetate was added to the reaction mixture, and the precipitated crystal was recovered by filtration by means of suction and purified by means of silica gel column chromatography (elution with methanol/chloroform=¼)

Yield: 0.31 g (8%) mp.: 209°–211° C. $\lambda_{max}^{MeOH}=771$ nm ($\epsilon = 2.15 \times 10^5$)

EXAMPLE 6

Synthesis of Compound (41)

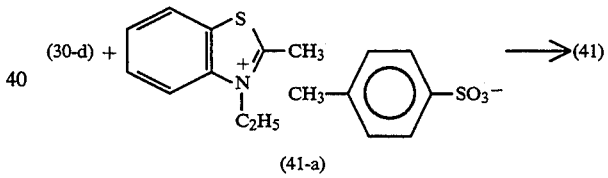

(41-a)

2.5 g (4.4 mM) of compound (30-d), 1.54 g (4.4 mM) of compound (41-a), 15 ml of pyridine and 2 ml of triethylamine were stirred with heating at an external temperature of 90° C. for 20 minutes. Ethyl acetate was added to the reaction mixture. The formed harz-like material was purified by means of silica gel column chromatography (elution with methanol/chloroform=¼).

Yield: 100 mg (3%) mp.: 166°–168° C. (dec) $\lambda_{max}^{MeOH}=768$ nm ($\epsilon = 1.95 \times 10^5$)

EXAMPLE 7

Synthesis of Compound (37)

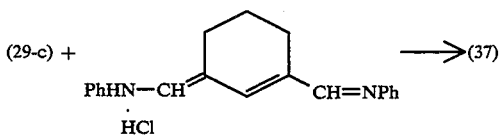

3 g (6.2 mM) of compound (29-c), 1 g (3.1 mM) of compound (37-a), 1.85 g of NaI, 50 ml of methanol and 1.9 ml (13.6 mM) of triethylamine were stirred at room temperature for 3 hours. The precipitated crystal was recovered by filtration by means of suction and thoroughly washed with water. The resulting crystal was heated in methanol/chloroform to dissolve it completely. After filtration by gravity, the filtrate was distilled under reduced pressure to a certain degree. The precipitated crystal was recovered by filtration by means of suction. The same purification operation was conducted once more.

Yield: 0.5 g (19%) mp.: 248°–250° C. $\lambda_{max}^{MeOH}=775$ nm ($\epsilon=2.61\times10^5$)

EXAMPLE 8

There was prepared a tabular silver iodobromide emulsion (average diameter: 0.82 μm, average diameter/thickness: 11.2, pAg: 8.2, pH: 6.5) which was gold-sulfur sensitized according to the method described in Example 1 of JP-A-60-131533. Compounds indicated in Table 1 were added to the emulsion at 40° C. Subsequently, sodium salt of 2,4-dichloro-6-hydroxy-1,3,5-triazine as a hardening agent for gelatin was added thereto. The resulting emulsion was coated on the surface of a cellulose triacetate support. In the above coating, a protective layer mainly composed of gelatin containing a surfactant and the aforesaid hardening agent was coated simultaneously with the emulsion layer as the upper layer on the emulsion layer. Each of the thus-prepared samples was divided into three groups. One group was stored at −30° C. for one year and another group was stored under natural environmental conditions for one year. The remaining one group was stored at −30° C. and then at 50° C. and 80% RH for 3 days before exposure. These three groups of the samples were subjected to exposure for sensitometry through a sharp cut filter transmitting light having longer wavelength than 520 nm by using FWH sensitometer (equipped with ultraviolet light absorbing filter, tungsten light source, color temperature: 2854° K., manufactured by Fuji Photo Film Co., Ltd.). These samples were developed with the developing solution described hereinafter, bleached, washed with water and dried.

The fogged density and sensitivity of each of the processed samples were measured by using a densitometer manufactured by Fuji Photo Film Co., Ltd. The reciprocal of the amount of light required for giving a density of (fogged density+0.2) was referred to herein as sensitivity. The sensitivity in terms of the relative sensitivity, when the sensitivity of each sample stored at −30° C. is referred to as 100, is shown in Table 1. An increase or decrease in the fogged density, when the density of each sample stored at −30° C. is referred to as standard, is shown in Table 1.

The Composition of the Developing Solution

| Metol | 2.5 g |
|---|---|
| l-Ascorbic acid | 10.0 g |
| Potassium bromide | 1.0 g |
| Nabox | 35.0 g |
| Water to make | 1 liter |
| pH | 9.8 |

TABLE 1

| Sample No. | Polymethine Dye and Amount Added × 10⁻⁵ | mol/molAg | Stored at −30° C. Sensitivity (Standard) | Fog | Stored at 50° C. 80% RH for 3 Days Relative Sensitivity | Fog | Stored Under Natural Conditions for One Year Relative Sensitivity | Fog | |
|---|---|---|---|---|---|---|---|---|---|
| 1-1 | A-1 | 70 | 100 | 0.02 | 95 | 0.02 | 94 | 0.02 | Comp. Ex. |
| 1-2 | A-2 | 70 | 100 | 0.02 | 98 | 0.02 | 95 | 0.02 | " |
| 1-3 | (11) | 70 | 100 | 0.02 | 100 | 0.02 | 99 | 0.02 | Invention |
| 1-4 | A-3 | 1.0 | 100 | 0.02 | 65 | 0.04 | 55 | 0.03 | Comp. Ex. |
| 1-5 | A-4 | 1.0 | 100 | 0.02 | 81 | 0.03 | 68 | 0.02 | " |
| 1-6 | (29) | 1.0 | 100 | 0.02 | 93 | 0.02 | 85 | 0.02 | Invention |
| 1-7 | (31) | 1.0 | 100 | 0.02 | 98 | 0.02 | 79 | 0.02 | " |

It is apparent from Table 1 that the samples of the present invention less cause an increase or decrease in sensitivity with the passage of time. The degree of a decrease in the sensitivity of polymethine dyes A-3, A-4, (29) and (31) having $E_{ox}$ of 0.60 or lower ($V_{vs}SCE$) is high in comparison with polymethine dyes A-1, A-2 and (11) having $E_{ox}$ of higher than 0.60 ($V_{vs}SCE$). This tendency is remarkable with A-3 and A-4 in particular. However, the polymethine dyes of the present invention scarcely cause a decrease in sensitivity in comparison with A-3 and A-4. Accordingly, the present invention is a very useful technique.

A-1

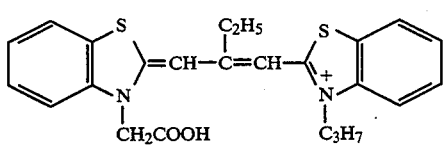

$E_{ox}=0.861$

A-2

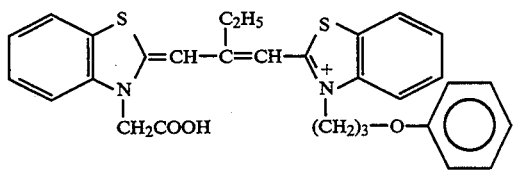

$E_{ox}=0.863$

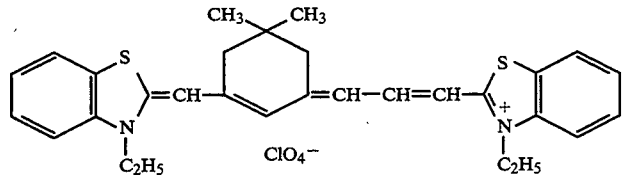

A-3

$E_{ox} = 0.374$

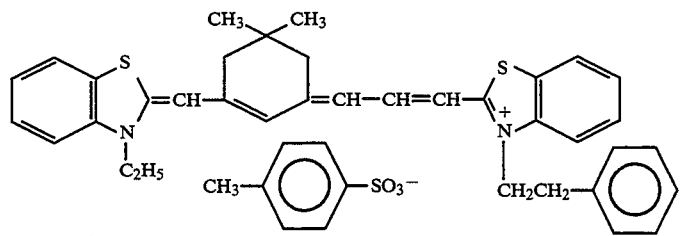

A-4

$E_{ox} = 0.375$

EXAMPLE 9

A cubic silver bromide emulsion was prepared according to the method described in Example 1 of JP-A-1-223441. The silver bromide grains of the resulting silver bromide emulsion were monodisperse grains having an average side length of 0.74 μm (a coefficient of variation: 10.6%). The emulsion was adjusted at 40° C. to pH=6.3 and pAg=8.4. Chloroauric acid and sodium thiosulfate were added thereto at 55° C., and ripening was carried out to thereby, effect gold-sulfur sensitization best. The compounds indicated in Table 2 were added thereto at 40° C. Further, 0.1 g of sodium salt of 2-hydroxy-4,6-dichloro-1,3,5-triazine and 0.1 g of sodium salt of dodecylbenzenesulfonic acid were added to the emulsion, each amount being per 1 kg of the emulsion. The emulsion and a protective layer were coated on a polyethylene terephthalate film support in the same manner as in Example 8.

Each of the thus-prepared coated samples was divided into three groups. One group was stored at −30° C. for 3 days and another group was stored at 50° C. and 80% RH for 3 days. The remaining one group was stored at room temperature under oxygen partial pressure of 10 atm for 3 days. In the same way as in Example 8, the samples were then subjected to exposure for sensitometry and processed. Sensitivity was measured. The reciprocal of the amount of light required for giving a density of (fogged density+0.2) was referred to herein as sensitivity. The results are shown in Table 2. The sensitivity in terms of the relative sensitivity, when the sensitivity of each sample stored at −30° C. is referred to as 100, is shown in Table 2.

TABLE 2

| Sample No. | Compound and Amount Added (×10⁻⁴ mol/mol Ag) | | | | Relative Sensitivity | | | |
|---|---|---|---|---|---|---|---|---|
| | | | | | Stored at −30° C. (Standard) | Stored at 50° C. 80% RH for 3 Days | Stored Under Oxygen Partial Pressure of 10 atm for 3 Days | |
| 2-1 | A-5 | 0.45 | | | 100 | 35 | 44 | Comp. Ex. |
| 2-2 | (17) | 0.45 | | | 100 | 76 | 76 | Invention |
| 2-3 | (17) | 0.45 | (V-6) | 3.0 | 100 | 91 | 78 | " |
| 2-4 | A-6 | 0.05 | | | 100 | 68 | 48 | Comp. Ex. |
| 2-5 | A-6 | 0.05 | (V-3) | 3.0 | 100 | 81 | 49 | " |
| 2-6 | (41) | 0.05 | | | 100 | 87 | 72 | Invention |
| 2-7 | (41) | 0.05 | (V-3) | 3.0 | 100 | 98 | 76 | " |
| 2-8 | A-7 | 0.07 | | | 100 | 74 | 37 | Comp. Ex. |
| 2-9 | A-7 | 0.07 | (IV-1) | 3.4 | 100 | 89 | 62 | " |
| 2-10 | (44) | 0.07 | | | 100 | 87 | 74 | Invention |
| 2-11 | (44) | 0.07 | (IV-1) | 3.4 | 100 | 98 | 91 | " |

A-5

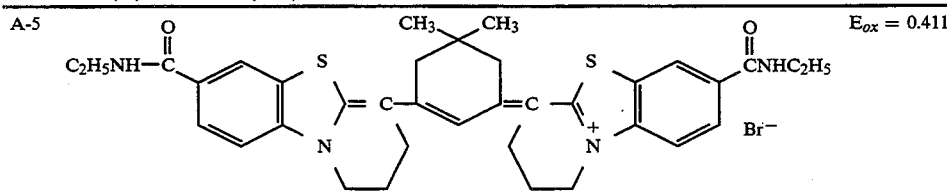

$E_{ox} = 0.411$

A-6

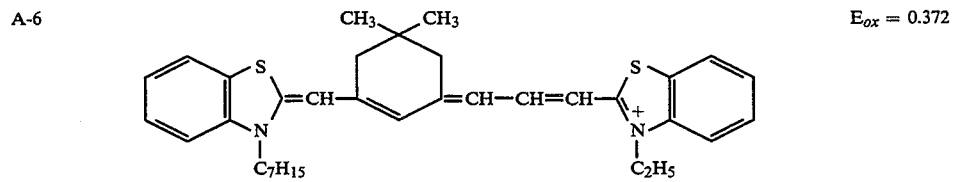

$E_{ox} = 0.372$

A-7

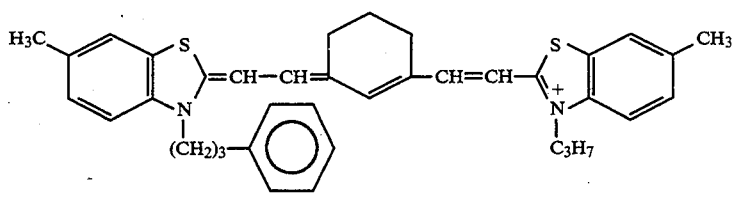

$E_{ox} = 0.273$

It will be understood from the results of Table 2 that the samples of the present invention scarcely cause a lowering in sensitivity even when stored under the above conditions. Further, when the compound V-6 or V-3 which is the compound of formula (V) is used as in the samples Nos. 2-3 and 2-7, the degree of a lowering in sensitivity can be further reduced when stored under high temperature and humidity of 50° C. and 80% RH. In the sample 2-11 containing the compound IV-1 (the compound of formula IV), a lowering in sensitivity is more inhibited in comparison with the sample 2-10 containing no compound IV-1 when stored under high temperature and humidity of 50° C. of 80% RH and when stored under oxygen partial pressure of 10 atm. The effect of the compounds of the present invention can be obtained even when used in combination with polymethine dyes which are outside the scope of the present invention. However, when the compounds are used in combination with the polymethine dyes of the present invention, a lowering in sensitivity can be remarkably inhibited under the above storage conditions.

EXAMPLE 10

Preparation of Emulsion 3.3 g of sodium chloride was added to a 3% aqueous solution of lime-processed gelatin, and 3.2 ml of N,N'-dimethylimidazolidine-2-thione (1% aqueous solution) was added thereto. To the resulting solution, there were added an aqueous solution containing 0.2 mol of silver nitrate and an aqueous solution containing 0.2 mol of sodium chloride and 15 μg of rhodium trichloride with vigorously stirring at 56° C. Subsequently, an aqueous solution containing 0.780 mol of silver nitrate and an aqueous solution containing 0.780 mol of sodium chloride and 4.2 mg of potassium ferrocyanide were added thereto with vigorously stirring at 56° C. Five minutes after the completion of the addition of the aqueous silver nitrate solution and the aqueous solution of the alkali halide, an aqueous solution containing 0.020 mol of silver nitrate and an aqueous solution containing 0.015 mol of potassium bromide, 0.005 mol of sodium chloride and 0.8 mg of potassium hexachloroiridate(IV) were added thereto with vigorously stirring at 40° C. Desalting and washing with water were carried out. Further, 90.0 g of lime-processed gelatin was added thereto and triethylthiourea was added to conduct chemical sensitization best.

The grain shape, grain size and grain size distribution of the resulting silver chlorobromide (A) were determined from electron microscope photograph. It was found that any of these silver halide grains was cube, grain size was 0.52 μm and a coefficient of variation was 0.08. The diameter of the grain was defined as the diameter of a circle having an area equal to the projected area of the grain. The grain size was represented by the average value of the diameters of the circles. The grain size distribution was a value obtained by dividing the standard deviation of the grain size by the mean grain size.

The silver halide crystal was examined by X-ray diffractometry to determine the halogen composition of emulsion grains. A monochromatized CuKα rays were used as a radiation source. The measurement was made at an angle of diffraction from (200) plane. The crystals having a uniform halogen composition had a diffraction pattern with a single peak, while the crystals having localized phases having different compositions had a diffraction pattern with a plurality of peaks corresponding to their compositions. The halogen composition of silver halide constituting the crystal could be determined by calculating lattice constant from an angle of diffraction of the measured peak. The results of the measurement showed that the silver chlorobromide emulsion (A) had such a diffraction pattern that in addition to a predominate peak of 100% silver chloride, there existed a broad pattern wherein the center existed around 70% silver chloride (30% silver bromide) and the foot reached nearly 60% silver chloride (40% silver bromide).

Preparation of Light-sensitive Material

A paper support (both sides being laminated with polyethylene) was coated with the following layers to prepare multi-layer color photographic paper. Coating solutions were prepared in the following manner.

Preparation of Coating Solution for First Layer 19.1 g of yellow coupler (ExY), 4.4 g of dye image stabilizer (Cpd-1) and 1.4 g of dye image stabilizer (Cpd-7) were dissolved in 27.2 ml of ethyl acetate and 8.2 g of solvent (Solv-1). The resulting solution was emulsified and dispersed in 185 ml of a 10% aqueous gelatin solution containing 8 ml of 10% sodium dodecylbenzenesulfonate. Separately, the following red-sensitive dyes (Dye-1) were added to the silver chlorobromide emulsion (A) to prepare an emulsion. The above emulsified dispersion and the emulsion were mixed and dissolved. A coating solution for first layer was prepared so as to give the following composition.

Coating solutions for the second layer through the seventh layer were prepared in the same manner as in the preparation of the coating solution for the first layer. Sodium salt of 2,4-dichloro-6-hydroxy-1,3,5-triazine was used as the hardening agent for gelatin in each year.

The following compounds were used as the spectral sensitizing dyes for the first layer (red-sensitive yellow color-forming layer).

(First layer: Red-sensitive yellow color-forming layer)
(Dye-1)

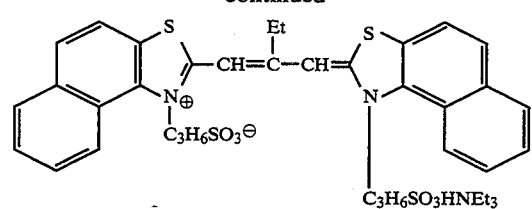

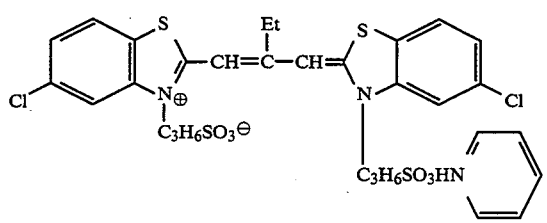

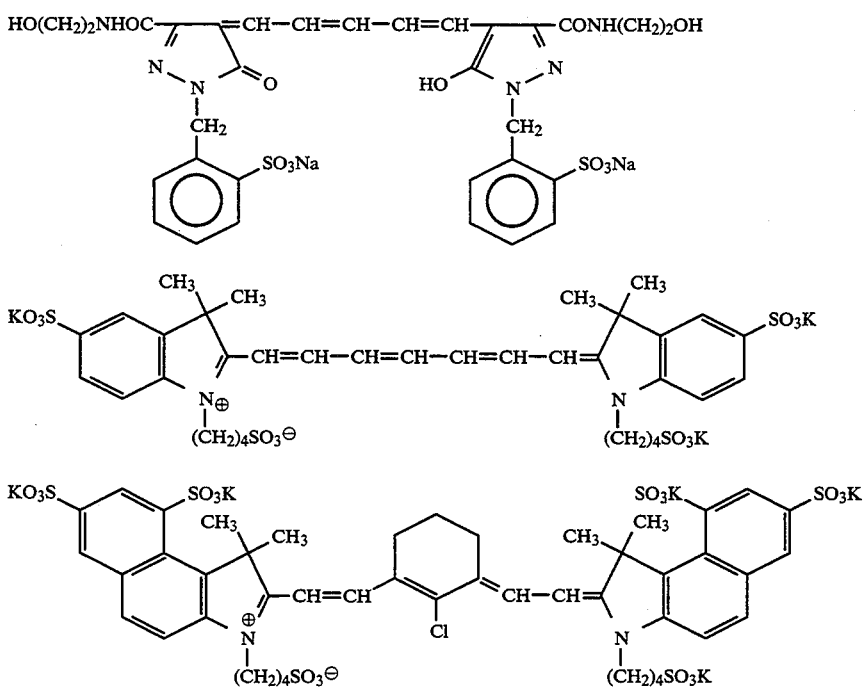

tive cyan color forming layer). The polymethine dyes in an amount of $2.5 \times 10^{-5}$ mol were added to the third layer, and the dyes in an amount of $0.6 \times 10^{-5}$ mol were added to the fifth layer, each amount being per mol of silver halide. Further, the compound IV-1 in an amount of $1.8 \times 10^{-3}$ mol per mol of silver halide was added when these polymethine dyes were used.

$8.0 \times 10^{-4}$ mol (per mol of silver halide) of 1-(5-methylureidophenyl)-5-mercaptotetrazole was added to each of the yellow color forming emulsion layer, the magenta color forming emulsion layer and the cyan color forming layer.

The following dyes were added to the emulsion layers to prevent irradiation.

$1.0 \times 10^{-4}$ mol and $1 \times 10^{-4}$ mol per mol of silver halide.

Polymethine dyes indicated in Tables 3 and 4 were added to the third layer (infrared-sensitive magenta color forming layer) and the fifth layer (infrared-sensi- Layer structure Each layer had the following composition. Numerals represents coating weight (g/m²). The silver halide emulsions are represented by coating weight in terms of silver.

Support

Polyethylene-laminated paper. [Polyethylene on the first layer side contains white pigment (TiO₂) and bluish dye (ultramarine)]

| First Layer: Red-sensitive Yellow Color Forming Layer | |
|---|---|
| The above silver chlorobromide emulsion (A) | 0.30 |
| Gelatin | 1.86 |
| Yellow coupler (ExY) | 0.82 |
| Dye image stabilizer (Cpd-1) | 0.19 |
| Solvent (Solv-1) | 0.35 |
| Dye image stabilizer (Cpd-7) | 0.06 |
| Second Layer: Color Mixing Inhibitor Layer | |
| Gelatin | 0.99 |
| Color mixing inhibitor (Cpd-5) | 0.08 |

-continued

| | |
|---|---|
| Solvent (Solv-1) | 0.16 |
| Solvent (Solv-4) | 0.08 |
| Third Layer: Infrared-sensitive Magenta Color Forming Layer | |
| Silver chlorobromide emulsion (A) | 0.12 |
| Gelatin | 1.24 |
| Magenta coupler (ExM) | 0.20 |
| Dye image stabilizer (Cpd-2) | 0.03 |
| Dye image stabilizer (Cpd-3) | 0.15 |
| Dye image stabilizer (Cpd-4) | 0.02 |
| Dye image stabilizer (Cpd-9) | 0.02 |
| Solvent (Solv-2) | 0.40 |
| Fourth Layer: Ultraviolet Light Absorbing Layer | |
| Gelatin | 1.58 |
| Ultraviolet light absorber (UV-1) | 0.47 |
| Color mixing inhibitor (Cpd-5) | 0.05 |
| Solvent (Solv-5) | 0.24 |
| Fifth Layer: Infrared-sensitive Cyan Color Forming Layer | |
| Silver chlorobromide emulsion (A) | 0.23 |
| Gelatin | 1.34 |
| Cyan coupler (ExC) | 0.32 |
| Dye image stabilizer (Cpd-6) | 0.17 |
| Dye image stabilizer (Cpd-7) | 0.40 |
| Dye image stabilizer (Cpd-8) | 0.04 |
| Solvent (Solv-6) | 0.15 |
| Sixth Layer: Ultraviolet Light Absorbing Layer | |
| Gelatin | 0.53 |
| Ultraviolet light absorber (UV-1) | 0.16 |
| Color mixing inhibitor (Cpd-5) | 0.02 |
| Solvent (Solv-5) | 0.08 |
| Seventh Layer: Protective Layer | |
| Gelatin | 1.33 |
| Acrylic-modified copolymer of polyvinyl alcohol (a degree of modification: 17%) | 0.17 |
| Liquid paraffin | 0.03 |

(EXY) Yellow Coupler

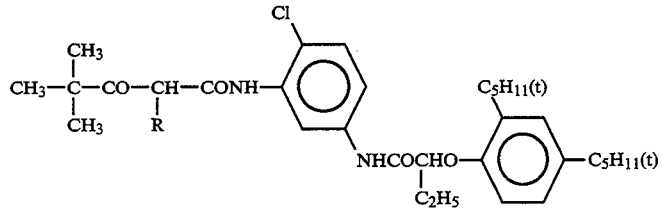

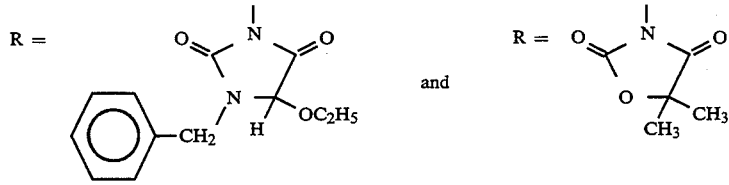

1:1 mixture (by molar ratio)

(ExM) Magenta Coupler

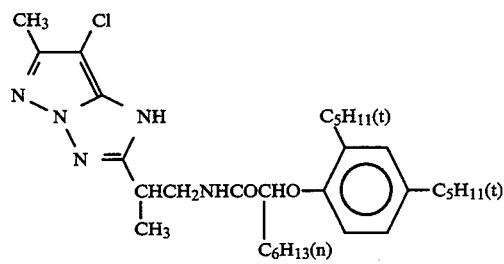

and 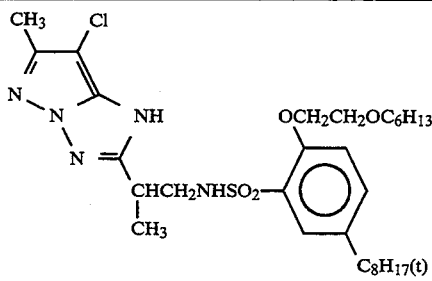
1:1 mixture (molar ratio)
(ExC) Cyan Coupler
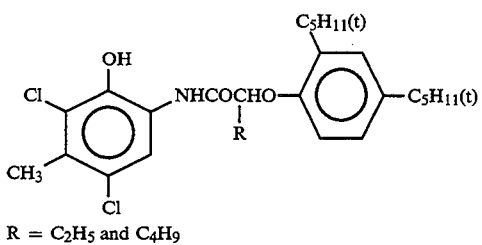
R = $C_2H_5$ and $C_4H_9$
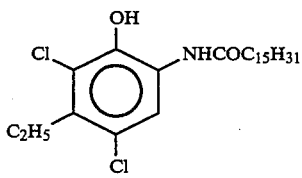
2:4:4 mixture (by molar ratio)
(Cpd-1) Dye Image Stabilizer
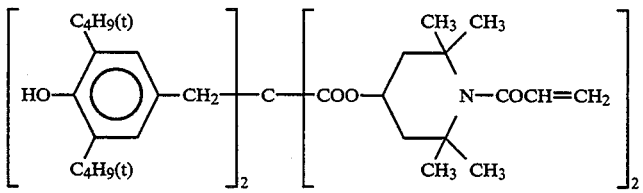
(Cpd-2) Dye Image Stabilizer
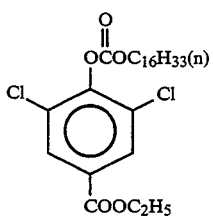
(Cpd-3) Dye Image Stabilizer
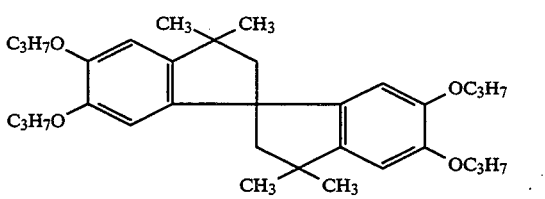
(Cpd-1) Dye Image Stabilizer
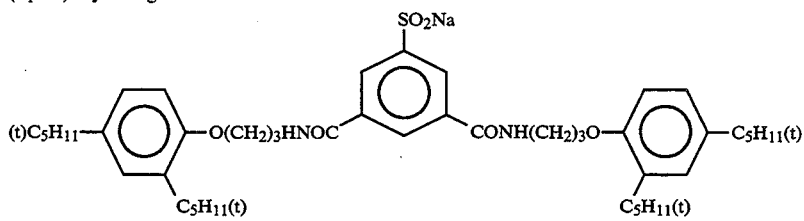

(Cpd-5) Color Mixig Inhibitor
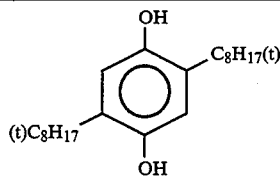
(Cpd-6) Dye Image Stabilizer
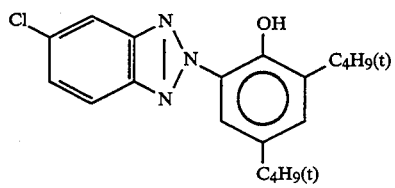
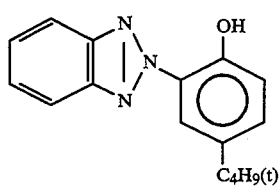
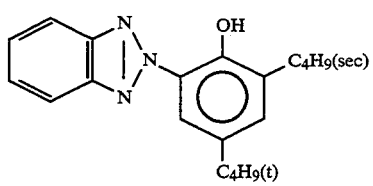
2:4:4 mixture (by weight)
(Cpd-7) Dye Image Stabilizer
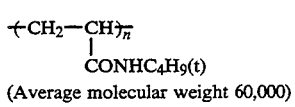
(Average molecular weight 60,000)
(Cpd-8) Dye Image Stabilizer
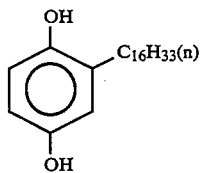
(Cpd-9) Dye Image Stabilizer
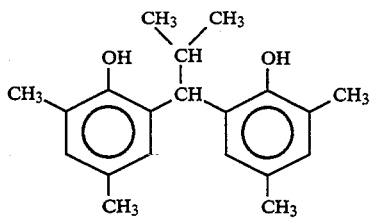
(UV-1) Ultraviolet Light Absorbent
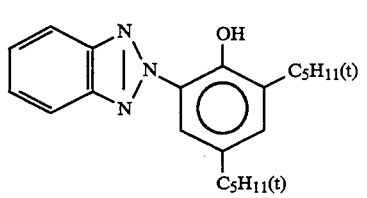
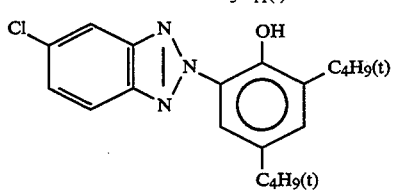

-continued

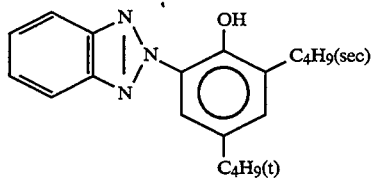
(4:2:4 mixture (by weight))

(Solv-1) Solvent

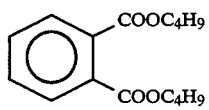

(Solv-2) Solvent

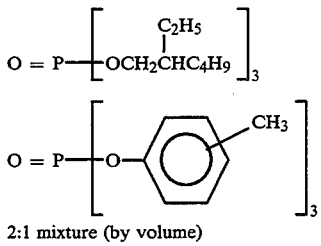
2:1 mixture (by volume)

(Solv-4) Solvent

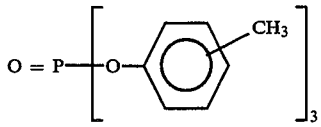

(Solv-5) Solvent

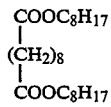

(Solv-6) Solvent

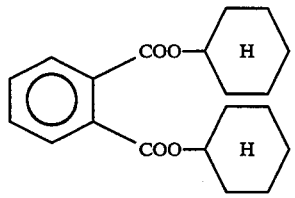

Each of the samples was divided into three groups. One group was stored at room temperature under oxygen partial pressure of 10 atm for 3 days, and another group was stored at 50° C. and 80% RH for 3 days. The remaining one group was stored at −30° C. in a container sealed with argon gas for 3 days. A device was assembled from semiconductor laser AlGaInP (oscillating wavelength: about 670 nm), semiconductor laser GaAlAs (oscillating wavelength: about 750 nm) and semiconductor laser GaAlAs (oscillating wavelength: about 830 nm) so that color photographic paper were scanned and exposed by laser beam in order by a rotating polyhedron, said photographic paper being transferred in the direction perpendicular to the scanning direction. The samples were exposed by using the device. Exposure amount was controlled by electrically controlling the exposure time and emission rate of the semiconductor laser.

The exposed samples were subjected to color development in the following processing stages by using a paper processor.

| Processing Stage | Temperature | Time | Replenisher* | Tank Capacity |
|---|---|---|---|---|
| Color development | 35° C. | 20 sec | 60 ml | 2 l |
| Bleaching-fixing | 30–35° C. | 20 sec | 60 ml | 2 l |
| Rinse (1) | 30–35° C. | 10 sec | — | 1 l |
| Rinse (2) | 30–35° C. | 10 sec | — | 1 l |
| Rinse (3) | 30–35° C. | 10 sec | 120 ml | 1 l |
| Drying | 70–80° C. | 20 sec | | |

*Replenishment rate being per m² of light-sensitive material.

(Three tank countercurrent system of rinse (3)→(1) was used)

Each processing solution had the following composition.

| | Tank Solution | Replenisher |
|---|---|---|
| Color Developing Solution | | |
| Water | 800 ml | 800 ml |
| Ethylenediamine-N,N,N,N-tetramethylenephosphonic acid | 1.5 g | 2.0 g |
| Potassium bromide | 0.015 g | — |

| | Tank Solution | Replenisher |
|---|---|---|
| Triethanolamine | 8.0 | 12.0 g |
| Sodium chloride | 4.9 g | — |
| Potassium carbonate | 25 g | 37 g |
| 4-Amino-3-methyl-N-ethyl-N-(3-hydroxypropyl)aniline di-p-toluenesulfonate | 12.8 g | 19.8 g |
| N,N-Bis(carboxymethyl)hydrazine | 5.5 g | 7.0 g |
| Brightening agent (WHITEX 4B, a product of Sumitomo Chemical Co., Ltd.) | 1.0 g | 2.0 g |
| Water to make | 1000 ml | 1000 ml |
| pH (25° C.) | 10.05 | 10.45 |
| Bleaching-fixing Solution (Tank solution and replenisher being the same) | | |
| Water | | 400 ml |
| Ammonium thiosulfate (700 g/l) | | 100 ml |
| Sodium sulfite | | 17 g |
| Ammonium ethylenediaminetetraacetato ferrate | | 55 g |
| Disodium ethylenediaminetetraacetate | | 5 g |
| Ammonium bromide | | 40 g |
| Water to make | | 1000 ml |
| pH (25° C.) | | 6.0 |

Rinsing Water
(Tank solution and replenisher being the same)

Ion-exchanged water (the concentration of each of calcium and magnesium ions being reduced to 3 ppm or below).

Cyan density, magenta density and yellow density of the developed samples were measured. The reciprocal of exposure amount giving a density of (fogged density+0.5) was referred to as sensitivity. The sensitivity in terms of relative sensitivity was determined.

The results of the magenta color forming layer (the third layer) are shown in Table 3, and the results of the cyan color forming layer (the fifth layer) are shown in Table 4.

The sensitivity of each color forming layer of each sample stored at −30° C. in argon is represented by relative sensitivity when the sensitivity of the corresponding color forming layer of the sample No. 3-1 stored at −30° C. in argon is referred to as 100. The sensitivity of each color forming layer of each sample stored at 50° C. and 80% RH for 3 days and the sensitivity of each color forming layer of each sample stored at room temperature under oxygen partial pressure of 10 atm for 3 days are represented by relative sensitivity when the sensitivity of the corresponding color forming layer of the corresponding sample stored at −30° C. in argon is referred to as 100.

It will be understood from Table 3 and Table 4 that the degree of a lowering in the sensitivity of the samples of the present invention which are stored under severe conditions is remarkably low in comparison with the samples containing polymethine dyes which have a similar structure to that of the present invention and are outside the scope of the present invention. Conventional infrared-sensitive polymethine dyes are very poor in stability, and commercially available silver halide photographic materials containing such dyes can keep sensitivity within only several months even when stored at a low temperature in a freezer. The reason why the sensitivity can be kept within only several months even when stored at a low temperature, is that conventional polymethine dyes are liable to be oxidized by air. The present inventors have made studies on the phenomenon of the oxidation by air and found that the lower the oxidation potential ($E_{ox}$) of the polymethine dye, the more the dye is oxidized, and when the oxidation potential is 0.60 or lower ($V_{vs}SCE$), the dye is readily oxidized. Even when the oxidation potential of the dyes of the present invention is much lower than 0.60 ($V_{vs}SCE$), the dyes of the present invention are very stable.

According to the present invention, there can be provided photographic materials which are even infrared-sensitive silver halide photographic materials which scarcely cause a lowering in sensitivity even when left to stand at room temperature over a long period of time as in conventional silver halide photographic materials.

TABLE 3

(Magenta Color Forming Layer)

| | | Relative Sensitivity | | | | |
|---|---|---|---|---|---|---|
| | | Stored at −30° C. in Argon | | Stored at 50° C. and 80% RH for 3 Days | Stored at Room Temp. under Oxygen Partial Pressure of 10 atm for 3 Days | |
| Sample No. | Polymethine Dye | Relative Sensitivity | Fog | | | |
| 3-1 | A-8 | 100 (Standard) | 0.04 | 68 | 42 | Comp. Ex. |
| 3-2 | (15) | 115 | 0.03 | 87 | 78 | Invention |
| 3-3 | A-9 | 135 | 0.02 | 76 | 52 | Comp. Ex. |
| 3-4 | (16) | 120 | 0.02 | 95 | 87 | Invention |

TABLE 4

(Cyan Color Forming Layer)

| | | Relative Sensitivity | | | | |
|---|---|---|---|---|---|---|
| | | Stored at −30° C. in Argon | | Stored at 50° C. and 80% RH for 3 Days | Stored at Room Temp. under Oxygen Partial Pressure of 10 atm for 3 Days | |
| Sample No. | Polymethine Dye | Relative Sensitivity | Fog | | | |
| 3-1 | A-10 | 100 (Standard) | 0.02 | 72 | 66 | Comp. Ex. |
| 3-2 | (34) | 115 | 0.02 | 95 | 89 | Invention |
| 3-3 | A-11 | 83 | 0.03 | 78 | 76 | Comp. Ex. |
| 3-4 | (38) | 98 | 0.02 | 98 | 93 | Invention |

TABLE 4-continued (Cyan Color Forming Layer)

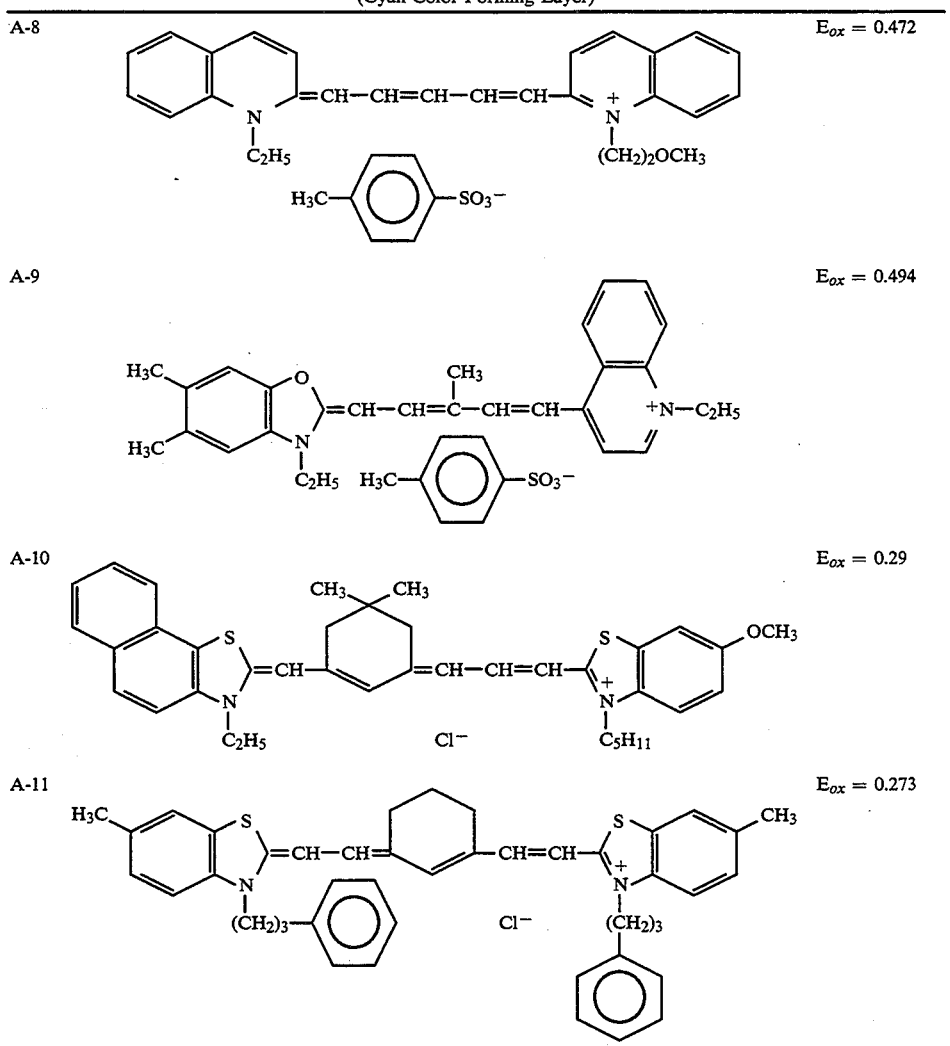

EXAMPLE 11

A silver chloride emulsion was prepared according to the method described in Example 1 of JP-A-63-239449. The prepared emulsion had a pH of 6.2 and a pAg of 7.2 and comprised monodisperse cubic silver chloride grains (a coefficient of variation: 9.1%) having a grain size of 0.46 μm. The emulsion was chemical-sensitized best with sodium thiosulfate.

Compounds indicated in Table 5 were added to the emulsion. Coated samples indicated in Table 5 were prepared by using the emulsion and the same emulsified coupler dispersion as the emulsified cyan coupler dispersion containing cyan coupler, etc. for the fifth layer shown in Example 10. In the sample No. 4-6 in Table 5, compound (18) was added 2 minutes before chemical sensitization after the addition of sodium thiosulfate, compound (IV-1) was added 15 minutes after the addition of sodium thiosulfate and the other compounds were added after 45 minutes.

A paper support (both sides being laminated with polyethylene) was used as the support. Coating weights were so set that the amount of silver was 0.35 g/m², that of coupler was 0.45 g/m² and that of gelation was 1.50 g/m². As the upper layer, a protective layer (gelatin: 1.50 g/m²) was provided. Sodium salt of 2,4-dichloro-6-hydroxy-1,3,5-triazine was used as the hardening agent for gelatin.

Each of the coated samples was divided into three groups. One group was sealed in an oxygen-impermeable bag purged with argon gas and stored at $-30°$ C. for one year. Another group was stored in the same manner as above, the bag was opened three days before the lapse of one year, and the samples were stored at 50° C. and 80% RH for 3 days. The remaining one group was left to stand indoors under natural conditions for one year.

The three groups of the samples were exposed by using tungsten sensitometer in the following manner. The sample Nos. 4-1 to 4-7 were exposed through a sharp cut filter transmitting light having longer wavelength than 660 nm. The sample Nos. 4-8 to 4-15 were exposed through a sharp cut filter transmitting light having longer wavelength than 720 nm. The sample Nos. 4-16 to 4-26 were exposed through a sharp cut filter transmitting light having longer wavelength than 780 nm.

The exposed samples were subjected to continuous processing (running test) in the following processing stages by using a paper processor until color developing solution in an amount of twice the capacity of the tank was replenished.

| Processing Stage | Temperature | Time | Replenisher* | Tank Capacity |
|---|---|---|---|---|
| Color development | 35° C. | 45 sec | 161 ml | 17 l |
| Bleaching-fixing | 30-30° C. | 45 sec | 215 ml | 17 l |
| Rinse (1) | 30-35° C. | 20 sec | — | 10 l |
| Rinse (2) | 30-35° C. | 20 sec | — | 10 l |
| Rinse (3) | 30-35° C. | 20 sec | 350 ml | 10 l |
| Drying | 70-80° C. | 60 sec | | |

*Replenishment rate being per m² of photographic material.

(Three tank countercurrent system of rinse (3)→(1) was used)
Each processing had the following composition.

| | Tank Solution | Replenisher |
|---|---|---|
| Color Developing Solution | | |
| Water | 800 ml | 800 ml |
| Ethylenediamine-N,N,N,N-tetramethylenephosphonic acid | 1.5 g | 2.0 g |
| Potassium bromide | 0.015 g | — |
| Triethanolamine | 8.0 g | 12.0 g |
| Sodium chloride | 1.4 g | — |
| Potassium carbonate | 25 g | 25 g |
| N-Ethyl-N-(β-methanesulfon-amidoethyl)-3-methyl-4-aminoaniline sulfate | 5.0 g | 7.0 g |
| N,N-Bis(carboxymethyl)—hydrazine | 5.5 g | 7.0 g |
| Brightening agent (WHITEX 4B, a product of Sumitomo Chemical Co., Ltd.) | 1.0 g | 2.0 g |
| Water to make | 1000 ml | 1000 ml |
| pH (25° C.) | 10.05 | 10.45 |
| Bleaching-fixing Solution | | |
| (Tank solution and replenisher being the same) | | |
| Water | 400 ml | |
| Ammonium thiosulfate (700 g/l) | 100 ml | |
| Sodium sulfite | 17 g | |
| Ammonium ethylenediaminetetraacetato ferrate | 55 g | |
| Disodium ethylenediaminetetraacetate | 5 g | |
| Ammonium bromide | 40 g | |
| Water to make | 1000 ml | |
| pH (25° C.) | 6.0 | |

Rinsing Solution
(Tank solution and replenisher being the same)
Ion-exchanged water (the concentration of each of calcium ion and magnesium ion being reduced to 3 ppm or below).

The cyan density of each of the developed samples was measured. The reciprocal of exposure amount giving a density of (Fog+0.5) is referred to as sensitivity. The sensitivity in terms of relative sensitivity is shown in Table 5. In Table 5, the sensitivity of the samples 4-1 to 4-7 stored at −30° C. is represented by relative sensitivity when the sensitivity of the sample No. 4-1 stored at −30° C. is referred to as 100. The sensitivity of the samples 4-8 to 4-15 is represented by relative sensitivity when the sensitivity of the sample No. 4-8 is referred to as 100. The sensitivity of the samples 4-16 to 4-26 is represented by relative sensitivity when the sensitivity of the sample No. 4-16 is referred to as 100. The sensitivity of the samples stored at 50° C. and 80% RH for 3 days and the sensitivity of the samples left to stand indoors under natural conditions for one year are represented by relative sensitivity when the sensitivity of each of the corresponding samples stored at −30° C. is referred to as 100.

It will be understood from Table 5 that the samples containing the polymethine dyes of the present invention scarcely cause a lowering in sensitivity when stored at 50° C. and 80% RH or when left to stand over a long period of time. Further, when used in combination with the compounds of general formula (IV), (V), (VI) or (VII), it will be understood that sensitivity becomes higher and stability is further increased.

TABLE 5

| Sample No. | Compound and Amount Added ×10⁻⁵ mol/mol Ag | | | | Relative Sensitivity Stored at −30° C. in Argon Relative Sensitivity | Fog | Stored at 50° C. and 80% RH for 3 Days | Left to Stand under Natural Conditions for One Year | |
|---|---|---|---|---|---|---|---|---|---|
| 4-1 | (A-12) | 12 | | | 100 (Standard) | 0.07 | 65 | 81 | Comp. Ex. |
| 4-2 | (14) | 12 | | | 129 | 0.07 | 83 | 93 | Invention |
| 4-3 | (A-13) | 12 | | | 132 | 0.07 | 56 | 79 | Comp. Ex. |
| 4-4 | (18) | 12 | | | 155 | 0.07 | 81 | 93 | Invention |
| 4-5 | (18) | 12 | IV-1 | 130 | 525 | 0.03 | 100 | 100 | " |
| | | | VI-6 | 40 | | | | | |
| 4-6 | (18) | 12 | IV-1 | 130 | 676 | 0.04 | 100 | 98 | Invention (18) was added before chemical sensitization |
| | | | VI-6 | 40 | | | | | |
| 4-7 | (18) | 12 | IV-1 | 130 | 671 | 0.04 | 100 | 100 | Invention |
| | | | VII-6 | 40 | | | | | |
| 4-8 | (A-8) | 2.0 | | | 100 (Standard) | 0.08 | 46 | 35 | Comp. Ex. |
| 4-9 | (21) | 2.0 | | | 129 | 0.07 | 68 | 62 | Invention |
| 4-10 | (A-14) | 2.0 | | | 148 | 0.08 | 51 | 27 | Comp. Ex. |
| 4-11 | (23) | 2.0 | | | 126 | 0.08 | 74 | 60 | Invention |
| 4-12 | (23) | 2.0 | V-3 | 20 | 417 | 0.06 | 87 | 62 | " |
| 4-13 | (23) | 2.0 | VI-6 | 40 | 646 | 0.07 | 81 | 59 | " |
| 4-14 | (23) | 2.0 | IV-1 | 130 | 269 | 0.04 | 83 | 83 | " |
| 4-15 | (23) | 2.0 | VII-1 | 40 | 640 | 0.07 | 80 | 57 | " |
| 4-16 | (A-15) | 0.7 | | | 100 (Standard) | 0.07 | 53 | 42 | Comp. Ex. |
| 4-17 | (50) | | | | 95 | 0.07 | 72 | 68 | Invention |
| 4-18 | (A-16) | | | | 138 | 0.07 | 62 | 46 | Comp. Ex. |
| 4-19 | (51) | | | | 129 | 0.06 | 76 | 74 | Invention |
| 4-20 | (45) | | | | 141 | 0.06 | 78 | 72 | |

TABLE 5-continued

| | | | | | | | |
|---|---|---|---|---|---|---|---|
| 4-21 | (A-17) | | 155 | 0.07 | 51 | 37 | Comp. Ex. |
| 4-22 | (35) | | 148 | 0.07 | 72 | 66 | Invention |
| 4-23 | (35) | V-3 | 617 | 0.07 | 85 | 65 | " |
| 4-24 | (35) | IV-1 | 331 | 0.06 | 87 | 81 | " |
| 4-25 | (35) | IV-1 VI-6 | 1230 | 0.06 | 98 | 87 | " |
| 4-26 | (35) | IV-1 VIII-1 | 1210 | 0.06 | 97 | 85 | Invention |

A-12     Elox = 0.59

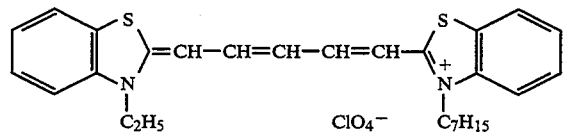

A-13     Elox = 0.50

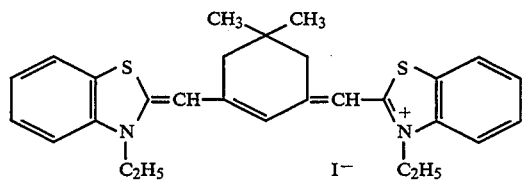

A-14     Elox = 0.40

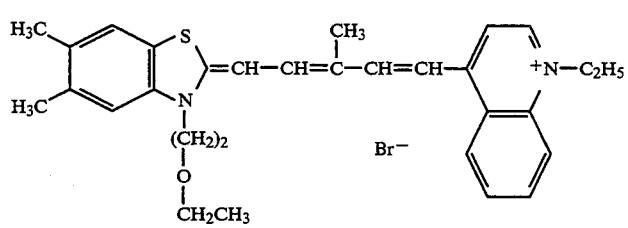

A-15     Elox = 0.35

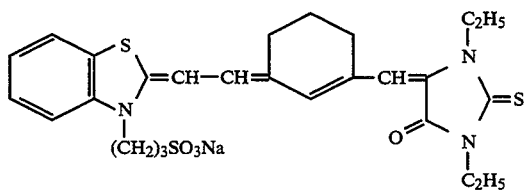

A-16     Elox = 0.34

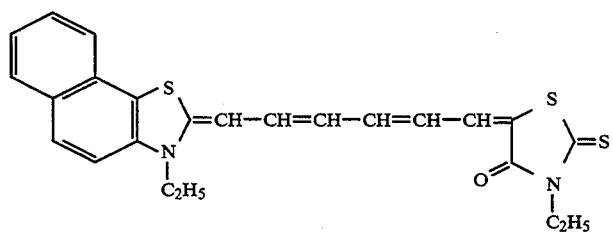

A-17     Elox = 0.30

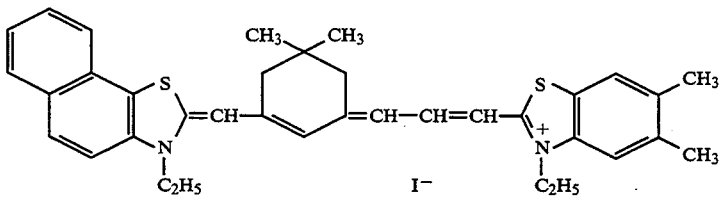

While the invention has been described in detail and with reference to specific embodiments thereof, it will be apparent to one skilled in the art that various changes and modifications can be made therein without departing from the spirit and scope thereof.

What is claimed is:

1. A silver halide emulsion which contains at least one of the methine dyes represented by the following general formula (I):

$$(MET)_{\overline{n_1}}[(Q)_{l_2}-Ar]_{l_3} \quad (I)$$

wherein Q represents a bivalent bonding group comprising at least one atom of carbon atom, nitrogen atom, sulfur atom and oxygen atom or an atomic group having at least one atom of carbon atom, nitrogen atom, sulfur atom and oxygen atom; Ar represents a group which has an aromatic character and derives from a polycyclic compound composed of 8 or more atoms excluding a nitrogen atom; $l_1$ represents 1; $l_2$ represents 0 or 1; and $l_3$ represents 1, 2, 3 or 4; and MET represents an atomic group having a hexamethinemerocyanine structure represented by the following general formula (II):

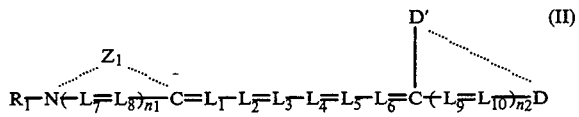

wherein $Z_1$ represents an atomic group required for forming a 5-membered or 6-membered nitrogen-containing heterocyclic ring; D and D' represent each an atomic group required for forming a non-cyclic or cyclic acidic nucleus; $R_1$ represents an alkyl group; $L_1$, $L_2$, $L_3$, $L_4$, $L_5$, $L_6$, $L_7$, $L_8$, $L_9$ and $L_{10}$ represent each a methine group, or each may be combined together with other methine groups to form a ring, or each may be combined together with an auxochrome to form a ring; $n_1$ and $n_2$ represent each 0 or 1; $M_1$ represents a counter ion for charge neutralization; and $m_1$ represents a number of 0 or greater which is required for neutralizing electric charge in the molecule represents an atomic group having a methine dye structure;

wherein the methine dyes represented by general formula (I) have an oxidation potential of 0.60 ($V_{vs}SCE$) or lower.

2. A silver halide emulsion containing at least one member of the methine dyes represented by general formula (I) as claimed in claim 1, and at least one member of the compounds represented by the following general formulae (IV), (V), (VI) and (VII):

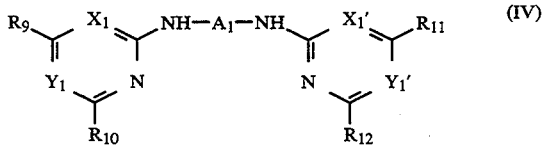

wherein $A_1$ represents a bivalent aromatic residue; $R_9$, $R_{10}$, $R_{11}$ and $R_{12}$ represent each a hydrogen atom, a hydroxyl group, an alkyl group, an alkoxy group, an aryloxy group, a halogen atom, a heterocyclic nucleus, a heterocyclic thio group, an arylthio group, an amino group, an alkylamino group, an arylamino group, an aralkylamino group, an aryl group or a mercapto group, each of which may optionally have one or more substituent groups, with the proviso that at least one of $A_1$, $R_9$, $R_{10}$, $R_{11}$ and $R_{12}$ is a group having sulfo group; and $X_1$, $Y_1$, $X_1'$ and $Y_1'$ represent each —CH= or —N= and at least one of $X_1$ and $Y_1$ and at least one of $X_1'$ and $Y_1'$ are —N=,

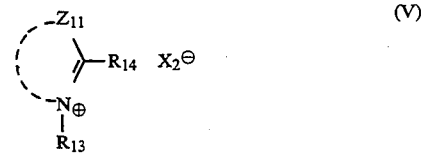

wherein $Z_{11}$ represents a non-metallic atomic group required for forming a 5-membered or 6-membered nitrogen-containing heterocyclic ring which may be condensed with a benzene ring or a naphthalene ring; $R_{13}$ represents a hydrogen atom, an alkyl group or an alkenyl group; $R_{14}$ represents a hydrogen atom or a lower alkyl group; and $X_2^\ominus$ represents an acid anion,

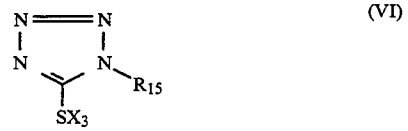

wherein $R_{15}$ represents an alkyl group, an alkenyl group or an aryl group; and $X_3$ represents a hydrogen atom, an alkali metal atom, an ammonium group or a precursor,

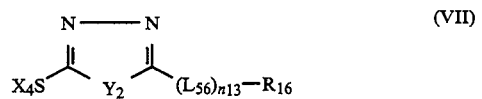

wherein $Y_2$ represents oxygen atom, sulfur atom, =NH or =N—$(L_{57})_{n14}$—$R_{17}$; $L_{56}$ and $L_{57}$ represent each a bivalent bonding group; $R_{16}$ and $R_{17}$ represent each a hydrogen atom, an alkyl group, an alkenyl group or an aryl group; $X_4$ represents a hydrogen atom, an alkali metal atom, an ammonium group or a precursor; and $n_{13}$ and $n_{14}$ represent each 0 or 1.

3. A silver halide emulsion as in claim 1, wherein Ar represents a group which has an aromatic character and derives from a polycyclic carbon compound whose ring is composed of 9 or more carbon atoms.

4. A silver halide emulsion as in claim 1, wherein Q represents a bivalent bonding group having not more than 20 carbon atoms, which is composed of an alkylene group, an arylene group, an alkenylene group, a sulfonyl group, a sulfinyl group, a thioether group, an ether group, a carbonyl group, a group of

(wherein $R^1$ is a hydrogen atom, an alkyl group or an aryl group) or a heterocyclic bivalent group or a combination of two or more of these groups.

5. A silver halide emulsion as in claim 1, wherein the methine dye is incorporated in the silver halide emulsion in an amount of $5 \times 10^{-7}$ to $5 \times 10^{-3}$ mol per mol of silver halide.

6. A silver halide emulsion as in claim 1, wherein the methine dye is incorporated in the silver halide emulsion in an amount of $1 \times 10^{-6}$ to $1 \times 10^{-3}$ mol per mol of silver halide.

7. A silver halide emulsion as in claim 2, wherein the compound represented by general formula (IV) is used in an amount of 0.01 to 5 g per mol of silver halide.

8. A silver halide emulsion as in claim 2, wherein the compound represented by general formula (IV) is used in a ratio by weight of the compound to the sensitizing dye of from 1/1 to 100/1.

9. A silver halide emulsion as in claim 2, wherein the compound represented by general formula (V) is used in an amount of 0.01 to 5 g per mol of silver halide.

10. A silver halide emulsion as in claim 2, wherein the methine dye represented by general formula (I) and the compound represented by general formula (V) are used in a ratio by weight of the dye of general formula (I) to the compound (V) of from 1/1 to 1/300.

11. A silver halide emulsion as in claim 2, wherein the compound represented by general formula (VI) or (VII) is used in an amount of $1\times10^{-5}$ to $5\times10^{-2}$ mol per mol of silver halide.

12. A silver halide emulsion which contains at least one of the methine dyes represented by the following general formula (I):

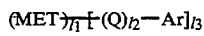  (I)

wherein Q represents a bivalent bonding group comprising at least one atom of carbon atom, nitrogen atom, sulfur atom and oxygen atom or an atomic group having at least one atom of carbon atom, nitrogen atom, sulfur atom and oxygen atom; Ar represents a group which has an aromatic character and derives from a polycyclic compound composed of 8 or more atoms excluding a nitrogen atom; $l_1$ represents 1; $l_2$ represents 0 or 1; and $l_3$ represents 1, 2, 3 or 4; and MET represents an atomic group having a hepta-methinecyanine structure represented by the following general formula (III):

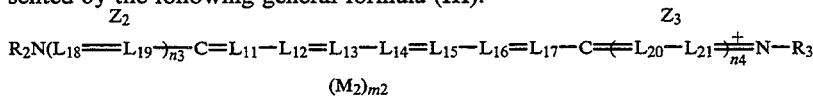

wherein $Z_2$ and $Z_3$ represent each an atomic group required for forming a 5-membered or 6-membered nitrogen-containing heterocyclic ring; $R_2$ and $R_3$ represent each an alkyl group; $L_{11}$, $L_{12}$, $L_{13}$, $L_{14}$, $L_{15}$, $L_{16}$, $L_{17}$, $L_{18}$, $L_{19}$, $L_{20}$ and $L_{21}$ represent each a methine group; or each may be combined together with an auxochrome to form a ring; $n_3$ and $n_4$ represent each 0 or 1; $M_2$ represents a counter ion for charge neutralization; and $m_2$ represents a number of 0 or greater which is required for neutralizing electric charge in the molecule;

wherein one group of $L_{12}$ and $L_{14}$, $L_{13}$ and $L_{15}$ or $L_{14}$ and $L_{16}$ is combined together to form a ring; and wherein the methine dyes represented by general formula (I) have an oxidation potential of 0.60 ($V_{vs}SCE$) or lower.

13. A silver halide emulsion containing at least one member of the methine dyes represented by general formula (I) as claimed in claim 12, and at least one member of the compounds represented by the following general formulae (IV), (V), (VI) and (VII):

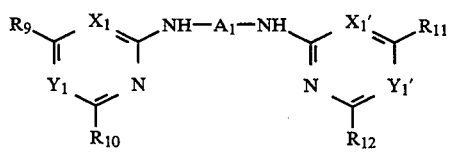  (IV)

wherein $A_1$ represents a bivalent aromatic residue; $R_9$, $R_{10}$, $R_{11}$ and $R_{12}$ represent each a hydrogen atom, a hydroxyl group, an alkyl group, an alkoxy group, an aryloxy group, a halogen atom, a heterocyclic nucleus, a heterocyclic thio group, an arylthio group, an amino group, an alkylamino group, an arylamino group, an aralkylamino group, an aryl group or a mercapto group, each of which may optionally have one or more substituent groups, with the proviso that at least one of $A_1$, $R_9$, $R_{10}$, $R_{11}$ and $R_{12}$ is a group having sulfo group; and $X_1$, $Y_1$, $X_1'$ and $Y_1'$ represent each —CH= or —N= and at least one of $X_1$ and $Y_1$ and at least one of $X_1'$ and $Y_1'$ are —N=,

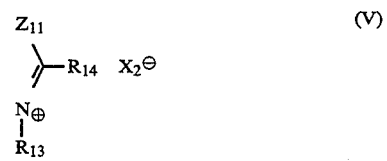  (V)

wherein $Z_{11}$ represents a non-metallic atomic group required for forming a 5-membered or 6-membered nitrogen-containing heterocyclic ring which may be condensed with a benzene ring or a naphthalene ring; $R_{13}$ represents a hydrogen atom, an alkyl group or an alkenyl group; $R_{14}$ represents a hydrogen atom or a lower alkyl group; and $X_2^\ominus$ represents an acid anion,

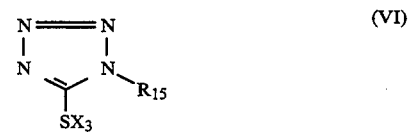  (VI)

wherein $R_{15}$ represents an alkyl group, an alkenyl group or an aryl group; and $X_3$ represents a hydrogen atom, an alkali metal atom, an ammonium group or a precursor,

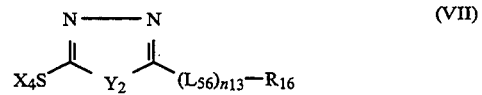  (VII)

wherein $Y_2$ represents oxygen atom, sulfur atom, =NH or =N—$(L_{57})_{n14}$—$R_{17}$; $L_{56}$ and $L_{57}$ represent each a bivalent bonding group; $R_{16}$ and $R_{17}$ represent each a hydrogen atom, an alkyl group, an alkenyl group or an aryl group; $X_4$ represents a hydrogen atom, an alkali metal atom, an ammonium group or a precursor; and $n_{13}$ and $n_{14}$ represent each 0 or 1.

14. A silver halide emulsion as in claim 12, wherein Ar represents a group which has an aromatic character and derives from a polycyclic carbon compound whose ring is composed of 9 or more carbon atoms.

15. A silver halide emulsion as in claim 12, wherein Q represents a bivalent bonding group having not more than 20 carbon atoms, which is composed of an alkylene group, an arylene group, an alkenylene group, a sulfonyl group, a sulfinyl group, a thioether group, an ether group, a carbonyl group, a group of

(wherein $R^1$ is a hydrogen atom, an alkyl group or an aryl group) or a heterocyclic bivalent group or a combination of two or more of these groups.

16. A silver halide emulsion as in claim 12, wherein the methine dye is incorporated in the silver halide emulsion in an amount of $5\times10^{-7}$ to $5\times10^{-3}$ mol per mol of silver halide.

17. A silver halide emulsion as in claim 12, wherein the methine dye is incorporated in the silver halide emulsion in an amount of $1\times10^{-6}$ to $1\times10^{-3}$ mol per mol of silver halide.

* * * * *